United States Patent
Fett et al.

(10) Patent No.: US 10,077,237 B2
(45) Date of Patent: Sep. 18, 2018

(54) OXINDOLE DERIVATIVES, PREPARATION THEREOF AND THERAPEUTIC USE IN THE TREATMENT OF AMPK-RELATED DISEASES

(71) Applicant: Sanofi, Paris (FR)

(72) Inventors: Eykmar Fett, Paris (FR); Patrick Mougenot, Paris (FR); Claudie Namane, Paris (FR); Eric Nicolai, Paris (FR); Olivier Venier, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 15/102,366

(22) PCT Filed: Dec. 19, 2014

(86) PCT No.: PCT/EP2014/078715
§ 371 (c)(1),
(2) Date: Jun. 7, 2016

(87) PCT Pub. No.: WO2015/091937
PCT Pub. Date: Jun. 25, 2015

(65) Prior Publication Data
US 2016/0311770 A1 Oct. 27, 2016

(30) Foreign Application Priority Data
Dec. 19, 2013 (EP) .................................. 13306793

(51) Int. Cl.
| | | |
|---|---|---|
| *C07D 401/06* | (2006.01) | |
| *C07D 403/06* | (2006.01) | |
| *C07D 403/10* | (2006.01) | |
| *C07D 413/06* | (2006.01) | |
| *C07D 417/06* | (2006.01) | |
| *C07D 209/34* | (2006.01) | |
| *C07D 413/14* | (2006.01) | |
| *C07D 417/14* | (2006.01) | |
| *C07D 491/048* | (2006.01) | |
| *C07D 491/107* | (2006.01) | |

(52) U.S. Cl.
CPC ......... *C07D 209/34* (2013.01); *C07D 401/06* (2013.01); *C07D 403/06* (2013.01); *C07D 403/10* (2013.01); *C07D 413/06* (2013.01); *C07D 413/14* (2013.01); *C07D 417/06* (2013.01); *C07D 417/14* (2013.01); *C07D 491/048* (2013.01); *C07D 491/107* (2013.01)

(58) Field of Classification Search
None
See application file for complete search history.

(56) References Cited

U.S. PATENT DOCUMENTS

| | | |
|---|---|---|
| 3,767,653 A | 10/1973 | Krapcho |
| 3,923,996 A | 12/1975 | Hardtmann |
| B348,433 I5 | 2/1976 | Krapcho |
| 3,984,405 A | 10/1976 | Krapcho |
| 8,778,973 B2 | 7/2014 | Chen et al. |

FOREIGN PATENT DOCUMENTS

| | | |
|---|---|---|
| AU | 1973/058745 | 2/1975 |
| DE | 2338668 | 2/1974 |
| WO | WO 1990/008145 | 7/1990 |
| WO | WO 2011/032320 | 3/2011 |
| WO | WO 2011/033099 | 3/2011 |

OTHER PUBLICATIONS

Park, KS. "Prevention of type 2 *Diabetes mellitus* from the viewpoint of genetics." Diabetes Research and Clinical Practice, 2004; 66S: S33-S35.*
Cool, B. et al., Identification and characterization of a small molecule AMPK activator that treats key components of type 2 diabetes and the metabolic syndrome, Cell Metabolism, Jun. 2006, pp. 3, 403-416.
European Search Report in European Application No. 13306793, dated Mar. 18, 2014, 8 pages.
Yu. L.-F. et al., AMPK activators as novel therapeutics for type 2 diabetes, Current topics in Medicinal Chemistry, vol. 10, 2010, pp. 397-410.
Foretz, M. et al., Short-term overexpression of a constitutively active form of AMP-activated protein kinase in the liver leads to mild hypoglycemia and fatty liver, Diabetes, May 2005, vol. 54, pp. 1331-1339.
Hallows, K. et al., Role of the energy sensor AMP-activated protein kinase in renal physiology and disease, Am. J. Renal Physiol. 298, Feb. 24, 2010, pp. F1067-F1077.
Hardie, D. et al., AMP-Activated protein kinase as a drug target, Annual Review of Pharmacology and Toxicology, Feb. 2007, vol. 47, pp. 185-210.
International Preliminary Report on Patentability in International Application No. PCT/EP2014/078715, dated Jun. 21, 2016, 8 pages.
International Search Report and Written Opinion in International Application No. PCT/EP2014/078715, dated Feb. 23, 2015, 12 pages.
LeBrasseur, N. et al., Thiazolidinediones can rapidly activate AMP-activated protein kinase in mammalian tissues, Am. J. Physiol. Endocrinol Metab, Feb. 7, 2006, pp. 291, E175-E181.

(Continued)

*Primary Examiner* — Anna Pagonakis
(74) *Attorney, Agent, or Firm* — Fish & Richardson P.C.; Vasily A. Ignatenko

(57) ABSTRACT

The present invention relates to compounds corresponding to formula (I). Process for the preparation thereof and therapeutic use thereof. The compounds are modulators of the activity of AMP-activated protein kinase (AMPK) and are useful for treating e.g. diabetes and obesity.

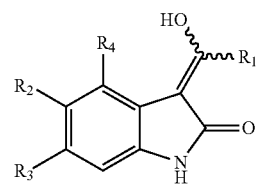

(I)

12 Claims, No Drawings

(56) References Cited

OTHER PUBLICATIONS

Merril, G. et al., AICA riboside increases AMP-activated protein kinase, fatty acid oxidation, and glucose uptake in rat muscle, American Journal of Physiology, Dec. 1, 1997, vol. 273 (6 pt. 1), pp. E1107-E1112.
Musi, N. et al., Metformin increases AMP-activated protein kinase activity in skeletal muscle of subjects with type 2 diabetes, Diabetes, Jul. 2002, vol. 51, pp. 2074-2081.
Pang, T. et al., Small molecule antagonizes autoinhibition and activates AMP-activated protein kinase in cells, The Journal of Biological Chemistry, Mar. 5, 2008, vol. 283 (23), pp. 16051-16060.
Pastor-Soler, N. et al., AMP-activated protein kinase regulation of kidney tubular transport, Current Opinion in Nephrology and Hypertension, Sep. 2012, vol. 21(5), pp. 523-533.
Polonsky, K., Dynamics of insulin secretion in obesity and diabetes, International Journal of Obesity, vol. 24, 2000, Suppl 2, pp. S29-S31.
Sullivan, J. et al., Inhibition of lipolysis and lipogenesis in isolated rat adipocytes with AICAR, a cell-permeable activator of AMP-activated protein kinase, Federation of European Biochemical Societies letters (FEBS Lett.), 1994, 353 (1), pp. 33-36.
Tanaka, Y. et al., Autophagy as a therapeutic target in diabetic nephropathy, Experimental Diabetes Research, vol. 2012, Article ID628978, Oct. 19, 2011, 12 pages.
Viollet, B. et al., AMPK inhibition in health and disease, Critical Reviews in Biochemistry and Molecular Biology, Aug. 2010, vol. 45(4), pp. 276-295.
Williams, T. et al., LKB1 and AMPK in cell polarity and division, Trends in Cell Biology, Mar. 7, 2008, vol. 18(4), pp. 193-198.

\* cited by examiner

OXINDOLE DERIVATIVES, PREPARATION THEREOF AND THERAPEUTIC USE IN THE TREATMENT OF AMPK-RELATED DISEASES

CROSS-REFERENCE TO RELATED APPLICATIONS

This application is a U.S. national stage application under 35 USC § 371 of International Application No. PCT/EP2014/078715, filed on Dec. 19, 2014, which claims priority to European Patent Application No. 13306793.4, filed on Dec. 19, 2013, the entire contents of which are incorporated herein by reference.

The present invention relates to oxindole derivatives, and to the preparation and therapeutic use thereof.

The compounds according to the invention modulate the activity of AMP-activated protein kinase (AMPK) and are of use for the prevention or treatment of pathological conditions in which such a modulation is beneficial, as in case of metabolic disorders including obesity and type 2 diabetes, as well as in case of kidney diseases.

AMPK is a sensor of the energy level in mammalian cells and also of the overall energy level in the organism. AMPK is activated by an increase in the intracellular AMP/ATP ratio, induced for example by a metabolic stress, hormones or the nutrient signalling pathways (Viollet et al., Critical Reviews in Biochemistry and Molecular Biology, 2010; 45(4); 276). When it is activated, AMPK blocks the metabolic pathways which consume ATP (such as fatty acid synthesis in adipocytes, cholesterol synthesis in the liver and insulin secretion in β-cells) and activates the metabolic pathways which produce ATP (such as fatty acid absorption and beta-oxidation in various tissues, glycolysis in the heart and the biogenesis of mitochondria in skeletal muscle). AMPK also modulates the transcription of genes which participate in energy metabolism, exerting a metabolic control over the longer term (Viollet et al., 2006). Moreover, the activity of AMPK also participates in the regulation of non-metabolic processes such as cell growth, progression of the cell cycle and organization of the cytoskeleton (Williams, T., and Brenman, J. E. (2008). Trends in Cell Biology 18(4):193-8). Although the activation of AMPK is an adaptive response to an energy stress in many biological systems, AMPK plays an important role in maintaining physiological functions and in adaptation to pathophysiological conditions.

The main pathological conditions in which the activation of AMPK intervenes are described below:

Metabolic Diseases Including Obesity and Type 2 Diabetes

Diabetes is characterized by a high level of plasma glucose (hyperglycaemia) in the fasted state or after the administration of glucose during an oral glucose tolerance test. Patients with type 2 (or non-insulin-dependent) diabetes exhibit, in addition to an increase in plasma glucose level, resistance to insulin. It is characterized by a lack of response to a stimulation induced by an increase in blood glucose at the level of the main target tissues of insulin, such as muscle, liver and adipose tissue. These patients compensate for the reduction in insulin effectiveness by increasing its production and are hyperinsulinemic (high level of plasma insulin) (Polonsky, Int. J. Obes. relat. Metab. Disord. 24 Suppl 2:S29-31, 2000). This increase in insulin secretion contributes, for a limited period of time, to maintaining a normal plasma glucose level. Over time, the pancreatic β-cells become exhausted, insulin production decreases and plasma glucose level increases leading to type 2 diabetes. Persistent or uncontrolled hyperglycaemia is associated with an increase in morbidity and premature mortality. It is directly or indirectly associated with obesity, hypertension and an impairment of lipid, lipoprotein and apolipoprotein metabolism. Patients with type 2 diabetes have a significant increase in the risks of macrovascular and microvascular complications, including atherosclerosis, coronary artery disease, strokes, peripheral vascular diseases, nephropathy, neuropathy and retinopathy. A considerable therapeutic need exists since virtually half the patients treated do not manage to correctly control their plasma glucose levels. Moreover, effective therapeutic control of glucose homeostasis prevents the occurrence of diabetes-related complications and significantly decreases mortality and morbidity. Insulin-resistant patients often have numerous symptoms which combined together are known as metabolic syndrome. This syndrome is associated with an increase in the risk of developing atherosclerosis and also coronary heart disease.

Numerous data accumulated over the past few years support the rationale which presents AMPK (AMP-activated protein kinase) as a therapeutic target of interest for the treatment of metabolic diseases including obesity and type 2 diabetes (Fang et al. Current topics in Medicinal Chemistry, 2010, 10, 397-340). The activation of AMPK via a modification of the AMP/ATP ratio or following phosphorylation by an upstream kinase like LKB1 or CaMKK can result in an increase in glucose uptake in the muscles and in a decrease in neoglucogenesis in the liver, both leading to a decrease in plasma glucose level. In terms of lipid metabolism, AMPK activation leads to an increase in fatty acid oxidation in the liver and the adipose tissue and also an increase in mitochondrial biogenesis (Hardie, D. Annu. Rev. Pharmacol. Toxicol., 2007, 47, 185-210). Moreover, it has been reported that the overexpression of an active form of AMPK in mouse liver produces a slight hypoglycaemia and decreases hyperglycaemia in a diabetic mouse model (Foretz et al. Diabetes, 2005, 54, 1331-1339). Furthermore, two classes of drugs widely used to treat type 2 diabetes, biguanides (Metformin, etc.) and thiazolidinediones (rosiglitazone, etc.), although indirectly, activate AMPK and this activation may at least partially explain their widely described antidiabetic effects (Lebrasseur, N. K. et al. Am. J. Physiol. Endocrinol. Metab., 2006, 291, E175-181; Musi, N. et al. Diabetes, 2002, 51, 2074-2081). Direct activators of AMPK have, moreover, shown positive effects in in vitro and in vivo preclinical models: AICAR (5-aminoimidazole-4-carboxamide riboside; Sullivan, J. E. et al. FEBS Lett., 1994, 353, 33-36; Merril, G. F. et al.; Am. J. Physiol., 1997, 273, E1107-1112), A769662 (Cool, B. et al., Cell Metabolism, 2006, 3, 403-416), and PT1 (Pang, T. et al. J. Biol. Chem., 2008, 283, 16051-16060). These data supports the rationale that direct activation of AMPK has the potential to improve the metabolic profile of type 2 diabetic patients with or without associated obesity. Moreover, the activation of AMPK using pharmacological agents could play a key role in the prevention of the occurrence of diabetic complications (nephropathy, neuropathy, retinopathy, atherosclerosis, microangiopathy).

AMPK Activation and Kidney Diseases

AMPK has been highlighted as a promising target for pharmacological modulation that yield benefits in the treatment of several kidney diseases (K. R. Hallows et al. AM. J. Renal. Physiol. 2010, 298, F1067-F1077). AMPK has been recently identified as regulator of several ion channels, transporters, and pumps in the kidney and treatment with AMPK activators may be beneficial in preventing deleterious effects in the kidney in the setting of various diseases (N. M. Pastor-Soler et al. Curr. Opin. Nephrol. Hypertens. 2012, 21(5): 523-33). Moreover, AMPK activation has been shown to induce autophagy, a lysosomal protein degradation pathway in cells, which has been shown to be renoprotective in several animal models (Y. Tanaka Exp. Diabetes Res. 2012, ID628978).

The present invention relates to compounds corresponding to formula (I):

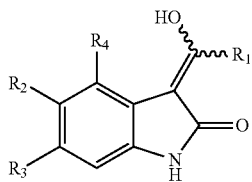
(I)

in which $R_1$ represents:
  an $(C_6-C_{10})$aryl group, unsubstituted or substituted with one or more substituents chosen from
    a halogen atom,
    a —$OR_a$ group, in which $R_a$ represents a hydrogen atom, a $(C_1-C_3)$alkyl group or a —$CF_3$ group
    a $(C_1-C_3)$alkyl group, unsubstituted or substituted with one or more halogen atoms,
    a carboxyl group,
    a $(C_3-C_6)$heterocycloalkyl group, unsubstituted or substituted with one or more $(C_1-C_3)$alkyl group,
  a $(C_2-C_{10})$heteroaryl group, unsubstituted or substituted with one or more substituents chosen from
    a halogen atom,
    a $(C_1-C_4)$alkyl group,
    a $(C_3-C_6)$cycloalkyl group,
    a —$OR_e$ group, in which $R_e$ represents an hydrogen atom or a $(C_1-C_4)$alkyl group, said $(C_1-C_4)$alkyl group being unsubstituted or substituted with one or more $(C_1-C_4)$alkoxy or heterocycloalkyl group
    a —$NR_fR_{f'}$ group, in which $R_f$ et $R_{f'}$, independently, identical or different, represent a $(C_1-C_3)$alkyl group $R_2$ represents:
  an $(C_6-C_{10})$aryl group, unsubstituted or substituted with one or more substituents chosen from:
    a halogen atom,
    a cyano group,
    a

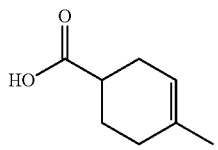

group
    a

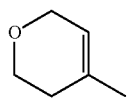

group
    a $(C_1-C_3)$alkyl group unsubstituted or substituted with one or more substituents chosen from a halogen atom, a hydroxyl group and a $(C_1-C_4)$ alkenyl group,
    a $(C_3-C_6)$cycloalkyl group, unsubstituted or substituted with a hydroxy$(C_1-C_3)$alkyl group, a hydroxyl group or an $(C_1-C_4)$alkoxy group,
    a —$OR_b$ group, in which $R_b$ represents
      a hydrogen atom,
      a —$CF_3$ group,
      a $(C_3-C_6)$cycloalkyl group, unsubstituted or substituted with a hydroxyl group
      a $(C_3-C_6)$heterocycloalkyl group, said $(C_3-C_6)$heterocycloalkyl being unsubstituted or substituted with a $(C_1-C_3)$alkyl group,
      or an $(C_1-C_3)$alkyl group, said $(C_1-C_3)$alkyl group being unsubstituted or substituted with one or more:
        hydroxyl group,
        $(C_1-C_4)$alkoxy group,
        $(C_2-C_{10})$heteroaryl group,
        acetamido group,
        di$(C_1-C_3)$alkyl-amino group,
        $(C_3-C_6)$cycloalkyl group, said $(C_3-C_6)$cycloalkyl group being unsubstituted or substituted with one or more hydroxyl group, or
        $(C_3-C_6)$heterocycloalkyl group, said $(C_3-C_6)$ heterocycloalkyl group being unsubstituted or substituted with a $(C_1-C_3)$alkyl group;
    a $(C_3-C_6)$heterocycloalkyl group unsubstituted or substituted with one or more halogen atom, $(C_1-C_3)$alkyl group, hydroxyl group, hydroxy$(C_1-C_3)$ alkyl group, $(C_1-C_4)$alkoxy group or $(C_1-C_4)$fluoroalkyl group,
    an $(C_6-C_{10})$aryl group, unsubstituted or substituted with one or more —$OR_c$ group, in which $R_c$ represents a hydrogen atom or a $(C_1-C_3)$alkyl group,
    a $(C_2-C_{10})$heteroaryl group, unsubstituted or substituted with one or more —$NH_2$ group,
    a —$NR_dR_{d'}$ group, in which $R_d$ et $R_{d'}$, independently, identical or different, represent a hydrogen atom, a $(C_1-C_3)$alkyl group, a hydroxy$(C_1-C_4)$alkyl or a $(C_3-C_6)$cycloalkyl group,
    a $(C_2-C_{10})$heteroaryl group, unsubstituted or substituted with one or more substituents chosen from:
      a $(C_1-C_3)$alkyl group
      a $(C_3-C_6)$cycloalkyl group, unsubstituted or substituted with a hydroxy$(C_1-C_3)$alkyl group,
      a —$NR_gR_{g'}$ group, in which $R_g$ et $R_{g'}$, independently, identical or different, represent a $(C_1-C_3)$alkyl group, $R_3$ represents:
  a halogen atom,
  a $(C_1-C_3)$alkyl group, $R_4$ represents:
  a halogen atom,
  a hydrogen atom, in the form of the base, enantiomers, diastereoisomers or of an addition salt with an acid or with a base.

The compounds of formula (I) may exist under the form of cis/trans isomers and/or under the form of isomers called tautomers. Such tautomers can be represented as follow:

All isomer forms which are not restricted to those described above and the mixtures of them are considered as part of the present invention.

The compounds of formula (I) may contain one or more asymmetric carbon atoms. They may therefore exist in the form of enantiomers or diastereoisomers. These enantiomers and diastereoisomers, and also mixtures thereof, including the racemic mixtures, form part of the invention.

The compounds of formula (I) may exist in the form of bases or acids which can be salified with acids or bases, especially pharmaceutically acceptable acids or bases. Such addition salts are part of the invention.

These salts are prepared with pharmaceutically acceptable acids or bases, but salts of other acids and bases that are of use, for example, for purifying or isolating the compounds of formula (I) also form part of the invention. In particular, use will be made in the context of the invention of the sodium salt and hydrochloride salt.

In the context of the present invention, and unless otherwise mentioned in the text:
- a halogen atom: a fluorine atom, a chlorine atom, a bromine atom or an iodine atom;
- an alkyl group: unless otherwise mentioned in the text, a linear or branched saturated aliphatic group containing from 1 to 4. Examples that may be mentioned include methyl, ethyl, propyl, isopropyl, butyl, isobutyl or tert-butyl groups, in particular methyl, ethyl or tert-butyl groups;
- an alkenyl group: a linear or branched mono- or polyunsaturated aliphatic group containing, for example, one or two ethylenic unsaturations; optionally substituted: not substituted or substituted;
- a halogenoalkyl group: an alkyl group in which one or more hydrogen atoms have been substituted by a halogen atom;
- a hydroxyalkyl group: an alkyl group in which one or more hydrogen atoms have been substituted by a OH group;
- an alkoxy group: a radical —O-alkyl in which the alkyl group is as defined previously, in particular the —O-alkyl group is a methoxy or an ethoxy group;
- a cycloalkyl group: a saturated mono or bi-cyclic aliphatic group comprising between 3 and 6 carbon atoms. Examples that may be mentioned include cyclopropyl, cyclobutyl or cyclohexyl group;
- a heterocycloalkyl group: a mono or bi-cyclic alkyl group comprising between 3 and 6 carbon atoms and comprising 1 or 2 heteroatoms, such as nitrogen or oxygen. Examples that may be mentioned include piperazinyl, morpholinyl, tetrahydropyranyl, piperidinyl or pyrrolidinyl groups;
- an aryl group (Ar): a mono or bi-cyclic aromatic group comprising between 6 and 10 carbon atoms. An example of an aryl group that may be mentioned is the phenyl or naphtalene group;
- a heteroaryl group: a mono or bi cyclic aromatic group comprising between 2 and 10 carbon atoms and comprising between 1 and 3 heteroatoms, such as nitrogen, oxygen or sulfur. Examples that may be mentioned include pyridinyl, pyrazolyl, furanyl, isoxazolyl, thiazolyl, isothiazolyl, thiophenyl, indolyl, furopyridinyl, benzofuranyl, thienopyridinyl, pyrimidinyl and 1,3,4-oxadiazolyl groups;

Among the compounds of the present invention, mention may be made of a first subgroup of compounds of formula (I) in which $R_1$ represents:
- An aryl group, unsubstituted or substituted with one or more substituents chosen from
  - a halogen atom,
  - a —$OR_a$ group, in which $R_a$ represents a hydrogen atom or a ($C_1$-$C_3$)alkyl group,
  - a ($C_1$-$C_3$)alkyl group, unsubstituted or substituted with one or more halogen atoms,
  - a carboxyl group,
  - a cyano group,
- a heteroaryl group, unsubstituted or substituted with one or more substituents chosen from a halogen atom, a ($C_1$-$C_4$)alkyl group, a ($C_3$-$C_6$)cycloalkyl group, a ($C_1$-$C_4$)alkoxy group, $R_2$ represents:
- an aryl group, unsubstituted or substituted with one or more substituents chosen from:
  - a halogen atom,
  - a cyano group,
  - a ($C_1$-$C_3$)alkyl group,
  - a ($C_3$-$C_6$)cycloalkyl group, unsubstituted or substituted with a hydroxy($C_1$-$C_3$)alkyl group,
  - a —$OR_b$ group, in which $R_b$ represents a hydrogen atom, a —$CF_3$ group or an alkyl group, unsubstituted or substituted with one heterocycloalkyl group, the said heterocycloalkyl group being unsubstituted or substituted with a ($C_1$-$C_3$)alkyl group;
  - a heterocycloalkyl group, unsubstituted or substituted with one or more ($C_1$-$C_3$)alkyl group,
  - an aryl group, unsubstituted or substituted with one or more —$OR_c$ group, in which $R_c$ represents a hydrogen atom or a ($C_1$-$C_3$)alkyl group,
  - a heteroaryl group, unsubstituted or substituted with one or more —$NH_2$ group,
  - a —$NR_dR_{d'}$ group, in which $R_d$ et $R_{d'}$, independently, identical or different, represent a hydrogen atom, a ($C_1$-$C_3$)alkyl group,
- a heteroaryl group, unsubstituted or substituted with one or more cycloalkyl group, unsubstituted or substituted with a hydroxy($C_1$-$C_3$)alkyl group, $R_3$ represents:
  a halogen atom,
  a ($C_1$-$C_3$)alkyl group,
$R_4$ represents an hydrogen atom
in the form of the base or of an addition salt with an acid or with a base.

Among the compounds of the present invention, mention may be made of a second subgroup of compounds of formula (I) in which:
$R_1$ represents:
  An aryl group, in particular a phenyl group, optionally substituted with one or more substituents chosen from
    a halogen atom, in particular a fluorine or a chlorine atom,
    a —$OR_a$ group, in which $R_a$ represents a hydrogen atom or a ($C_1$-$C_3$)alkyl group in particular a methyl group,
    a ($C_1$-$C_3$)alkyl group, in particular a methyl group, optionally substituted by one or more halogen atoms, in particular a di or trifluoro-methyl group,
    a carboxyl group,
    a cyano group,
  a heteroaryl group, in particular a pyridinyl group, a pyrazolyl group, an isoxazolyl group, a thiazolyl group, an isothiazolyl group or a 1,3,4-oxadiazolyl group, optionally substituted by one or more substituents chosen from a halogen atom in particular a bromine atom, a ($C_1$-$C_4$)alkyl group, in particular a methyl group or a tert-butyl group, a cycloalkyl group, in particular a cyclopropyl group, an ($C_1$-$C_3$) alkoxy group in particular a methoxy group,
$R_2$ represents:
  an aryl group, in particular a phenyl or naphtalene group, optionally substituted by one or more substituents chosen from:
    a halogen atom, in particular a fluorine or a chlorine atom,
    a cyano group,
    a ($C_1$-$C_3$)alkyl group, in particular an ethyl group,
    a cycloalkyl group, in particular a cyclopropyl or a cyclobutyl group, optionally substituted by a hydroxy($C_1$-$C_3$)alkyl group, in particular a hydroxymethyl group,
    a —$OR_b$ group, in which $R_b$ represents a hydrogen atom, a —$CF_3$ group or an alkyl group in particular a ($C_1$-$C_3$)alkyl group, optionally substituted by one heterocycloalkyl group, in particular a piperazinyl group, the said heterocycloalkyl group being optionally substituted by a ($C_1$-$C_3$)alkyl group, in particular a methyl group;
    a heterocycloalkyl group, in particular a morpholinyl, a dihydropyranyl, a tetrahydropyranyl, a pyrrolidinyl, a tetrahydrofuranyl, a piperidinyl or a piperazinyl group, optionally substituted by one or more a ($C_1$-$C_3$)alkyl group, in particular a methyl group,
    an aryl group, in particular a phenyl group, optionally substituted by one or more —$OR_c$ group, in which $R_c$ represents a hydrogen atom or a ($C_1$-$C_3$)alkyl group, in particular a methyl group,
    a heteroaryl group, in particular a pyridinyl, a thiazolyl or a furanyl group, optionally substituted by one or more —$NH_2$ group,
    a —$NR_dR_{d'}$ group, in which $R_d$ et $R_{d'}$, independently, identical or different, represent a hydrogen atom, a ($C_1$-$C_3$)alkyl group, in particular a methyl group,
    a heteroaryl group, in particular a thiophene group, optionally substituted by one or more cycloalkyl group in particular a cyclopropyl group, optionally substituted by a hydroxy($C_1$-$C_3$)alkyl group in particular a hydroxymethyl group,
$R_3$ represents:
  a halogen atom, in particular a chlorine or a fluorine atom,
  a ($C_1$-$C_3$)alkyl group, in particular a methyl group,
$R_4$ represents:
  a halogen atom, in particular a fluorine atom
  a hydrogen atom,
in the form of the base, enantiomers, diastereoisomers or of an addition salt with an acid or with a base.

Among the compounds of the present invention, mention may be made of a third subgroup of compounds of formula (I) in which:
$R_1$ represents:
  a phenyl group, unsubstituted or substituted with one or more substituents chosen from:
    a fluorine atom or a chlorine atom,
    a —$OR_a$ group, in which $R_a$ represents a methyl group, a $CF_3$ group,
    a di or trifluoro-methyl group,
    a carboxyl group,
    a cyano group,
    a morpholine group, a methylpiperazine group
  a pyridinyl group, a pyrazolyl group, a pyrimidinyl group, an isoxazolyl group, a thiazolyl group, an isothiazolyl group, a 1,3,4-oxadiazolyle group, a thiazol-2onyl group, a thienyl group, a furyl group, a furopyridinyl group, a benzofuran-2-yl group, a thienopyridinyl group, an indolynonyl group, unsubstituted or substituted with one or more substituents chosen from:
    a bromine atom, a chlorine atom, a fluorine atom
    a methyl or tert-butyl group,
    a hydroxyl group
    a cyclopropyl group or a cyclohexyl group
    a —$OR_e$ group, in which $R_e$ represents a methyl group, an ethyl group, an isopropyl group, a methoxyethyl group, a morpholinoethyl group
    a dimethylamino group,
$R_2$ represents:
  a phenyl or a naphtalene group, unsubstituted or substituted with one or more substituents chosen from:
    a fluorine atom or a chlorine atom,
    a

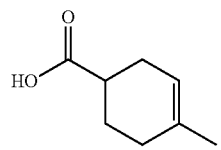

group
a

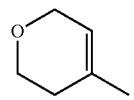

group
a cyano group,
an ethyl group, unsubstituted or substituted with one or two hydroxyl groups, an propyl group, unsubstituted or substituted with two or more groups chosen from a chlorine atom, an hydroxyl group and a propenyl group, a cyclopropyl or a cyclobutyl group, unsubstituted or substituted with a hydroxyl group, a hydroxymethyl group or a methoxy group a —$OR_b$ group, in which $R_b$ represents a hydrogen atom, a —$CF_3$ group or an ($C_1$-$C_3$)alkyl group, unsubstituted or substituted with one piperazinyl group, the said piperazinyl group being unsubstituted or substituted with a methyl group;

a morpholinyl, a dihydropyranyl, a tetrahydropyranyl, a pyrrolidinyle, a tetrahydrofuranyl, a piperazinyl, a piperidinyl group, a dioxane group, an oxaazaspiro[3.3]heptanyl, unsubstituted or substituted with one or more methyl group, hydroxyl group, methoxy group, hydroxymethyl group or fluorine atom, an azetidinyl group unsubstituted or substituted with one or two fluorine atoms, methyl groups, or hydroxymethyl group, a pyrrolidinyl group substituted with a trifluoroethyl group, a phenyl group, unsubstituted or substituted with one or more —$OR_c$ group, in which $R_c$ represents:
a hydrogen atom
a methyl group,
an hydroxypropyl group
an hydroxyxyxlohexyl group,
a methoxypropyl group,
a dimethylaminopropyl group
a morpholinoethyl group, a morpholinopropyl group
a hydroxypropyl group, a methoxyethyl group,
a tetrahydropyranyl,
a pyridylmethyl group,
a pyrimidinyl group,
a methylpiperidyl group,
a thiazolylmethyl group,
an acetamidoethyl group
an oxetanylmethyl group
an hydroxycyxlobutylmethyl group, a pyridinyl, a thiazolyl, a furanyl group, unsubstituted or substituted with one —$NH_2$ group, a —$NR_dR_{d'}$ group, in which $R_d$ et $R_{d'}$, independently, identical or different, represent a methyl group, an hydroxypropyl group or a cyclopropyl group, a thiophene group, unsubstituted or substituted with a cyclopropyl group, unsubstituted or substituted with a hydroxymethyl group, a pyrimidinyl or a pyridinyl group substituted with a dimethylamino group an indolyl group, substituted with a methyl group, $R_3$ represents:
a chlorine or a fluorine atom,
a methyl group, $R_4$ represents a fluorine or an hydrogen atom.

in the form of the base, enantiomers, diastereoisomers or of an addition salt with an acid or with a base.

Among the compounds of the present invention, mention may be made of a fourth subgroup of compounds of formula (I) in which:

$R_1$ represents a ($C_2$-$C_{10}$)heteroaryl group, optionally substituted by one or more substituents chosen from a halogen atom, a ($C_1$-$C_3$)alkyl group, a ($C_3$-$C_5$)cycloalkyl group, a ($C_1$-$C_4$)alkoxy group, in the form of the base, enantiomers, diastereoisomers or of an addition salt with an acid or with a base.

Among the compounds of the present invention, mention may be made of a fifth subgroup of compounds of formula (I) in which:

$R_1$ represents an isoxazolyl group, optionally substituted by one substituent chosen from a ($C_1$-$C_4$)alkyl group in particular a methyl group, a ($C_3$-$C_5$)cycloalkyl group, in particular a cyclopropyl group or a cyclohexyl group or an alkoxy group, in particular a methoxy group, in the form of the base, enantiomers, diastereoisomers or of an addition salt with an acid or with a base.

Among the compounds of the present invention, mention may be made of a sixth subgroup of compounds of formula (I) in which:

$R_1$ represents a phenyl group, substituted with one substituent chosen from halogen atom and an a —$OR_a$ group, in which $R_a$ represents a ($C_1$-$C_3$)alkyl group, Among the compounds of the present invention, mention may be made of an seventh subgroup of compounds of formula (I) in which:

$R_2$ represents:
an aryl group, in particular a phenyl group, optionally substituted by one or more substituents chosen from:
a ($C_1$-$C_3$)alkyl group,
a ($C_3$-$C_6$)cycloalkyl group, optionally substituted by a hydroxy($C_1$-$C_3$)alkyl group,
a ($C_3$-$C_6$)heterocycloalkyl group, in particular a morpholinyl, a dihydropyranyl, a tetrahydropyranyl, a pyrrolidinyl, a tetrahydrofuranyl, a piperidinyl or a piperazinyl group, optionally substituted by one or more ($C_1$-$C_3$)alkyl group, in particular a methyl group or an hydroxyl group,
an ($C_6$-$C_{10}$)aryl group, in particular a phenyl group, optionally substituted by one or more —$OR_c$ group, in which $R_c$ represents a hydrogen atom or a ($C_1$-$C_3$)alkyl group,
a ($C_2$-$C_{10}$)heteroaryl group, in particular a pyridinyl, a thiazolyl or a furanyl group, optionally substituted by one or more —$NH_2$ group,
a —$NR_dR_{d'}$ group, in which $R_d$ et $R_{d'}$, independently, identical or different, represent a hydrogen atom, a ($C_1$-$C_3$)alkyl group, in particular a methyl group, in the form of the base, enantiomers, diastereoisomers or of an addition salt with an acid or with a base.

Among the compounds of the present invention, mention may be made of an eighth subgroup of compounds of formula (I) in which:

$R_2$ represents:
a phenyl group, optionally substituted by one substituent chosen from:
a halogen atom,
a ($C_3$-$C_6$)cycloalkyl group, in particular a cyclopropyl group, optionally substituted by a hydroxy($C_1$-$C_3$)alkyl group in particular a hydroxymethyl group,
a ($C_3$-$C_6$)heterocycloalkyl group, in particular a dihydropyranyl group,
a phenyl group, optionally substituted by several —$OR_c$ group, in which $R_c$ represents a hydrogen atom or a ($C_1$-$C_3$)alkyl group in particular a methyl group,
a pyridinyl group,
a —$NR_dR_{d'}$ group, in which $R_d$ et $R_{d'}$, identical, represent a ($C_1$-$C_3$)alkyl group, in particular a methyl group, in the form of the base, enantiomers, diastereoisomers or of an addition salt with an acid or with a base.

Among the compounds of the present invention, mention may be made of a ninth subgroup of compounds of formula (I) in which $R_3$ represents a halogen atom, in particular a chlorine or a fluorine atom in the form of the base, enantiomers, diastereoisomers or of an addition salt with an acid or with a base Among the compounds of the present invention, mention may be made of a tenth subgroup of compounds of formula (I) in which: $R_4$ represents a fluorine atom, in the form of the base, enantiomers, diastereoisomers or of an addition salt with an acid or with a base.

Among the compounds of the present invention, mention may be made of a eleventh subgroup of compounds of formula (I) in which: when $R_4$ represents a fluorine then $R_3$ also represents a fluorine atom, in the form of the base, enantiomers, diastereoisomers or of an addition salt with an acid or with a base.

The subgroups defined above, taken separately or in combination, also form part of the invention.

Among the compounds of formula (I) that are subjects of the invention, mention may be made especially of the following compounds:

Compound 1. 6-Chloro-5-(4-dimethylamino-phenyl)-3-[1-hydroxy-1-(3-methyl-isoxazol-5-yl)-methylidene]-1,3-dihydro-indol-2-one Compound 2. 6-Chloro-5-(4-dimethylamino-phenyl)-3-[1-hydroxy-1-(3-methyl-isoxazol-5-yl)-methylidene]-1,3-dihydro-indol-2-one, sodium salt Compound 3. 6-Chloro-3-[1-hydroxy-1-(3-hydroxy-phenyl)-methylidene]-5-(4-morpholin-4-yl-phenyl)-1,3-dihydro-indol-2-one Compound 4. 3-{[6-Chloro-5-(4-morpholin-4-yl-phenyl)-2-oxo-1,2-dihydro-indolylidene]-hydroxy-methyl}-benzoic acid Compound 5. 6-Chloro-5-(2'-hydroxy-3'-methoxy-biphenyl-4-yl)-3-[1-hydroxy-1-(3-methoxy-isoxazol-5-yl)-methylidene]-1,3-dihydro-indol-2-one Compound 6. 6-Chloro-5-[4-(1-hydroxymethyl-cyclopropyl)-phenyl]-3-[1-hydroxy-1-(3-methyl-isoxazol-5-yl)-methylidene]-1,3-dihydro-indol-2-one Compound 7. 5-Biphenyl-4-yl-6-chloro-3-[1-hydroxy-1-phenyl-methylidene]-1,3-dihydro-indol-2-one Compound 8. 3-{[6-Chloro-5-(4-dimethylamino-phenyl)-2-oxo-1,2-dihydro-indolylidene]-hydroxy-methyl}-benzoic acid Compound 9. 4-{[6-Chloro-5-(4-dimethylamino-phenyl)-2-oxo-1,2-dihydro-indolylidene]-hydroxy-methyl}-benzoic acid Compound 10. 6-Chloro-5-(4-dimethylamino-phenyl)-3-[1-hydroxy-1-(2-methyl-thiazol-5-yl)-methylidene]-1,3-dihydro-indol-2-one Compound 11. 6-Chloro-3-[1-(3-fluoro-phenyl)-1-hydroxy-methylidene]-5-naphthalen-2-yl-1,3-dihydro-indol-2-one Compound 12. 6-Chloro-5-(2'-hydroxy-3'-methoxy-biphenyl-4-yl)-3-[1-hydroxy-1-(3-methyl-isoxazol-5-yl)-methylidene]-1,3-dihydro-indol-2-one Compound 13. 6-Chloro-3-[1-hydroxy-1-(3-methyl-isothiazol-5-yl)-methylidene]-5-(4-morpholin-4-yl-phenyl)-1,3-dihydro-indol-2-one Compound 14. 6-Chloro-3-[1-hydroxy-1-(3-methyl-isoxazol-5-yl)-methylidene]-5-(4-morpholin-4-yl-phenyl)-1,3-dihydro-indol-2-one Compound 15. 6-Chloro-3-[1-(2,4-dimethyl-thiazol-5-yl)-1-hydroxy-methylidene]-5-(4-morpholin-4-yl-phenyl)-1,3-dihydro-indol-2-one Compound 16. 6-Chloro-3-[1-hydroxy-1-(5-methyl-[1,3,4]oxadiazol-2-yl)-methylidene]-5-(4-morpholin-4-yl-phenyl)-1,3-dihydro-indol-2-one Compound 17. 6-Chloro-3-[1-hydroxy-1-(3-methoxy-isoxazol-5-yl)-methylidene]-5-(4-morpholin-4-yl-phenyl)-1,3-dihydro-indol-2-one Compound 18. 3-{[6-Chloro-5-(4-morpholin-4-yl-phenyl)-2-oxo-1,2-dihydro-indolylidene]-hydroxy-methyl}-benzonitrile Compound 19. 6-Chloro-3-[1-(3-fluoro-phenyl)-1-hydroxy-methylidene]-5-(4-morpholin-4-yl-phenyl)-1,3-dihydro-indol-2-one Compound 20. 6-Chloro-3-[1-hydroxy-1-(3-methyl-isoxazol-5-yl)-methylidene]-5-(4-methoxy-phenyl)-1,3-dihydro-indol-2-one Compound 21. 6-Chloro-5-[4-(3,6-dihydro-2H-pyran-4-yl)-phenyl]-3-[1-hydroxy-1-(3-methyl-isoxazol-5-yl)-methylidene]-1,3-dihydro-indol-2-one Compound 22. 6-Chloro-5-(4-cyclopropyl-phenyl)-3-[1-hydroxy-1-(3-methyl-isoxazol-5-yl)-methylidene]-1,3-dihydro-indol-2-one Compound 23. 6-Chloro-5-[4-(1-hydroxymethyl-cyclopropyl)-phenyl]-3-[1-hydroxy-1-(3-methyl-isothiazol-5-yl)-methylidene]-1,3-dihydro-indol-2-one Compound 24. 6-Chloro-3-[1-hydroxy-1-(3-methyl-isoxazol-5-yl)-methylidene]-5-(4-pyrrolidin-1-yl-phenyl)-1,3-dihydro-indol-2-one Compound 25. 6-Chloro-3-[1-hydroxy-1-pyridin-3-yl-methylidene]-5-(4-morpholin-4-yl-phenyl)-1,3-dihydro-indol-2-one Compound 26. 6-Chloro-5-(4-cyclopropyl-phenyl)-3-[1-(3-fluoro-phenyl)-1-hydroxy-methylidene]-1,3-dihydro-indol-2-one Compound 27. 6-Chloro-3-[1-(3-fluoro-phenyl)-1-hydroxy-methylidene]-5-[4-(1-hydroxymethyl-cyclopropyl)-phenyl]-1,3-dihydro-indol-2-one Compound 28. 6-Chloro-3-[1-hydroxy-1-(5-methyl-isoxazol-3-yl)-methylidene]-5-(4-morpholin-4-yl-phenyl)-1,3-dihydro-indol-2-one Compound 29. 6-Fluoro-3-[1-hydroxy-1-(3-methyl-isoxazol-5-yl)-methylidene]-5-(4-morpholin-4-yl-phenyl)-1,3-dihydro-indol-2-one Compound 30. 6-Chloro-5-(4-fluoro-phenyl)-3-[1-hydroxy-1-(3-methyl-isoxazol-5-yl)-methylidene]-1,3-dihydro-indol-2-one Compound 31. 3-[1-Hydroxy-1-(3-methyl-isoxazol-5-yl)-methylidene]-6-methyl-5-(4-morpholin-4-yl-phenyl)-1,3-dihydro-indol-2-one Compound 32. 6-Chloro-3-[1-(2-fluoro-phenyl)-1-hydroxy-methylidene]-5-(4-morpholin-4-yl-phenyl)-1,3-dihydro-indol-2-one Compound 33. 6-Chloro-3-[1-hydroxy-1-(3-methyl-isoxazol-5-yl)-methylidene]-5-(4-hydroxy-phenyl)-1,3-dihydro-indol-2-one Compound 34. 6-Chloro-3-[1-(3-chloro-phenyl)-1-hydroxy-methylidene]-5-(4-morpholin-4-yl-phenyl)-1,3-dihydro-indol-2-one Compound 35. 6-Chloro-3-[1-hydroxy-1-(3-methyl-isoxazol-5-yl)-methylidene]-5-(4-pyridin-4-yl-phenyl)-1,3-dihydro-indol-2-one, hydrochloride Compound 36. 6-Chloro-3-[1-(4-fluoro-phenyl)-1-hydroxy-methylidene]-5-(4-morpholin-4-yl-phenyl)-1,3-dihydro-indol-2-one Compound 37. 5-[4-(2-Amino-thiazol-4-yl)-phenyl]-6-chloro-3-[1-hydroxy-1-(3-methyl-isoxazol-5-yl)-methylidene]-1,3-dihydro-indol-2-one Compound 38. 4-{6-Chloro-3-[1-hydroxy-1-(3-methyl-isoxazol-5-yl)-methylidene]-2-oxo-2,3-dihydro-1H-indol-5-yl}-benzonitrile Compound 39. 6-Chloro-3-[1-(3-difluoromethyl-phenyl)-1-hydroxy-methylidene]-5-(4-morpholin-4-yl-phenyl)-1,3-dihydro-indol-2-one Compound 40. 6-Chloro-3-[1-hydroxy-1-(3-trifluoromethyl-phenyl)-methylidene]-5-(4-morpholin-4-yl-phenyl)-1,3-dihydro-indol-2-one Compound 41. 3-[1-(3-Bromo-isoxazol-5-yl)-1-hydroxy-methylidene]-6-chloro-5-(4-morpholin-4-yl-phenyl)-1,3-dihydro-indol-2-one Compound 42. 6-Chloro-5-(2'-hydroxy-3'-methoxy-biphenyl-4-yl)-3-[1-hydroxy-1-(3-methyl-isothiazol-5-yl)-methylidene]-1,3-dihydro-indol-2-one Compound 43. 6-Chloro-3-[1-hydroxy-1-phenyl-methylidene]-5-(4-morpholin-4-yl-phenyl)-1,3-dihydro-indol-2-one Compound 44. 6-Chloro-5-(3-fluoro-4-hydroxy-phenyl)-3-[1-hydroxy-1-(3-methyl-isoxazol-5-yl)-methylidene]-1,3-dihydro-indol-2-one Compound 45. 6-Chloro-5-[5-(1-hydroxymethyl-cyclopropyl)-thiophen-2-yl]-3-[1-hydroxy-1-(3-methyl-isoxazol-5-yl)-methylidene]-1,3-dihydro-indol-2-one Compound 46. 6-Chloro-3-[1-(2-fluoro-phenyl)-1-hydroxy-methylidene]-5-[4-(1-hydroxymethyl-cyclopropyl)-phenyl]-1,3-dihydro-indol-2-one Compound 47. 6-Chloro-3-[1-(2-fluoro-phenyl)-1-hydroxy-methylidene]-5-[4-(1-hydroxymethyl-cyclopropyl)-phenyl]-1,3-dihydro-indol-2-one, sodium salt Compound 48. 6-Chloro-5-[4-(3,6-dihydro-2H-pyran-4-yl)-phenyl]-3-[1-hydroxy-1-(3-methyl-isothiazol-5-yl)-methylidene]-1,3-dihydro-indol-2-one Compound 49. 6-Chloro-5-[4-(1-hydroxymethyl-cyclobutyl)-phenyl]-3-[1-hydroxy-1-(3-methyl-isoxazol-5-yl)-methylidene]-1,3-dihydro-indol-2-one Compound 50. 6-Chloro-3-[1-hydroxy-1-(3-methoxy-phenyl)-methylidene]-5-(4-morpholin-4-yl-phenyl)-1,3-dihydro-indol-2-one Compound 51. 6-Chloro-5-(2'-hydroxy-3'-methoxy-biphenyl-4-yl)-3-[1-hydroxy-1-(2-methyl-thiazol-5-yl)-methylidene]-1,3-dihydro-indol-2-one Compound 52. 6-Chloro-5-[4-(3,6-dihydro-2H-pyran-4-yl)-phenyl]-3-[1-(3-fluoro-phenyl)-1-hydroxy-methylidene]-1,3-dihydro-indol-2-one Compound 53. 6-Chloro-3-[1-hydroxy-1-(1-methyl-1H-pyrazol-3-yl)-methylidene]-5-(4-morpholin-4-yl-phenyl)-1,3-dihydro-indol-2-one Compound 54. 6-Chloro-3-[1-hydroxy-1-(3-methoxy-isoxazol-yl)-methylidene]-5-[4-(1-hydroxymethyl-cyclopropyl)-phenyl]-1,3-dihydro-indol-2-one Compound 55. 6-Chloro-5-(3-fluoro-4-methoxy-phenyl)-3-[1-hydroxy-1-(3-methyl-isoxazol-5-yl)-methylidene]-1,3-dihydro-indol-2-one Compound 56. 6-Chloro-5-(4-fluoro-2-hydroxy-phenyl)-3-[1-hydroxy-1-(3-methyl-isoxazol-5-yl)-methylidene]-1,3-dihydro-indol-2-one Compound 57. 6-Chloro-3-[1-hydroxy-1-(2-methyl-thiazol-4-yl)-methylidene]-5-(4-morpholin-4-yl-phenyl)-1,3-dihydro-indol-2-one Compound 58. 6-Chloro-3-[1-hydroxy-1-(3-methyl-isoxazol-5-yl)-methylidene]-5-(4-trifluoromethoxy-phenyl)-1,3-dihydro-indol-2-one Compound 59. 6-Chloro-3-[1-hydroxy-1-isoxazol-5-yl-methylidene]-5-(4-morpholin-4-yl-phenyl)-1,3-dihydro-indol-2-one Compound 60. 6-Chloro-3-[1-hydroxy-1-(3-methyl-isoxazol-4-yl)-methylidene]-5-(4-morpholin-4-yl-phenyl)-1,3-dihydro-indol-2-one Compound 61. 6-Chloro-3-[1-hydroxy-1-(3-methyl-isoxazol-5-yl)-methylidene]-5-[4-(tetrahydro-pyran-4-yl)-phenyl]-1,3-dihydro-indol-2-one Compound 62. 6-Chloro-3-[1-(5-cyclopropyl-isoxazol-3-yl)-1-hydroxy-methylidene]-5-(4-morpholin-4-yl-phenyl)-1,3-dihydro-indol-2-one Compound 63. 6-Chloro-5-(4-chloro-phenyl)-3-[1-hydroxy-1-(3-methyl-isoxazol-5-yl)-methylidene]-1,3-dihydro-indol-2-one Compound 64. 6-Chloro-5-(4-ethyl-phenyl)-3-[1-hydroxy-1-(3-methyl-isoxazol-5-yl)-methylidene]-1,3-dihydro-indol-2-one Compound 65. 6-Chloro-5-(4-furan-2-yl-phenyl)-3-[1-hydroxy-1-(3-methyl-isoxazol-5-yl)methylidene]-1,3-dihydro-indol-2-one Compound 66. 6-Chloro-5-(4-ethoxy-phenyl)-3-[1-hydroxy-1-(3-methyl-isoxazol-5-yl)-methylidene]-1,3-dihydro-indol-2-one Compound 67. 6-Chloro-5-[4-(3,6-dihydro-2H-pyran-4-yl)phenyl]-3-[1-hydroxy-1-(3-methoxy-isoxazol-5-yl)methylidene]-1,3-dihydro-indol-2-one Compound 68. 6-Chloro-3-[1-hydroxy-1-(3-methyl-isoxazol-5-yl)methylidene]-5-[4-(tetrahydro-furan-2-yl)phenyl]-1,3-dihydro-indol-2-one.

Compound 69. 6-Chloro-3-[1-hydroxy-1-(3-methyl-isoxazol-5-yl)methylidene]-5-[4-(3-piperazin-1-yl-propoxy)phenyl]-1,3-dihydro-indol-2-one, hydrochloride Compound 70. 6-Chloro-3-[1-hydroxy-1-(3-methyl-isoxazol-5-yl)methylidene]-5-{4-[3-(4-methyl-piperazin-1-yl)-propoxy]-phenyl}-1,3-dihydro-indol-2-one, hydrochloride Compound 71. 6-Fluoro-5-(2'-hydroxy-3'-methoxy-biphenyl-4-yl)-3-[1-hydroxy-1-(3-methoxy-isoxazol-5-yl)methylidene]-1,3-dihydro-indol-2-one Compound 72. 6-Fluoro-5-[4-(1-hydroxymethyl-cyclopropyl)phenyl]-3-[1-hydroxy-1-(3-methyl-isoxazol-5-yl)methylidene]-1,3-dihydro-indol-2-one Compound 73. 3-[1-(3-Bromo-isoxazol-5-yl)-1-hydroxy-methylidene]-6-chloro-5-[4-(1-hydroxymethyl-cyclopropyl)phenyl]-1,3-dihydro-indol-2-one Compound 74. 6-Chloro-3-[1-hydroxy-1-(3-methyl-isoxazol-5-yl)methylidene]-5-[4-(4-methyl-piperazin-1-yl)-phenyl]-1,3-dihydro-indol-2-one, hydrochloride Compound 75. 6-Chloro-5-[4-(1-hydroxymethyl-cyclopropyl)phenyl]-3-[1-hydroxy-1-(2-methyl-thiazol-5-yl)methylidene]-1,3-dihydro-indol-2-one Compound 76. 3-[1-(3-tert-Butyl-isoxazol-5-yl)-1-hydroxy-methylidene]-6-chloro-5-[4-(1-hydroxymethyl-cyclopropyl)phenyl]-1,3-dihydro-indol-2-one Compound 77. 6-Chloro-3-[1-(3-fluoro-4-methoxy-phenyl)-1-hydroxy-methylidene]-5-(4-morpholin-4-yl-phenyl)-1,3-dihydro-indol-2-one Compound 78. 6-Chloro-3-[1-hydroxy-1-(3-methyl-isoxazol-5-yl)methylidene]-5-[4-(1-methyl-piperidin-4-yl)phenyl]-1,3-dihydro-indol-2-one, hydrochloride Compound 79. 6-chloro-3-[hydroxy-[3-(2-methoxyethoxy)isoxazol-5-yl]methylene]-5-[4-(2-hydroxy-3-methoxyphenyl)phenyl]indolin-2-one Compound 80. 6-chloro-5-[4-[1-(chloromethyl)-1,2-dihydroxy-ethyl]phenyl]-3-[hydroxy-(3-methylisoxazol-5-yl)methylene]indolin-2-one Compound 81. 6-chloro-5-(4-hydroxy-3-methoxy-phenyl)-3-[hydroxy-(3-methylisoxazol-5-yl)methylene]indolin-2-one Compound 82. 6-chloro-3-[hydroxy-(3-methylisoxazol-5-yl)methylene]-5-[4-(2-morpholinoethoxy)phenyl]indolin-2-one hydrochloride Compound 83. 4,6-difluoro-3-[hydroxy-(3-methoxyisoxazol-5-yl)methylene]-5-[4-[1-(hydroxymethyl)cyclopropyl]phenyl]indolin-2-one Compound 84. 6-chloro-3-[(3-fluoro-4-methoxy-phenyl)hydroxy-methylene]-5-[4-(2-hydroxy-3-methoxy-phenyl)phenyl]indolin-2-one Compound 85. 6-chloro-5-[2-fluoro-4-[1-(hydroxymethyl)cyclopropyl]phenyl]-3-[hydroxy-(3-methylisoxazol-5-yl)methylene]indolin-2-one Compound 86. 6-chloro-3-[(3-cyclohexylisoxazol-5-yl)hydroxy-methylene]-5-(4-morpholinophenyl)indolin-2-one Compound 87. 6-chloro-3-[(3-cyclopropylisoxazol-5-yl)hydroxy-methylene]-5-(4-morpholinophenyl)indolin-2-one Compound 88. 6-chloro-3-[(3-fluoro-4-methoxy-phenyl)hydroxy-methylene]-5-[4-[1-(hydroxymethyl)cyclopropyl]phenyl]indolin-2-one Compound 89. 6-chloro-3-[hydroxy-(3-methoxyisoxazol-5-yl)methylene]-5-[4-(4-hydroxytetrahydropyran-4-yl)phenyl]indolin-2-one Compound 90. 6-chloro-5-[4-(2-hydroxy-3-methoxy-phenyl)phenyl]-3-[hydroxy-[3-(2-morpholinoethoxy)isoxazol-5-yl]methylene]indolin-2-one Compound 91. 6-chloro-3-[hydroxy-(3-methylisoxazol-5-yl)methylene]-5-[4-(3-hydroxypropoxy)phenyl]indolin-2-one Compound 92. 4,6-difluoro-3-[hydroxy-(3-methoxyisoxazol-5-yl)methylene]-5-[4-(2-hydroxy-3-methoxy-phenyl)phenyl]indolin-2-one Compound 93. 6-chloro-3-[hydroxy-[3-(4-methylpiperazin-1-yl)phenyl]methylene]-5-(4-morpholinophenyl)indolin-2-one hydrochloride Compound 94. 6-chloro-3-[hydroxy-(3-morpholinophenyl)methylene]-5-(4-morpholinophenyl)indolin-2-one Compound 95. 6-chloro-3-[[3-fluoro-4-(trifluoromethoxy)phenyl]-hydroxy-methylene]-5-(4-morpholinophenyl)indolin-2-one Compound 96. 6-chloro-5-[3-fluoro-4-[1-(hydroxymethyl)cyclopropyl]phenyl]-3-[hydroxy-(3-methoxyisoxazol-5-yl)methylene]indolin-2-one Compound 97. 6-chloro-3-[(3-chloro-5-fluoro-4-methoxy-phenyl)hydroxy-methylene]-5-(4-morpholinophenyl)indolin-2-one Compound 98. 6-chloro-3-[(2,3-difluoro-4-methoxy-phenyl)hydroxy-methylene]-5-(4-morpholinophenyl)indolin-2-one Compound 99. 6-chloro-3-[hydroxy-(3-methoxyisoxazol-5-yl)methylene]-5-[4-(3-morpholinopropoxy)phenyl]indolin-2-one Compound 100. 6-chloro-3-[hydroxy-(3-methoxyisoxazol-5-yl)methylene]-5-[4-(3-pyridylmethoxy)phenyl]indolin-2-one Compound 101. 6-chloro-3-[hydroxy-(3-methylisoxazol-5-yl)methylene]-5-[4-(pyrimidin-2-ylmethoxy)phenyl]indolin-2-one Compound 102. 6-chloro-3-[hydroxy-(3-hydroxyisoxazol-5-yl)methylene]-5-(4-morpholinophenyl)indolin-2-one Compound 103. 6-chloro-3-[hydroxy-(3-methylisoxazol-5-yl)methylene]-5-[4-(2-methoxyethoxy)phenyl]indolin-2-one Compound 104. N-[2-[4-[6-chloro-3-[hydroxy-(3-methylisoxazol-5-yl)methylene]-2-oxo-indolin-5-yl]phenoxy]ethyl]acetamide Compound 105. 6-chloro-3-[(3-ethoxyisoxazol-5-yl)hydroxy-methylene]-5-[4-(2-hydroxy-3-methoxy-phenyl)phenyl]indolin-2-one Compound 106. 6-chloro-3-[(3-cyclopropylisoxazol-5-yl)hydroxy-methylene]-5-[4-[1-(hydroxymethyl)cyclopropyl]phenyl]indolin-2-one Compound 107. 5-[-[6-chloro-5-(4-morpholinophenyl)-2-oxo-indolin-3-ylidene]-hydroxy-methyl]-4-methyl-3H-thiazol-2-one Compound 108. 6-chloro-3-[(2,5-difluoro-4-methoxy-phenyl)hydroxy-methylene]-5-(4-morpholinophenyl)indolin-2-one Compound 109. 6-chloro-3-[hydroxy-(3-isopropoxyisoxazol-5-yl)methylene]-5-[4-(2-hydroxy-3-methoxy-phenyl)phenyl]indolin-2-one Compound 110. 6-chloro-3-[hydroxy-(3-methoxyisoxazol-5-yl)methylene]-5-[4-(1-methoxycyclobutyl)phenyl]indolin-2-one Compound 111. 6-chloro-5-[2-fluoro-4-[1-(hydroxymethyl)cyclopropyl]phenyl]-3-[hydroxy-(3-methoxyisoxazol-5-yl)methylene]indolin-2-one Compound 112. 3-[(3-tert-butylisoxazol-5-yl)-hydroxy-methylene]6-chloro-5-(4-morpholinophenyl)indolin-2-one Compound 113. 6-chloro-3-[(3-cyclopropylisoxazol-5-yl)hydroxy-methylene]-5-[2-fluoro-4-[1-(hydroxymethyl)cyclopropyl]phenyl]indolin-2-one Compound 114. 6-chloro-5-[4-[1-(hydroxymethyl)cyclopropyl]phenyl]-3-[hydroxy(2-thienyl)methylene]indolin-2-one Compound 115. 6-chloro-3-[hydroxy-(3-methylisoxazol-5-yl)methylene]-5-[4-(oxetan-2-ylmethoxy)phenyl]indolin-2-one Compound 116. 6-chloro-3-[hydroxy-(6-methoxy-3-pyridyl)methylene]-5-[4-[1-(hydroxymethyl)cyclopropyl]phenyl]indolin-2-one hydrochloride Compound 117. 6-chloro-3-[(3-cyclopropylisoxazol-5-yl)hydroxy-methylene]-5-[4-(2-hydroxy-3-methoxy-phenyl)phenyl]indolin-2-one Compound 118. 6-fluoro-3-[hydroxy-(3-methoxyisoxazol-5-yl)methylene]-5-[4-[1-(hydroxymethyl)cyclopropyl]phenyl]indolin-2-one Compound 119. 3-[(3-cyclopropylisoxazol-5-yl)hydroxy-methylene]6-fluoro-5-[4-[1-(hydroxymethyl)cyclopropyl]phenyl]indolin-2-one Compound 120. 3-[(3-cyclopropylisoxazol-5-yl)hydroxy-methylene]-4,6-difluoro-5-[4-[1-(hydroxymethyl)cyclopropyl]phenyl]indolin-2-one Compound 121. 6-chloro-5-[4-[2-hydroxy-1-(hydroxymethyl)ethyl]phenyl]-3-[hydroxy-(3-methoxyisoxazol-5-yl)methylene]indolin-2-one Compound 122. 6-chloro-5-[4-(1,2-dihydroxyethyl)phenyl]-3-[hydroxy-(3-methoxyisoxazol-5-yl)methylene]indolin-2-one Compound 123. 6-chloro-5-[4-[1-(hydroxymethyl)cyclopropyl]phenyl]-3-[hydroxy-(5-methyl-2-thienyl)methylene]indolin-2-one Compound 124. 6-chloro-3-[hydroxy-(3-methoxyisoxazol-5-yl)methylene]-5-[4-[(1-methyl-4-piperidyl)oxy]phenyl]indolin-2-one hydrochloride Compound 125. 6-fluoro-3-[(3-fluoro-4-methoxy-phenyl)hydroxy-methylene]-5-[4-[1-(hydroxymethyl)cyclopropyl]phenyl]indolin-2-one Compound 126. 6-chloro-3-[2-furyl(hydroxy)methylene]-5-[4-[1-(hydroxymethyl)cyclopropyl]phenyl]indolin-2-one Compound 127. 6-chloro-5-(4-dimethylaminophenyl)-3-[hydroxy-(3-methoxyisoxazol-5-yl)methylene]indolin-2-one Compound 128. 6-chloro-3-[hydroxy-(3-methoxyisoxazol-5-yl)methylene]-5-(4-tetrahydropyran-4-yloxyphenyl)indolin-2-one Compound 129. 6-chloro-3-[hydroxy-(3-methoxyisoxazol-5-yl)methylene]-5-[4-(3-hydroxypropoxy)phenyl]indolin-2-one Compound 130. 6-chloro-3-[(5-chloro-2-thienyl)hydroxymethylene]-5-[4-[1-(hydroxymethyl)cyclopropyl]phenyl]indolin-2-one Compound 131. 6-chloro-3-[hydroxy-(3-methoxyisoxazol-5-yl)methylene]-5-[4-(3-methoxypropoxy)phenyl]indolin-2-one Compound 132. 6-chloro-3-[hydroxy-(3-methylisoxazol-5-yl)methylene]-5-[4-(oxetan-3-ylmethoxy)phenyl]indolin-2-one Compound 133. 6-chloro-3-[hydroxy-(3-methoxyisoxazol-5-yl)methylene]-5-[4-(1-methylpyrrolidin-3-yl)phenyl]indolin-2-one hydrochloride Compound 134. 6-chloro-3-[hydroxy-(3-methoxyisoxazol-5-yl)methylene]-5-(4-pyrrolidin-3-ylphenyl)indolin-2-one hydrochloride Compound 135. 6-chloro-5-[4-(3-hydroxycyclobutyl)phenyl]-3-[hydroxy-(3-methoxyisoxazol-5-yl)methylene]indolin-2-one Compound 136. 6-chloro-3-[hydroxy-(3-methoxyisoxazol-5-yl)methylene]-5-[4-(thiazol-5-ylmethoxy)phenyl]indolin-2-one Compound 137. 6-chloro-3-[hydroxy-(3-methoxyisoxazol-5-yl)methylene]-5-(4-pyrrolidin-1-ylphenyl)indolin-2-one Compound 138. 6-chloro-3-[(2,3-difluorophenyl)hydroxymethylene]-5-[4-[1-(hydroxymethyl)cyclopropyl]phenyl]indolin-2-one Compound 139. 6-chloro-5-[4-[(3-hydroxycyclobutyl)methoxy]phenyl]-3-[hydroxy-(3-methoxyisoxazol-5-yl)methylene]indolin-2-one Compound 140. 6-chloro-3-[hydroxy-(5-methoxy-2-pyridyl)methylene]-5-(4-morpholinophenyl)indolin-2-one Compound 141. 6-chloro-3-[(2,4-difluorophenyl)hydroxymethylene]-5-[4-[1-(hydroxymethyl)cyclopropyl]phenyl]indolin-2-one Compound 142. 6-chloro-3-[(5-fluoro-3-pyridyl)hydroxymethylene]-5-[4-[1-(hydroxymethyl)cyclopropyl]phenyl]indolin-2-one Compound 143. 6-chloro-3-[(3,4-difluorophenyl)hydroxymethylene]-5-[4-[1-(hydroxymethyl)cyclopropyl]phenyl]indolin-2-one Compound 144. 6-chloro-3-[(3,5-difluorophenyl)hydroxymethylene]-5-[4-[1-(hydroxymethyl)cyclopropyl]phenyl]indolin-2-one Compound 145. 6-chloro-5-[2-(dimethylamino)pyrimidin-5-yl]-3-[hydroxy-(3-methoxyisoxazol-5-yl)methylene]indolin-2-one Compound 146. 6-chloro-5-[6-(dimethylamino)-3-pyridyl]-3-[hydroxy-(3-methoxyisoxazol-5-yl)methylene]indolin-2-one Compound 147. 6-chloro-5-[4-(dimethylamino)-3-fluoro-phenyl]-3-[hydroxy-(3-methoxyisoxazol-5-yl)methylene]indolin-2-one Compound 148. 6-chloro-5-[4-(dimethylamino)-2-fluoro-phenyl]-3-[hydroxy-(3-methoxyisoxazol-5-yl)methylene]indolin-2-one Compound 149. 6-chloro-5-(3-fluoro-4-morpholino-phenyl)-3-[hydroxy-(3-methoxyisoxazol-5-yl)methylene]indolin-2-one Compound 150. 6-chloro-3-[(3,5-difluorophenyl)hydroxymethylene]-5-[4-(1-methylpyrrolidin-3-yl)phenyl]indolin-2-one hydrochloride Compound 151. 6-chloro-3-[hydroxy-(6-methoxy-3-pyridyl)methylene]-5-(4-morpholinophenyl)indolin-2-one Compound 152. 6-chloro-5-[4-(4-hydroxycyclohexoxy)phenyl]-3-[hydroxy-(3-methoxyisoxazol-5-yl)methylene]indolin-2-one Compound 153. 6-chloro-5-[4-[cyclopropyl(methyl)amino]phenyl]-3-[hydroxy-(3-methoxyisoxazol-5-yl)methylene]indolin-2-one Compound 154. 6-chloro-3-[hydroxy-(3-methoxyisoxazol-5-yl)methylene]-5-(1-methylindol-5-yl)indolin-2-one Compound 155. 6-chloro-3-[(2,4-difluorophenyl)hydroxymethylene]-5-[4-(3-hydroxycyclobutyl)phenyl]indolin-2-one Compound 156. 6-chloro-3-[hydroxy-(3-methoxyisoxazol-5-yl)methylene]-5-[4-(3-hydroxypyrrolidin-1-yl)phenyl]indolin-2-one Compound 157. 6-chloro-3-[furo[2,3-b]pyridin-2-yl(hydroxy)methylene]-5-[4-[1-(hydroxymethyl)cyclopropyl]phenyl]indolin-2-one Compound 158. 6-chloro-3-[hydroxy-(2-methoxy-4-pyridyl)methylene]-5-[4-[1-(hydroxymethyl)cyclopropyl]phenyl]indolin-2-one Compound 159. 6-chloro-3-[(2,5-difluoro-4-methoxy-phenyl)hydroxy-methylene]-5-[4-(3-hydroxycyclobutyl)phenyl]indolin-2-one Compound 160. 6-chloro-3-[(3-fluoro-4-pyridyl)hydroxymethylene]-5-[4-[1-(hydroxymethyl)cyclopropyl]phenyl]indolin-2-one Compound 161. 6-chloro-3-[(3,5-difluorophenyl)hydroxymethylene]-5-[4-(3-hydroxycyclobutyl)phenyl]indolin-2-one Compound 162. 5-[4-(azetidin-1-yl)phenyl]6-chloro-3-[hydroxy-(3-methoxyisoxazol-5-yl)methylene]indolin-2-one Compound 163. 6-chloro-3-[(2,4-dimethoxyphenyl)hydroxy-methylene]-5-[4-[1-(hydroxymethyl)cyclopropyl]phenyl]indolin-2-one Compound 164. 3-[(3-tert-butylisoxazol-5-yl)-hydroxymethylene]6-chloro-5-[4-(3-hydroxycyclobutyl)phenyl]indolin-2-one Compound 165. 6-chloro-3-[hydroxy-(3-methoxyisoxazol-5-yl)methylene]-5-[4-(3-methoxycyclobutyl)phenyl]indolin-2-one Compound 166. 6-chloro-5-[4-(3-hydroxycyclobutyl)phenyl]-3-[hydroxy-(3-isopropoxyisoxazol-5-yl)methylene]indolin-2-one Compound 167. 6-chloro-3-[hydroxy-(3-methoxyisoxazol-5-yl)methylene]-5-[4-[1-(2,2,2-trifluoroethyl)pyrrolidin-3-yl]phenyl]indolin-2-one hydrochloride Compound 168. 3-[benzofuran-2-yl(hydroxy)methylene]6-chloro-5-[4-[1-(hydroxymethyl)cyclopropyl]phenyl]indolin-2-one Compound 169. 6-chloro-3-[furo[3,2-b]pyridin-2-yl(hydroxy)methylene]-5-[4-[1-(hydroxymethyl)cyclopropyl]phenyl]indolin-2-one Compound 170. 6-chloro-3-[(5-chlorobenzofuran-2-yl)hydroxy-methylene]-5-[4-[1-(hydroxymethyl)cyclopropyl]phenyl]indolin-2-one Compound 171. 6-chloro-3-[(2-fluorophenyl)hydroxymethylene]-5-[4-(3-hydroxycyclobutyl)phenyl]indolin-2-one Compound 173. 6-chloro-5-[4-[3-(dimethylamino)propoxy]phenyl]-3-[hydroxy-(3-methoxyisoxazol-5-yl)methylene]indolin-2-one Compound 174. 6-chloro-3-[(3-cyclopropylisoxazol-5-yl)hydroxy-methylene]-5-[4-(3-hydroxycyclobutyl)phenyl]indolin-2-one Compound 175. 6-chloro-3-[hydroxy-(3-methoxy-4-pyridyl)methylene]-5-[4-[1-(hydroxymethyl)cyclopropyl]phenyl]indolin-2-one Compound 176. 6-chloro-5-[4-(2,2-dimethyl-1,3-dioxan-5-yl)phenyl]-3-[hydroxy-(3-methoxyisoxazol-5-yl)methylene]indolin-2-one Compound 177. 6-chloro-3-[hydroxy-(3-methoxyisoxazol-5-yl)methylene]-5-[4-(6-oxa-2-azaspiro[3.3]heptan-2-yl)phenyl]indolin-2-one Compound 178. 6-chloro-3-[hydroxy-(2-methoxy-3-pyridyl)methylene]-5-[4-[1-(hydroxymethyl)cyclopropyl]phenyl]indolin-2-one Compound 179. 6-chloro-3-[hydroxy-(3-methoxyisoxazol-5-yl)methylene]-5-[4-[3-hydroxypropyl(methyl)amino]phenyl]indolin-2-one Compound 180. 6-chloro-5-[4-(3-fluoroazetidin-1-yl)phenyl]-3-[hydroxy-(3-methoxyisoxazol-5-yl)methylene]indolin-2-one Compound 181. 6-chloro-5-[4-(3,3-difluoroazetidin-1-yl)phenyl]-3-[hydroxy-(3-methoxyisoxazol-5-yl)methylene]indolin-2-one Compound 182. 6-chloro-3-[furo[3,2-b]pyridin-2-yl(hydroxy)methylene]-5-[4-(3-hydroxypyrrolidin-1-yl)phenyl]indolin-2-one Compound 183. 6-chloro-3-[hydroxy-(6-methoxy-2-pyridyl)methylene]-5-[4-[1-(hydroxymethyl)cyclopropyl]phenyl]indolin-2-one Compound 184. 6-chloro-3-[hydroxy-(3-methoxy-2-pyridyl)methylene]-5-[4-[1-(hydroxymethyl)cyclopropyl]phenyl]indolin-2-one Compound 185. 6-chloro-3-[(3-ethoxyisoxazol-5-yl)hydroxy-methylene]-5-[4-(3-hydroxycyclobutyl)phenyl]indolin-2-one Compound 186. 6-chloro-3-[hydroxy-(3-methoxyisoxazol-5-yl)methylene]-5-[4-(1-methylazetidin-3-yl)phenyl]indolin-2-one Compound 187. 6-chloro-3-[hydroxy-(3-methoxyisoxazol-5-yl)methylene]-5-[4-[(3R)-3-hydroxypyrrolidin-1-yl]phenyl]indolin-2-one Compound 188. 6-chloro-3-[hydroxy-(3-methoxyisoxazol-5-yl)methylene]-5-[4-[(3S)-3-hydroxypyrrolidin-1-yl]phenyl]indolin-2-one Compound 189. 6-chloro-3-[(2-fluorophenyl)hydroxy-methylene]-5-[4-(3-hydroxypyrrolidin-1-yl)phenyl]indolin-2-one Compound 190. 6-chloro-3-[[2-(dimethylamino)pyrimidin-5-yl]-hydroxy-methylene]-5-[4-(3-hydroxypyrrolidin-1-yl)phenyl]indolin-2-one Compound 191. 6-chloro-5-[4-(3,3-dimethylazetidin-1-yl)phenyl]-3-[hydroxy-(3-methoxyisoxazol-5-yl)methylene]indolin-2-one Compound 192. 6-chloro-3-[(3-cyclopropylisoxazol-5-yl)hydroxy-methylene]-5-[4-(3-hydroxypyrrolidin-1-yl)phenyl]indolin-2-one Compound 193. 6-chloro-3-[hydroxy-(3-methoxyisoxazol-5-yl)methylene]-5-[4-[3-(hydroxymethyl)azetidin-1-yl]phenyl]indolin-2-one Compound 194. 6-chloro-5-[4-[1-(hydroxymethyl)cyclopropyl]phenyl]-3-[hydroxy(thieno[2,3-b]pyridin-2-yl)methylene]indolin-2-one hydrochloride Compound 195. 6-chloro-3-[hydroxy-(3-methoxyisoxazol-5-yl)methylene]-5-[4-[(3S,4S)-3-hydroxy-4-methoxy-pyrrolidin-1-yl]phenyl]indolin-2-one Compound 196. 6-chloro-5-[4-[1-(2-chloroethyl)-2-methyl-prop-1-enyl]phenyl]-3-[hydroxy-(3-methoxyisoxazol-5-yl)methylene]indolin-2-one Compound 197. 6-chloro-3-[hydroxy-(3-methoxyisoxazol-5-yl)methylene]-5-[4-(4-hydroxy-1-piperidyl)phenyl]indolin-2-one Compound 198. 6-chloro-5-[4-[(3R)-3-fluoropyrrolidin-1-yl]phenyl]-3-[hydroxy-(3-methoxyisoxazol-5-yl)methylene]indolin-2-one Compound 199. 6-chloro-3-[hydroxy-(1-methylindol-5-yl)methylene]-5-[4-(3-hydroxypyrrolidin-1-yl)phenyl]indolin-2-one Compound 200. 6-chloro-5-(2,6-fluoro-4-morpholino-phenyl)-3-[hydroxy-(3-methoxyisoxazol-5-yl)methylene]indolin-2-one Compound 201. 6-chloro-3-[hydroxy-(3-methoxyisoxazol-5-yl)methylene]-5-[4-[2-(hydroxymethyl)azetidin-1-yl]phenyl]indolin-2-one Compound 202. 6-chloro-3-[hydroxy-(3-methoxyisoxazol-5-yl)methylene]-5-[4-[(2S)-2-(hydroxymethyl)pyrrolidin-1-yl]phenyl]indolin-2-one Compound 203. 6-chloro-3-[hydroxy-(3-methoxyisoxazol-5-yl)methylene]-5-[4-[(2R)-2-(hydroxymethyl)pyrrolidin-1-yl]phenyl]indolin-2-one Compound 204. 4-[4-[6-chloro-3-[hydroxy-(3-methoxy-isoxazol-5-yl)methylene]-2-oxo-indolin-5-yl]phenyl]cyclohex-3-ene-1-carboxylic acid Compound 205. trans-6-chloro-3-[hydroxy-(3-methoxy-isoxazol-5-yl)methylene]-5-[4-[(3S,4R)-4-hydroxytetrahydrofuran-3-yl]phenyl]indolin-2-one Compound 206. cis-6-chloro-3-[hydroxy-(3-methoxyisoxazol-5-yl)methylene]-5-[4-[(2S,4S)-4-hydroxytetrahydrofuran-2-yl]phenyl]indolin-2-one Compound 207. trans-6-chloro-3-[hydroxy-(3-methoxy-isoxazol-5-yl)methylene]-5-[4-[(2R,4S)-4-hydroxytetrahydrofuran-2-yl]phenyl]indolin-2-one Compound 208. 6-chloro-3-[hydroxy-(3-methoxyisoxazol-5-yl)methylene]-5-[4-(4-hydroxy-4-methyl-1-piperidyl)phenyl]indolin-2-one Compound 209. 6-chloro-3-[hydroxy-(3-methoxyisoxazol-5-yl)methylene]-5-[4-[2-(hydroxymethyl)morpholin-4-yl]phenyl]indolin-2-one Compound 210. 6-chloro-3-[hydroxy-(3-methoxyisoxazol-5-yl)methylene]-5-[4-[3-(hydroxymethyl)morpholin-4-yl]phenyl]indolin-2-one in the form of the base, enantiomers, diastereoisomers or of an addition salt with an acid or with a base.

It should be noted that the above compounds were named according to the IUPAC nomenclature by means of the Autonom software.

In what follows, we understand by protective group (PG), a group which allows, on one hand to protect a reactive function such as a hydroxy or an amine during a synthesis and, on the other hand to regenerate the intact reactive function at the end of the synthesis. Examples of protective groups as well as methods of protection and of deprotection are given in "Protective Groups in Organic Synthesis", Green and al., 4rd Edition (Publishing) (John Wiley and Sounds, Inc., New York).

In schemes 1 to 6, the starting materials and reagents, when method for preparing them is not described, are commercially available or are readily prepared using methods well-known to those skilled in the art or described in the literature.

According to another of its aspects, a subject of the invention is also the compounds of formulae (VII), (IX), (XI), (XII) and (XIV). These compounds are useful as intermediates in the synthesis of the compounds of formula (I).

Schemes 1 through 6 outline the general procedures useful for the preparation of compounds of the present invention.

In accordance with the invention, oxindole derivatives of general formula (I), wherein $R_1$, $R_2$, $R_3$ and $R_4$ are as defined above, can be synthesized as shown in Scheme 1.

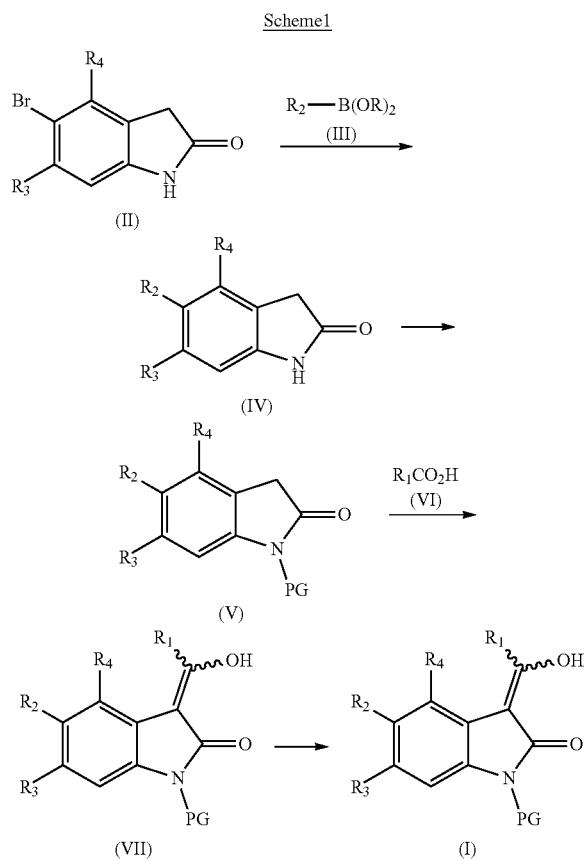

5-bromo oxindoles of general formula (II), wherein $R_3$ and $R_4$ are as defined in general formula (I), and boron derivatives of general formula (III), wherein $R_2$ is as defined in general formula (I) and $B(OR)_2$ is a boronic acid or a boronate, can be coupled using palladium catalysts such as PddppfCl$_2$ or tetrakistriphenylphosphine palladium at temperatures ranging from 25° C. to 130° C. with conventional heat or microwave heat for 30 minutes to 24 hours to provide compounds of general formula (IV). Compounds of general formula (IV) can be treated with protecting reagents such as acetyl chloride, Boc$_2$O or the like to provide oxindoles of general formula (V). Oxindoles of general formula (V) can be acylated with a variety of carboxylic acid derivatives of formula (VI) (wherein $R_1$ is as defined in the general formula (I)). The reaction can be carried out in solvents like dimethylformamide in the presence of an activating agent such as TBTU to provide compounds of general formula (VII). Removal of the protective group can be performed with a variety of acidic or basic reagents such as hydrogen chloride in dioxane or other solvents, trifluoroacetic acid, sodium hydroxide in an alcohol like ethanol or methanol, to provide compounds of general formula (I).

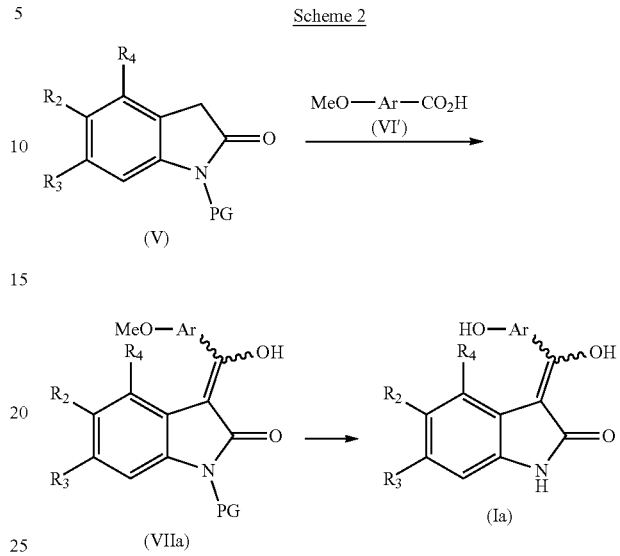

Oxindoles of general formula (Ia) corresponding to the compounds of general formula (I), wherein $R_2$, $R_3$ and $R_4$ are as defined in the general formula (I) and $R_1$ represents an aryl group substituted with a hydroxy group (HO—Ar), can be prepared as shown in Scheme 2 by both deprotection and demethylation of a compound of general formula (VIIa), wherein $R_2$, $R_3$ and $R_4$ are as defined in the general formula (I) and $R_1$ represents an aryl group substituted with a methoxy group (MeO—Ar), with an acidic reagent such as BBr$_3$. Compounds of formula (VIIa) can be prepared according to Scheme 1.

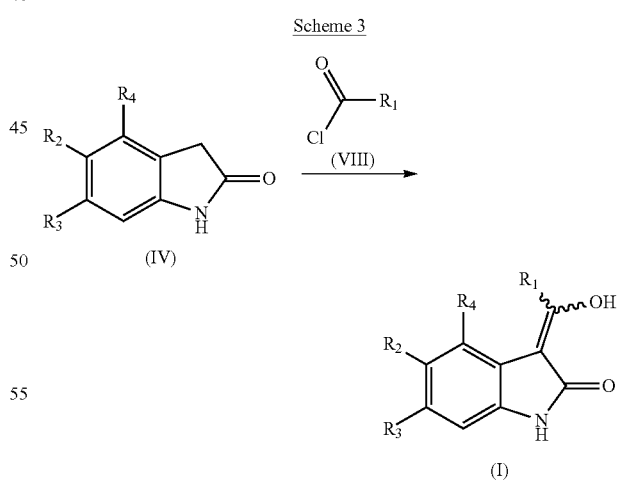

Oxindoles of general formula (I), wherein $R_1$, $R_2$, $R_3$ and $R_4$ are as defined above can also be synthesized according to Scheme 3 by reaction of a compound (IV) with an acyl halide such as an acyl chloride of general formula (VIII), wherein $R_1$ is as defined in general formula (I), by heating in solvents like dioxane in the presence of a basic reagent like calcium hydroxide.

Scheme 4

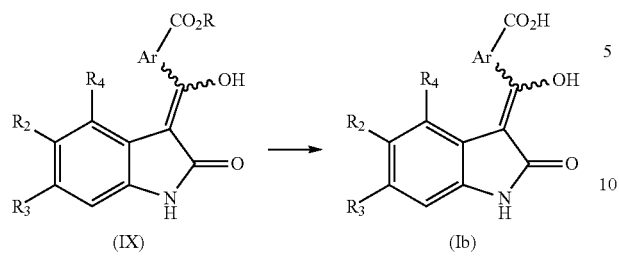

Oxindoles of general formula (Ib) corresponding to compounds of general formula (I), wherein R₁ represents an aryl group substituted with a carboxylic group (Ar—CO₂H), R₂, R₃ and R₄ are as defined in general formula (I) can be prepared according to Scheme 4 by treatment of a compound of general formula (IX), wherein R₂, R₃ and R₄ are as defined in the general formula (I) and R is an alkyl group such as a methyl or an ethyl group, with a basic reagent such as sodium hydroxide or lithium hydroxyde in an alcohol solvent like methanol or ethanol. Compounds of general formula (IX) can be prepared as described in Schemes 1 or 3.

Scheme 5

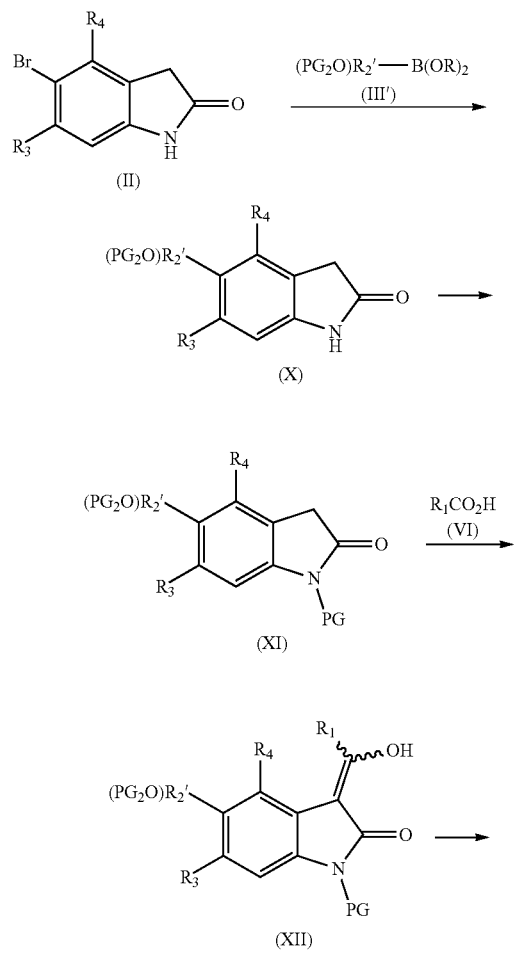

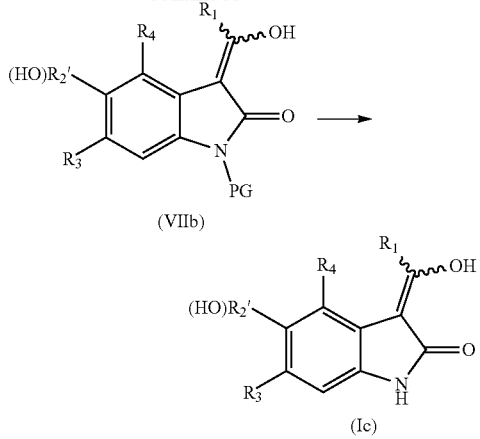

Oxindoles of general formula (Ic) corresponding to compounds of general formula (I), wherein R₂ represents a group R₂' substituted with at least a hydroxy group [i.e (OH)R₂'], wherein R₂' is an aryl group substituted with an aryl group, R₁, R₃ and R₄ are as defined in general formula (I) can be prepared as described in Scheme 5. 5-bromo-oxindoles of general formula (II) wherein R₃ and R₄ are as defined in general formula (I), and boron derivatives of general formula (III') can be coupled using palladium catalysts, such as PddppfCl₂ or tetrakistriphenylphosphine palladium at temperatures ranging from 25° C. to 130° C. with conventional heat or microwave heat for 30 minutes to 24 hours to provide compounds of general formula (X). In compounds of formula (III'), R₂' represents an aryl group substituted with an aryl group substituted with at least an hydroxy group, the said hydroxy group being protected with a PG₂ group, such as a silyl ether and B(OR)₂ being a boronic acid or boronate ester.

Compounds of general formula (X) can be treated with protecting reagents such as acetyl chloride, Boc₂O or the like to provide oxindoles of general formula (XI). Oxindoles of general formula (XI) can be acylated with a variety of carboxylic acid derivatives (VI), wherein R₁ is as defined in the general formula (I). The reaction can be carried out in solvents like DMF in the presence of an activating agent such as TBTU to provide compounds of general formula (XII). Removal of the protective group PG₂ can be performed with different reagents, for example if the protective group is a silyl moiety, acidic reagents or a fluoride reagent can be used to provide compounds of general formula (VIIb). Subsequent deprotection of the oxindole protecting group can be performed with a variety of acidic or basic reagents such as hydrogen chloride in dioxane or other solvents, trifluoroacetic acid, sodium hydroxyde in an alcohol solvent like ethanol or methanol to provide compounds of general formula (Ic).

Scheme 6

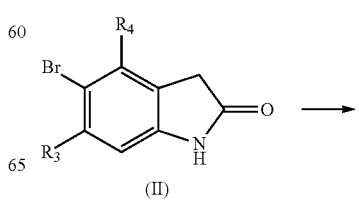

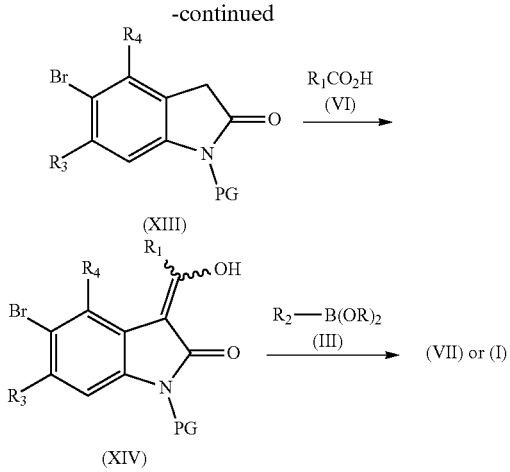

Intermediates (VII), wherein $R_1$, $R_2$, $R_3$ and $R_4$ are as defined above can also be synthesized according to Scheme 6. Compounds of general formula (II) can be treated with protecting reagents such as acetyl chloride, $Boc_2O$ or the like to provide oxindoles of general formula (XIII). Intermediates (XIII) can be acylated with a variety of carboxylic acids derivatives (VI) (wherein $R_1$ is as defined in the general formula I). The reaction can be carried out in solvents like dimethylformamide in the presence of coupling reagents like TBTU to provide compounds of general formula (XIV). Intermediates (XIV) and boron derivatives of general formula (III), wherein $R_2$ is as defined in general formula I and $B(OR)_2$ is a boronic acid or a boronate, can be coupled using palladium catalysts such as $PddppfCl_2$ or tetrakistriphenylphosphine palladium, at temperatures ranging from 25° C. to 130° C. with conventional heat or microwave heat for 30 minutes to 24 hours to provide compounds of general formula (VII) or directly compounds of general formula (I) depending on coupling conditions. Deprotection of intermediate (VII) is described in Scheme 1.

The following examples describe the preparation of some compounds corresponding to the invention. These examples are not restrictive and are not only illustrating the present invention. The numbers of the exemplified compounds send back to those given in the tables which illustrate the chemical structures and the physical properties of some compounds according to the invention.

Abbreviations and units used in the examples that follow are:
ACN: acetonitrile
° C.: Celsius degree
DTT: dithiothreitol
DMF: dimethylformamide
DMSO: dimethylsulfoxide
HCOOH: formic acid
TFA: trifluoroacetic acid
Eq: equivalent
ESI: electrospray Ionization
g: gram
NMR: nuclear magnetic resonance
h: hour
min: minute
HPLC: high performance liquid chromatography
Hz: Hertz
M: mass
MHz: megahertz
mL: millilitre
mmol: millimole
$PddppfCl_2$: [1,1'Bis(diphenylphosphino)ferrocene]dichloropalladium(II), complex with dichloromethane
N: normal
M: molar
nM: nanomolar
ppm: parts per millions
THF: tetrahydrofuran
$t_R$: retention time
UPLC: ultra-pressure liquid chromatography
UV: ultra-violet
%: percentage
RT: room temperature
DMAP: 4-dimethylaminopyridine
TBTU: O-(Benzotriazol-1-yl)-N,N,N',N'-tetramethyluronium tetrafluoroborate
$Boc_2O$: di-tert-butyl dicarbonate
AcOEt: ethyl acetate Proton nuclear magnetic resonance spectra ($^1H$ NMR) were recorded at 400 MHz in DMSO-$d_6$, using DMSO-d5 signal as reference. Chemical deplacement δ were expressed in ppm. The observed signals were expressed as following: s=singlet; d=doublet; t=triplet; m=massif or broad singlet.

In the table of examples the peak $(M+H)^+$ identified by mass spectrometry as well as the retention time ($t_R$) are indicated.

Compounds are analyzed by UPLC from Waters equipped with UV detector (220 nM) coupled with a mass spectrometer SQD2 from Waters using electrospray ionization (Method A). The analytical method is detailed below.

Column Acquity BEH C18 (50×2.1 mm; 1.7 µm) or equivalent (Acquity Cortex C18+, 50×2.1 mm; 1.6 µM)

Flow: 1.0 mL/min–T°=45° C.–injection 1 µL.

Gradient from 2% to 100% ACN with 0.1% HCOOH in water with 0.1% HCOOH in 2.6 min.

The intermediates are preferentially analysed using UPLC/SQD2 (ESI) apparatus from Waters equipped with a UV detector (220 nm) and a column Acquity UPLC BEH C18 (50×2.1 mm; 1.7 µm) eluted with a gradient of 5% to 99% ACN with 0.1% TFA in water with 0.1% TFA in 2.5 min (method B).

EXAMPLE 1

6-Chloro-5-(4-dimethylamino-phenyl)-3-[1-hydroxy-1-(3-methyl-isoxazol-5-yl) methylidene]-1,3-dihydro-indol-2-one

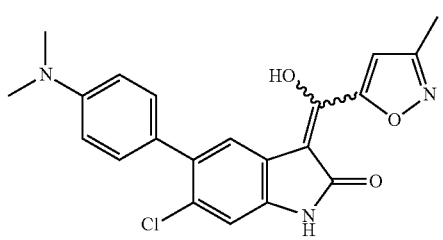

Step 1.1: 6-Chloro-5-(4-dimethylamino-phenyl)-2-oxo-2,3-dihydro-indole

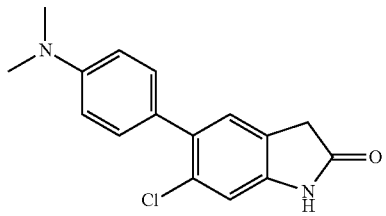 [SMILES: CN(C)c1ccc(-c2cc3c(cc2Cl)NC(=O)C3)cc1]

To a suspension of N,N-dimethyl-4-(4,4,5,5-tetramethyl-1,3,2-dioxaborolan-2-yl)aniline (1.1 g, 4.45 mmol) and 5-bromo-6-chloroindolin-2-one (0.8 g, 3.25 mmol) in toluene (6 mL) and ethanol (3 mL), aqueous $Na_2CO_3$ 2N (3.25 ml, 6.49 mmol) was added in one portion and the reaction mixture was degassed with nitrogen during 10 minutes. $PdCl_2(dppf).CH_2Cl_2$ (0.13 g, 0.16 mmol) was added and the resulting mixture was heated for 1 h at 130° C. in a microwave oven. The reaction mixture was diluted with AcOEt (65 mL) and water (65 mL) and the precipitate was filtered and rinsed with AcOEt (35 mL) and THF (5 mL). Organic layer was separated and washed with water (2×20 mL) and concentrated under reduced pressure to give a brown paste. The remaining crude product was purified by flash chromatography using a gradient $CH_2Cl_2/MeOH/NH_3$ [100/0/0 to 98/2/0.2]. The resulting orange powder was triturated with ACN, filtered, rinsed with $Et_2O$ and dried under vacuum ($P_2O_5$) to obtain 6-chloro-5-(4-dimethylamino-phenyl)-2-oxo-2,3-dihydro-indole (0.263 g, 28% yield).

LCMS (method B) $(M+H)^+=287$, $t_R=1.13$ min.

Step 1.2: 6-Chloro-5-(4-dimethylamino-phenyl)-2-oxo-2,3-dihydro-indole-1-carboxylic acid tert-butyl ester

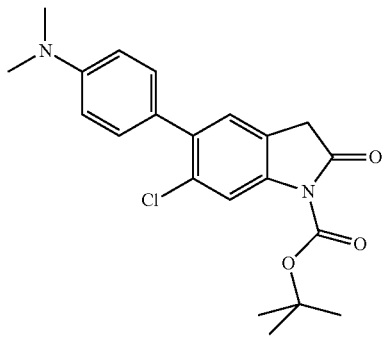 [SMILES: CN(C)c1ccc(-c2cc3c(cc2Cl)N(C(=O)OC(C)(C)C)C(=O)C3)cc1]

To a suspension of 6-chloro-5-(4-(dimethylamino)phenyl)indolin-2-one (1.58 g, 5.51 mmol), triethylamine (0.77 mL, 5.51 mmol) in THF (75 mL) was added di-tert-butyl dicarbonate (1.50 g, 6.61 mmol) in one portion under nitrogen atmosphere and stirring was continued for 30 min at room temperature. DMAP (0.033 g, 0.28 mmol), THF (20 mL) and DMF (2 mL) were added. Stirring was continued for 3 h at RT. The reaction mixture was diluted with $CH_2Cl_2$, washed with saturated aqueous $NaHCO_3$ and $H_2O$, dried over $MgSO_4$ and concentrated under vacuum. The residue was purified by flash chromatography using a gradient of ethyl acetate in heptane to provide 6-chloro-5-(4-dimethylamino-phenyl)-2-oxo-2,3-dihydro-indole-1-carboxylic acid tert-butyl ester (1.1 g, 51% yield).

LCMS (method B) $(M+H)^+=386$, $t_R=2.01$ min.

Step 1.3: 6-Chloro-5-(4-dimethylamino-phenyl)-3-[1-hydroxy-1-(3-methyl-isoxazol-5-yl)-methylidene]-2-oxo-2,3-dihydro-indole-1-carboxylic acid tert-butyl ester

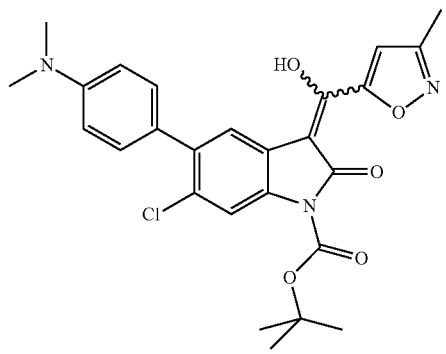

3-methylisoxazole-5-carboxylic acid (0.42 g, 3.13 mmol), tert-butyl 6-chloro-5-(4-(dimethylamino)phenyl)-2-oxoindoline-1-carboxylate (1.1 g, 2.84 mmol), TBTU, (1.02 g, 3.13 mmol) and triethylamine (1.98 mL, 14.22 mmol) were subsequently introduced into DMF (15 mL) and stirred at room temperature overnight. The reaction mixture was diluted with AcOEt (30 mL), washed with brine, dried over $MgSO_4$, concentrated under reduced pressure and further purified by flash chromatography using a gradient of methanol in dichloromethane to obtain a brownish foam which was precipitated in methanol (5 mL) to provide 6-chloro-5-(4-dimethylamino-phenyl)-3-[1-hydroxy-1-(3-methyl-isoxazol-5-yl)-methylidene]-2-oxo-2,3-dihydro-indole-1-carboxylic acid tert-butyl ester (0.80 g, 56% yield) as a yellow solid.

LCMS (method B) $(M+H)^+=496$, $t_R=2.20$ min.

Step 1.4: 6-Chloro-5-(4-dimethylamino-phenyl)-3-[1-hydroxy-1-(3-methyl-isoxazol-5-yl)-methylidene]-2-oxo-2,3-dihydro-indole (Example 1)

A solution of tert-butyl 6-chloro-5-(4-(dimethylamino)phenyl)-3-(hydroxy(3-methylisoxazol-5-yl)methylene)-2-oxoindoline-1-carboxylate (0.95 g, 1.91 mmol) in $CH_2Cl_2$ (10 mL) was cooled to 0° C. and trifluoroacetic acid (1 mL) was added drop wise. The solution was stirred for 3 h at room temperature and kept at 4° C. overnight to complete deprotection. The mixture was concentrated under vacuum without heating, diluted with AcOEt (100 mL) and poured into icecold saturated aqueous $NaHCO_3$. The separated organic layer is washed with saturated aqueous $NaHCO_3$ and brine, dried over $MgSO_4$, filtrated and concentrated under reduced pressure to obtain 0.3 g of a brown solid. The $MgSO_4$-filtercake is solubilized in water, exposed for 3 min in an ultrasonic bath at room temperature and filtrated to obtain further 0.4 g of a yellow solid. These two batches are suspended in water (100 mL) and acidified with an aqueous $SO_2$ solution (pH=2), stirred for 20 min, filtered and rinsed thoroughly with water to provide after drying 6-chloro-5-

(4-dimethylamino-phenyl)-3-[1-hydroxy-1-(3-methyl-isoxazol-5-yl)-methylidene]-2-oxo-2,3-dihydro-indole (0.7 g, 92% yield) as a yellow solid.

LCMS (method A) (M+H)$^+$=396, $t_R$=1.22 min.

1H NMR (400 MHz, DMSO-d$_6$) δ ppm 2.34 (s, 3 H) 2.95 (s, 6 H) 6.80 (d, J=8.78 Hz, 2 H) 7.01-7.10 (m, 1 H) 7.24 (d, J=8.53 Hz, 3 H) 7.81-8.07 (m, 1 H) 11.03-11.60 (m, 1 H).

EXAMPLE 2

6-Chloro-5-(4-dimethylamino-phenyl)-3-[1-hydroxy-1-(3-methyl-isoxazol-5-yl)-methylidene]-2-oxo-2,3-dihydro-indole, Na salt

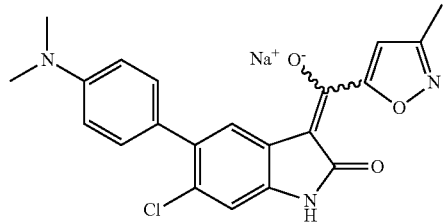

6-Chloro-5-(4-dimethylamino-phenyl)-3-[1-hydroxy-1-(3-methyl-isoxazol-5-yl)-methylidene]-2-oxo-2,3-dihydro-indole (0.5 g, 1.26 mmol) was suspended in methanol (15 mL). 1M NaOH (1.26 mL, 1.26 mmol) are added rapidly and stirring is continued for 1 h. Concentration under vacuum without heating and drying under reduced pressure provided 6-chloro-5-(4-dimethylamino-phenyl)-3-[1-hydroxy-1-(3-methyl-isoxazol-5-yl)-methylidene]-2-oxo-2,3-dihydro-indole, Na salt (0.51 g) as an ochre-coloured solid.

LCMS (method A) (M+H)$^+$=396, $t_R$=1.22 min.

EXAMPLE 3

6-Chloro-3-(hydroxy(3-hydroxyphenyl)methylene)-5-(4-morpholinophenyl)indolin-2-one

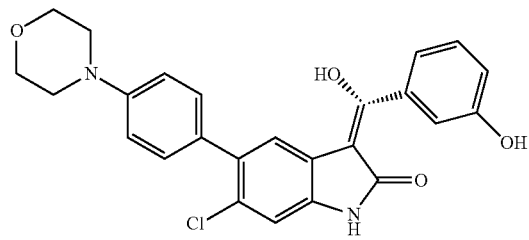

Step 3.1:
6-chloro-5-(4-morpholinophenyl)indolin-2-one

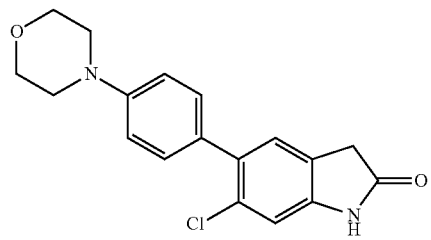 [SMILES: O=C1Cc2cc(-c3ccc(N4CCOCC4)cc3)c(Cl)cc2N1]

[1,1'bis(diphenylphosphino)ferrocene]dichloropalladium (II), complex with dichloromethane (0.13 g, 0.16 mmol) was added under nitrogen atmosphere to a suspension of 5-bromo-6-chloroindolin-2-one (0.8 g, 3.25 mmol), 4-morpholinophenylboronic acid (1.03 g, 4.87 mmol), aqueous Na$_2$CO$_3$ 2N (3.25 mL, 6.5 mmol) in ethanol (3 mL) and toluene (6 mL). This process is repeated ten times. The resulting mixture was heated under microwave irradiation at 130° C. for 1 hour. The collected crude material was washed with water (200 mL) and ethyl acetate (100 mL). The brown solid was filtrated off and washed with water and ethyl acetate. The resulting solid was heated in acetonitrile (50 mL) under reflux, filtrated off and washed with acetonitrile (10 ml). The brown solid was purified by flash chromatography using a gradient of methanol in dichloromethane to yield 6-chloro-5-(4-morpholinophenyl)indolin-2-one (4.64 g, 44% yield).

LCMS (method B) (M+H)$^+$=329, $t_R$=1.28 min.

Step 3.2: tert-Butyl 6-chloro-5-(4-morpholinophenyl)-2-oxoindoline-1-carboxylate

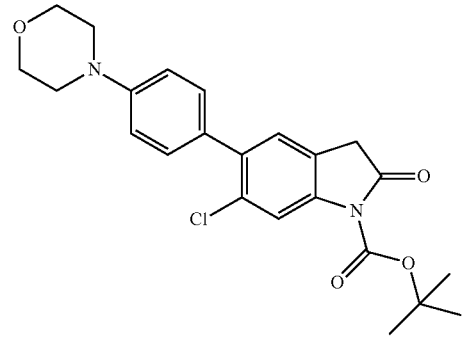 [SMILES: CC(C)(C)OC(=O)N1C(=O)Cc2cc(-c3ccc(N4CCOCC4)cc3)c(Cl)cc21]

To a solution of 6-chloro-5-(4-morpholinophenyl)indolin-2-one (3.3 g, 10.04 mmol) in tetrahydrofuran (100 ml) were added sodium bicarbonate (7.59 g, 90.33 mmol) and Boc$_2$O (2.80 ml, 12.04 mmol). The resulting mixture was stirred under reflux for 4 hours. Ethyl acetate was added and the mixture was washed with water and a brine solution and then dried over magnesium sulfate. After concentration under vacuum, the resulting solid was washed with ethyl ether to yield tert-butyl 6-chloro-5-(4-morpholinophenyl)-2-oxoindoline-1-carboxylate (2.16 g, 50% yield) as an orange powder.

LCMS (method B) (M+H)$^+$=429, $t_R$=1.92 min.

Step 3.3: tert-Butyl 6-chloro-3-(hydroxy(3-methoxyphenyl)methylene)-5-(4-morpholinophenyl)-2-oxoindoline-1-carboxylate

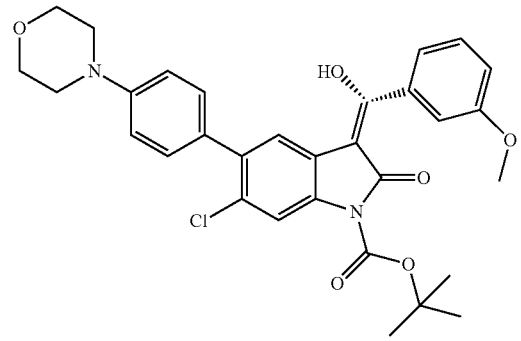

To a solution of 3-methoxybenzoic acid (0.11 g, 0.70 mmol), tert-butyl 6-chloro-5-(4-morpholinophenyl)-2-oxoindoline-1-carboxylate (0.30 g, 0.70 mmol) and triethylamine (0.49 mL, 3.50 mmol) in DMF (5 mL) was added TBTU (0.25 g, 0.77 mmol) at room temperature under nitrogen atmosphere. The resulting mixture is stirred for 4 hours. Ethyl acetate and water were added. The organic phase was dried over sodium sulfate and concentrated under vacuum. The remaining crude product was purified by flash chromatography using a gradient of methanol in dichloromethane. The resulting solid was washed with methanol to yield tert-butyl 6-chloro-3-(hydroxy(3-methoxyphenyl)methylene)-5-(4-morpholinophenyl)-2-oxoindoline-1-carboxylate (0.13 g, 33% yield).

LCMS (method B) (M+H)$^+$=563, $t_R$=2.39 min.

Step 3.4: 6-chloro-3-(hydroxy(3-hydroxyphenyl)methylene)-5-(4-morpholinophenyl) indolin-2-one (Example 3)

A mixture of tert-butyl 6-chloro-3-(hydroxy(3-methoxyphenyl)methylene)-5-(4-morpholinophenyl)-2-oxoindoline-1-carboxylate (0.049 mL, 0.087 mmol) in dichloromethane (2 mL) is cooled to 0° C. Boron tribromide (0.049 mL, 0.044 mmol) was added and the resulting mixture was stirred at room temperature for 2 hours. Additional boron tribromide (0.050 mL, 0.045 mmol) was added and the mixture was stirred for another hour. Ethyl acetate and water were added. The organic phase was dried over sodium sulfate and concentrated under vacuum. The resulting residue was crystallized in dichloromethane to yield 6-chloro-3-(hydroxy(3-hydroxyphenyl)methylene)-5-(4-morpholinophenyl)indolin-2-one (0.011 g, 28% yield).

LCMS (method A) (M+H)$^+$=449, $t_R$ 1.33 min.
1H NMR (400 MHz, DMSO-d$_6$) δ ppm 3.08-3.19 (m, 4 H) 3.70-3.81 (m, 4 H) 6.83-7.41 (m, 10 H) 9.79-9.91 (m, 1 H) 11.36-11.49 (m, 1 H)

EXAMPLE 4

{[6-Chloro-5-(4-morpholin-4-yl-phenyl)-2-oxo-1,2-dihydro-indolylidene]-hydroxy-methyl}-benzoic acid

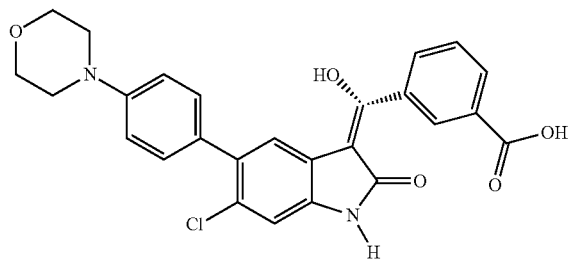

Step 4.1: 3-{[6-Chloro-5-(4-morpholin-4-yl-phenyl)-2-oxo-1,2-dihydro-indolylidene]-hydroxy-methyl}-benzoic acid methyl ester

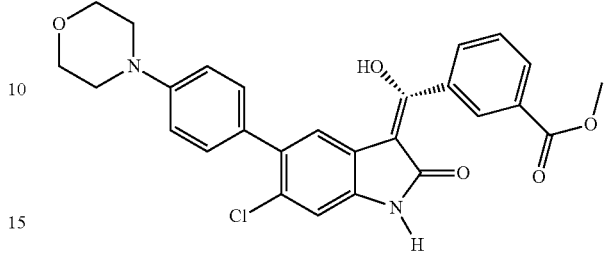

Calcium hydroxyde (0.069 g, 0.6 mmol) was added to a solution of 6-chloro-5-(4-morpholin-4-yl-phenyl)-1,3-dihydro-indol-2-one (intermediate 3.1) (0.2 g, 0.6 mmol) in 1,4-dioxane. The resulting suspension was refluxed for 4 h, then cooled at room temperature before adding methyl 3-(chloroformyl)benzoate (0.124 g, 0.6 mmol). The mixture was heated under reflux for 4 h, then methyl 3-(chloroformyl)benzoate (0.06 g, 0.3 mmol) was added. The mixture was additionally heated under reflux for 4 h, and then concentrated under vacuum. Water and a solution of hydrochloric acid were added. The resulting solid was filtered off, and then washed with water, ethanol and pentane to yield 3-{[6-Chloro-5-(4-morpholin-4-yl-phenyl)-2-oxo-1,2-dihydro-indolylidene]-hydroxy-methyl}-benzoic acid methyl ester (0.1 g, 32% yield) which was used in the following reaction without further purification.

LCMS (method B) (M+H)$^+$=491, $t_R$=1.84 min.

Step 4.2: -{[6-Chloro-5-(4-morpholin-4-yl-phenyl)-2-oxo-1,2-dihydro-indolylidene]-hydroxy-methyl}-benzoic acid (Example 4)

Lithium hydroxide (0.01 g, 0.407 mmol) was added to a suspension of 3-{[6-chloro-5-(4-morpholin-4-yl-phenyl)-2-oxo-1,2-dihydro-indolylidene]-hydroxy-methyl}-benzoic acid methyl ester (0.1 g, 0.203 mmol) in water (2 mL) and methanol (2 mL). Tetrahydrofurane (3 mL) was added, and the resulting mixture was stirred for 20 h at room temperature. Lithium hydroxide (0.01 g, 0.407 mmol) was added, and the mixture was additionally stirred for 24 h, and then concentrated under vacuum. Water and a 6% aqueous solution of sulphur dioxide were added up to pH=1. The resulting solid was filtered off, and then washed with water to yield 3-{[6-Chloro-5-(4-morpholin-4-yl-phenyl)-2-oxo-1,2-dihydro-indolylidene]-hydroxy-methyl}-benzoic acid (0.021 g, 22% yield) as a yellow powder.

LCMS (method A) (M+H)$^+$=477, $t_R$=1.05 min.
1H NMR (400 MHz, DMSO-d$_6$) δ ppm: 2.98-3.23 (m, 4 H) 3.69-3.82 (m, 4 H) 6.80-7.39 (m, 6 H) 7.50-8.56 (m, 5 H) 11.27-11.67 (m, 1 H) 12.92-13.74 (m, 1 H)

EXAMPLE 5

6-Chloro-5-(2'-hydroxy-3'-methoxy-biphenyl-4-yl)-3-[1-hydroxy-1-(3-methyl-isoxazol-5-yl)-methylidene]-1,3-dihydro-indol-2-one

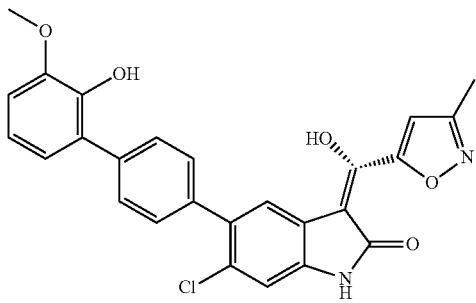

Step 5.1: 1,4-bis(4,4,5,5-tetramethyl-1,3,2-dioxaborolan-2-yl)benzene

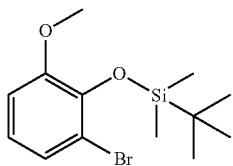 [SMILES: COc1cccc(Br)c1O[Si](C)(C)C(C)(C)C]

2-bromo-6-methoxyphenol (5 g, 24.6 mmol), tert-butyldimethylchlorosilane (4.08 g, 27.1 mmol) and imidazole (1.79 g, 26.4 mmol) were stirred under nitrogen at room temperature for 6 h in anhydrous $CH_2Cl_2$ (30 mL). To the white suspension were added $CH_2Cl_2$ (50 mL) and the mixture was washed with HCl 1N (2×30 ml) and $H_2O$ (30 mL). The aqueous phase was extracted with $CH_2Cl_2$ (30 mL), the combined organic layers were dried over $MgSO_4$, filtered and concentrated under reduced pressure without heating to obtain 1,4-bis(4,4,5,5-tetramethyl-1,3,2-dioxaborolan-2-yl)benzene (7.8 g, 99% yield) as a colourless oil.

LCMS (method B) observed $(M+H)^+=296$, $t_R=2.44$ min.

Step 5.2: 2-[2'-(tert-Butyl-dimethyl-silanyloxy)-3'-methoxy-biphenyl-4-yl]-4,4,5,5-tetramethyl-[1,3,2]dioxaborolane

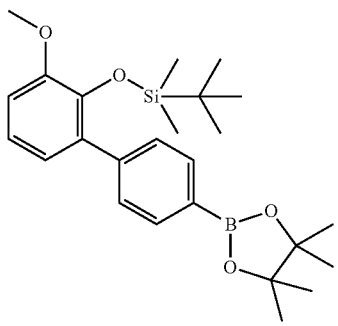 [SMILES: COc1cccc(-c2ccc(B3OC(C)(C)C(C)(C)O3)cc2)c1O[Si](C)(C)C(C)(C)C]

Into a 0.5 three necked flasked equipped with a reflux condenser, thermometer and a nitrogen inlet were subsequently introduced to a solvent mixture of dioxane (135 mL) and of $H_2O$ (45 mL), 2-bromo-6-methoxy-phenoxy-tert-butyldimethylsilane (7.379 g, 23.3 mmol), 1,4-bis(4,4,5,5-tetramethyl-1,3,2-dioxaborolan-2-yl)benzene (14.39 g, 41.9 mmol), 2,6-di-tert-butyl-4-methylphenol (5.12 g, 23.3 mmol), tricyclohexylphosphine (0.261 g, 0.93 mmol) and $K_2CO_3$ (9.64 g). This white suspension was degassed during 10 min with nitrogen, $Pd_2(dba)_3$ (0.43 g, 0.47 mmol) was added and the mixture was heated to reflux for 2 hours. Once cooled to room temperature the mixture was poured into water (200 mL), acidified to pH 1 with HCl 1 N and of AcOEt (250 mL) were added. The organic layer was washed twice with water (200 mL), the aqueous layer extracted once with AcOEt (100 mL) and the combined organic layers were filtered, dried over $MgSO_4$ and concentrated under reduced pressure to give 11 g of a crude yellow oil which was further purified by flash chromatography using a gradient of $CH_2Cl_2$ in heptane to provide 2-[2'-(tert-Butyl-dimethyl-silanyloxy)-3'-methoxy-biphenyl-4-yl]-4,4,5,5-tetramethyl-[1,3,2]dioxaborolane (6.3 g, 62% yield) as a white solid.

LCMS (method B) observed $(M+H)^+=454$, $t_R=2.66$ min.

Step 5.3: 5-[2'-(tert-Butyl-dimethyl-silanyloxy)-3'-methoxy-biphenyl-4-yl]-6-chloro-1,3-dihydro-indol-2-one In a 25 mL microwave vial were introduced tert-butyl-((3-methoxy-4'-(4,4,5,5-tetramethyl-1,3,2-dioxaborolan-2-yl)-[1,1'-biphenyl]-2-yl)oxy)dimethylsilane (2.14 g, 4.87 mmol), 5-bromo-6-chloroindolin-2-one (0.8 g, 3.25 mmol) in toluene (6 mL) and ethanol (3 mL) (brownish suspension). 2N aqueous $Na_2CO_3$ (3.25 ml, 6.49 mmol) was added in one portion and the reaction mixture was degassed with nitrogen during 10 minutes. $PdCl_2(dppf) \cdot CH_2Cl_2$ (0.133 g, 0.162 mmol) was added, the vial was dosed and heated for 1 h at 130° C. in a microwave oven. The reaction mixture was diluted with 20 mL AcOEt and 10 mL of water. The precipitate was filtered. The filter cake was washed with water, THF, acetonitrile, $CH_2Cl_2$ and methanol to obtain 0.66 g of a crude grey colored product. Final purification on silica gel column (gradient $CH_2Cl_2$/MeOH 100/0 to 97.2/2.5 in 20 minutes) provided 5-[2'-(tert-Butyl-dimethyl-silanyloxy)-3'-methoxy-biphenyl-4-yl]-6-chloro-1,3-dihydro-indol-2-one (0.49 g, 32% yield) as a white solid.

LCMS (method B) $(M+H+ACN)^+=521$, $(M+H)^+=480$ (low intensity peak), $t_R=2.34$ min.

Step 5.4: 5-[2'-(tert-Butyl-dimethyl-silanyloxy)-3'-methoxy-biphenyl-4-yl]-6-chloro-2-oxo-2,3-dihydro-indole-1-carboxylic acid tert-butyl ester

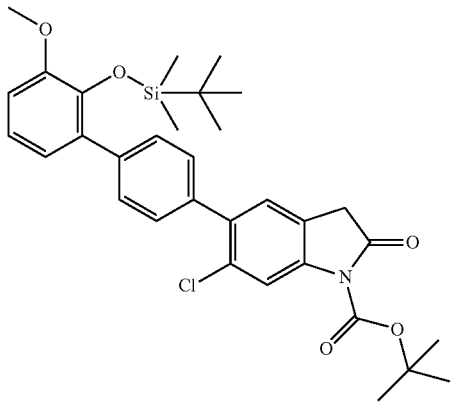 [SMILES: COc1cccc(-c2ccc(-c3cc4c(cc3Cl)N(C(=O)OC(C)(C)C)C(=O)C4)cc2)c1O[Si](C)(C)C(C)(C)C]

In a 250 mL round bottomed flask under inert atmosphere were suspended 5-(2'-((tert-butyldimethylsilyl)oxy)-3'-methoxy-1',2'-dihydro-[1,1'-biphenyl]-4-yl)-6-chloroindolin-2-one (1.2 g, 2.49 mmol) in anhydrous THF (50 mL). $Na_2CO_3$ (1.88 g, 22.40 mmol) and $Boc_2O$ (0.717 g, 2.74 mmol) were added in one portion respectively.

The mixture was refluxed for 3 h. The reaction mixture was poured onto 30 mL AcOEt and 30 mL of water, the organic layer was separated, washed with brine and dried over $MgSO_4$. Concentration under reduced pressure provided 5-[2'-(tert-Butyl-dimethyl-silanyloxy)-3'-methoxy-biphenyl-4-yl]-6-chloro-2-oxo-2,3-dihydro-indole-1-carboxylic acid tert-butyl ester (1.35 g, 93% yield) as an orange solid.

LCMS (method B) $(M+ACN+Na)^+=579+23+41=643$ observed, $t_R=2.72$ min.

Step 5.5: 5-[2'-(tert-Butyl-dimethyl-silanyloxy)-3'-methoxy-biphenyl-4-yl]-6-chloro-3-[1-hydroxy-1-(3-methyl-isoxazol-5-yl)-methylidene]-2-oxo-2,3-dihydro-indole-1-carboxylic acid tert-butyl ester

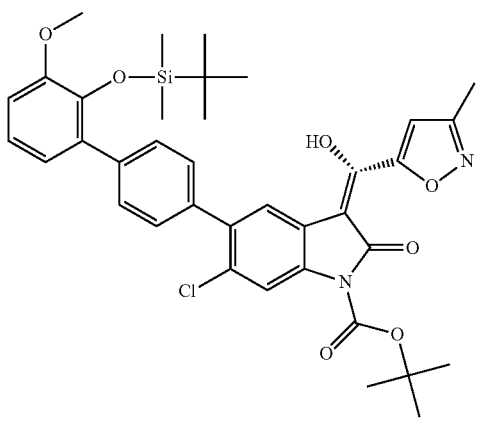

Into a 25 mL round-bottomed flask under nitrogen were introduced DMF (3 mL), 3-methylisoxazole-5-carboxylic acid (0.1015 g, 0.758 mmol), tert-butyl 5-(2'-((tert-butyldimethylsilyl)oxy)-3'-methoxy-[1,1'-biphenyl]-4-yl)-6-chloro-2-oxoindoline-1-carboxylate (0.4 g, 0.689 mmol), triethylamine (0.48 mL, 3.45 mmol) to obtain a brownish suspension. TBTU (0.248 g, 0.758 mmol) was added in one portion and the mixture was stirred for 4 h at room temperature. 10 mL AcOEt were added, the organic layer was washed with saturated aqueous $NaHCO_3$ solution and water, dried over $MgSO_4$ and concentrated under vacuum. The crude mixture was purified on silica gel (gradient $CH_2Cl_2$/MeOH 100/0 to 95/5 during 30 min) to provide 5-[2'-(tert-butyl-dimethyl-silanyloxy)-3'-methoxy-biphenyl-4-yl]-6-chloro-3-[1-hydroxy-1-(3-methyl-isoxazol-5-yl)-methylidene]-2-oxo-2,3-dihydro-indole-1-carboxylic acid tert-butyl ester (0.39 g, 81% yield) as a yellow solid.

LCMS (method B), no M+ detected, $t_R=2.91$ min.

Step 5.6: 6-Chloro-5-(2'-hydroxy-3'-methoxy-biphenyl-4-yl)-3-[1-hydroxy-1-(3-methyl-isoxazol-5-yl)-methylidene]-2-oxo-2,3-dihydro-indole-1-carboxylic acid tert-butyl ester

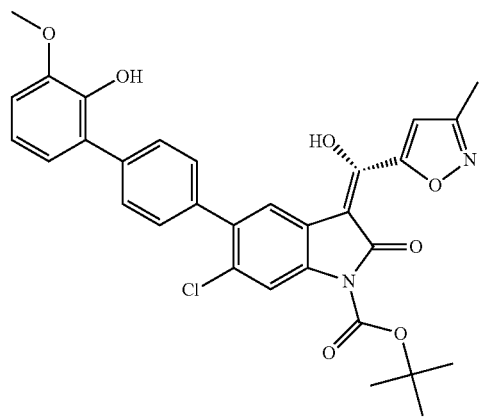

Into a 100 mL round-bottomed flask tert-butyl 5-(2'-((tert-butyldimethylsilyl)oxy)-3'-methoxy-[1,1'-biphenyl]-4-yl)-6-chloro-3-(hydroxy(3-methylisoxazol-5-yl)methylidene)-2-oxoindoline-1-carboxylate (0.31 g, 0.450 mmol) were solubilized in 5 mL THF (yellow solution). 0.9 mL (0.9 mmol) of an 1N solution of TBAF in THF were added slowly and the mixture was stirred at room temperature for 5 hours. The reaction mixture was poured into 15 mL AcOEt, washed with water, dried over $MgSO_4$ and concentrated under reduced pressure. The crude gummy material was triturated in 5 mL of an ether/pentane 1/1 mixture, solvents were decanted and 0.26 g (quantitative yield) of a yellow-green foam were obtained under reduced pressure.

Step 5.7: 6-Chloro-5-(2'-hydroxy-3'-methoxy-biphenyl-4-yl)-3-[1-hydroxy-1-(3-methyl-isoxazol-5-yl)-methylidene]-1,3-dihydro-indol-2-one (Example 5)

In a 25 mL round-bottomed flask tert-butyl-6-chloro-3-(hydroxy(3-methylisoxazol-5-yl)methylene)-5-(2'-hydroxy-3'-methoxy-[1,1'-biphenyl]-4-yl)-2-oxoindoline-1-carboxylate (0.220 g, 0.383 mmol) were solubilized in 4 mL of 4N HCl in dioxane (brown solution) and stirred for two hours at room temperature, a slight precipitate appears. 15 mL of $CH_2Cl_2$ were added; the organic layer was washed with water, dried over $MgSO_4$ and concentrated under reduced pressure to obtain a brownish oil which was crystallized by adding water. After filtration and drying under reduced pressure (P₂O₅) 0.114 g (63% yield) of a green solid were isolated.

LCMS (method A) (M+H)⁺=475, $t_R$=1.71 min.

1H NMR (400 MHz, DMSO-d₆) δ ppm: 2.34 (s, 3 H) 3.86 (s, 3 H) 6.83-7.03 (m, 3 H) 7.06-7.17 (m, 1 H) 7.20-7.29 (m, 1 H) 7.44 (d, J=8.28 Hz, 2 H) 7.63 (d, J=8.28 Hz, 2 H) 7.95-8.08 (m, 1 H) 8.54-8.72 (m, 1 H) 11.09-11.47 (m, 1 H)

EXAMPLE 6

6-Chloro-3-hydroxy(3-methylisoxazol-5-yl)methylene)-5-(4-(1-(hydroxymethyl)cyclopropyl)phenyl)indolin-2-one

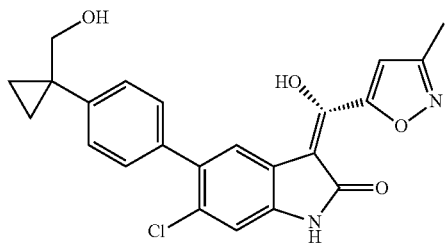

Step 6.1: tert-butyl 5-bromo-6-chloro-2-oxoindoline-1-carboxylate

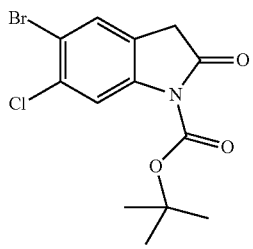 [SMILES: CC(C)(C)OC(=O)N1C(=O)Cc2cc(Br)c(Cl)cc21]

To a solution of 5-bromo-6-chloroindolin-2-one (7 g, 28.40 mmol) in tetrahydrofuran (200 mL) was added sodium bicarbonate (16.3 g, 192.09 mmol) and di-tert-butyl dicarbonate (6.89 g, 31.24 mmol). The resulting mixture was heated under reflux for 5 hours. After concentration under vacuum, ethyl acetate and water were added. The organic phase was dried over sodium sulfate and concentrated under vacuum to yield tert-butyl 5-bromo-6-chloro-2-oxoindoline-1-carboxylate (9.1 g, 94% yield) which was used in the following reaction without further purification.

LCMS (method B) (M+ACN+Na)⁺=410, $t_R$=1.92 min.

Step 6.2: tert-Butyl 5-bromo-6-chloro-3-(hydroxy(3-methylisoxazol-5-yl)methylene)-2-oxoindoline-1-carboxylate

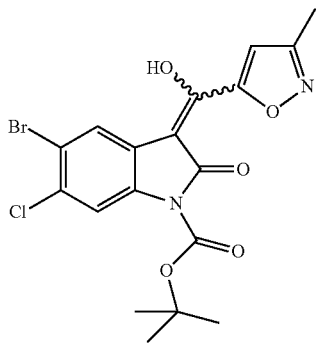

To a solution of tert-butyl 5-bromo-6-chloro-2-oxoindoline-1-carboxylate (2.99 g, 8.63 mmol), 3-methylisoxazole-5-carboxylic acid (1.27 g, 9.49 mmol) and TBTU (3.11 g, 9.49 mmol) in DMF (10 mL) was added triethylamine (6.01 ml, 43.13 mmol). The resulting mixture is stirred for 18 hours at room temperature. Dichloromethane and water were added. The organic phase was dried over magnesium sulfate and concentrated under vacuum. The remaining crude product was purified by flash chromatography using a gradient of ethyl acetate in dichloromethane to yield tert-butyl 5-bromo-6-chloro-3-(hydroxy(3-methylisoxazol-5-yl)methylene)-2-oxoindoline-1-carboxylate (3.02 g, 77% yield) as a yellow powder.

LCMS (method A) (M+H)⁺=455, $t_R$=1.48 min.

Step 6.3: 6-Chloro-3-(hydroxy(3-methylisoxazol-5-yl)methylene)-5-(4-(1-(hydroxymethyl)cyclopropyl)phenyl)indolin-2-one (Example 6)

4-(1-(Hydroxymethyl)cyclopropyl)phenylboronic acid (0.26 g, 1.32 mmol), aqueous sodium carbonate 2M (1.10 mL, 2.19 mmol) and [1,1'bis(diphenylphosphino)ferrocene]dichloropalladium(II), complex with dichloromethane (0.045 g, 0.055 mmol) were added under nitrogen atmosphere to a solution of tert-butyl 5-bromo-6-chloro-3-(hydroxy(3-methylisoxazol-5-yl)methylene)-2-oxoindoline-1-carboxylate (0.5 g, 1.10 mmol) in a mixture of ethanol (1.1 mL) and toluene (2.2 ml). The resulting mixture was stirred at 120° C. for 1 h in a microwave oven. After filtration and concentration under vacuum, ethyl acetate and water were added. The organic phase was dried over magnesium sulfate and concentrated under vacuum. The remaining crude product was purified by chromatography on a C₁₈ reverse phase using a gradient of acetonitrile in water. The resulting solid was washed with pentane to yield 6-chloro-3-(hydroxy(3-methylisoxazol-5-yl)methylene)-5-(4-(1-(hydroxymethyl)cyclopropyl)phenyl)indolin-2-one (0.14 g, 31% yield).

LCMS (method A) (M+H)⁺=423, $t_R$=1.19 min.

1H NMR (400 MHz, DMSO-d₆) d ppm: 0.76-0.91 (m, 4 H) 2.34 (s, 3 H) 3.56-3.61 (m, 2 H) 7.03-7.13 (m, 1 H) 7.21-7.28 (m, 1 H) 7.29-7.42 (m, 4 H) 7.90-8.00 (m, 1 H) 11.00-11.55 (m, 1 H)

Compounds of table 1 are synthetized according to methods outlined in schemes 1 to 6 and illustrated in examples 1 to 6.

TABLE 1

| Compound | Structure | Scheme | LC/MS data [M + H]+ T$_{R[min]}$ |
|---|---|---|---|
| 1 | 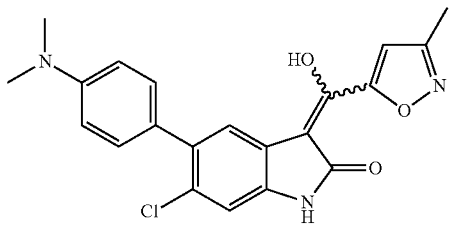 | 1 | 396 1.22 |
| 2 | Na+ | | 396 1.22 |
| 3 | 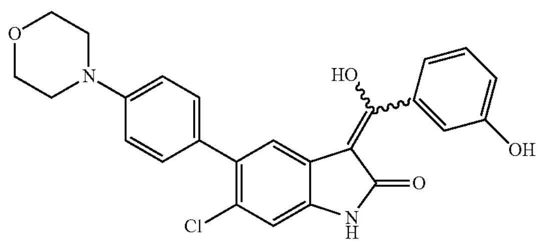 | 2 | 449 1.33 |
| 4 | 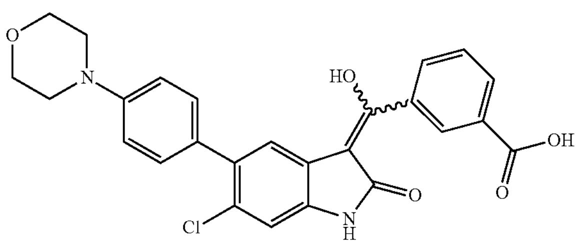 | 3 & 4 | 477 1.05 |
| 5 | 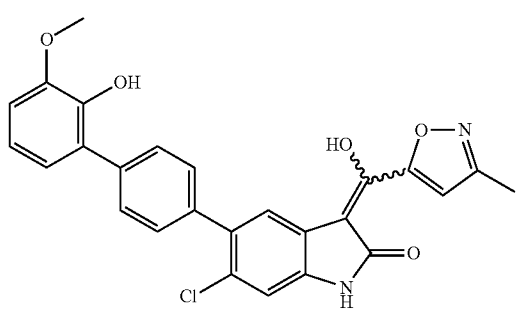 | 1 | 475 1.35 |
| 6 | 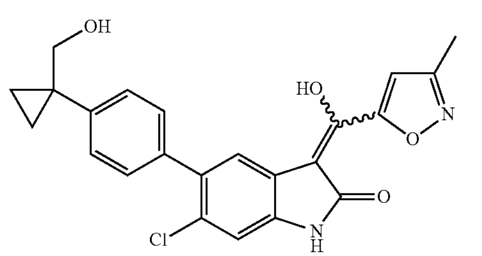 | 6 | 423 1.19 |

TABLE 1-continued

| Compound | Structure | Scheme | LC/MS data [M + H]+ $T_{R[min]}$ |
|---|---|---|---|
| 7 | 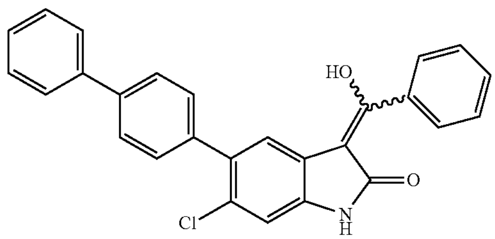 | 3 | 424 1.55 |
| 8 | 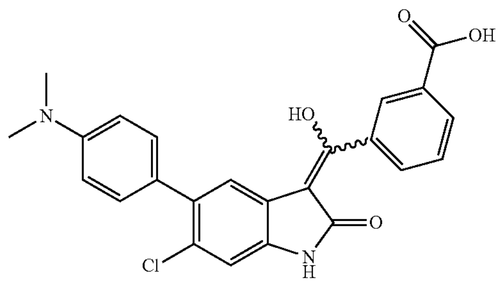 | 3 & 4 | 433 1.08 |
| 9 | 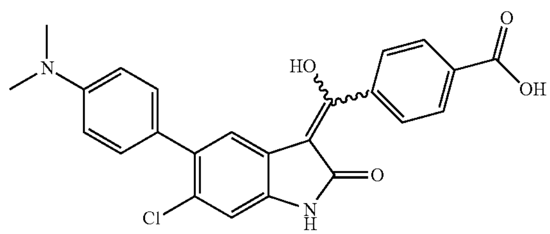 | 1 | 433 1.04 |
| 10 | 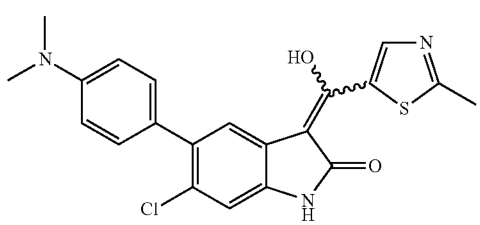 | 1 | 412 1.12 |
| 11 | 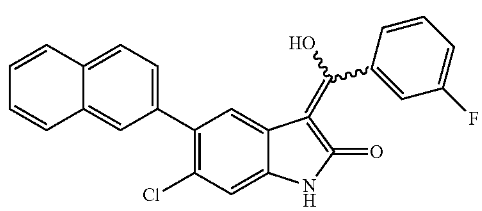 | 1 | 416 1.54 |
| 12 | 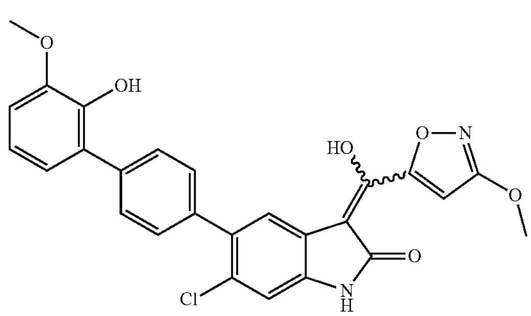 | 5 | 491 1.64 |

TABLE 1-continued

| Compound | Structure | Scheme | LC/MS data [M + H]+ T$_{R[min]}$ |
|---|---|---|---|
| 13 | 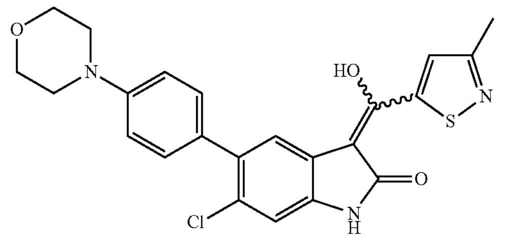 | 1 | 454 1.26 |
| 14 | 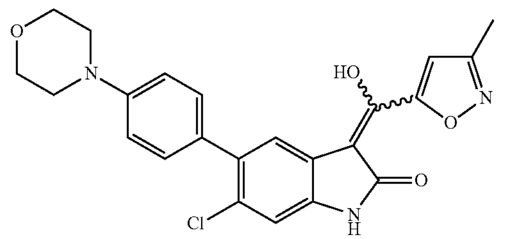 | 1 | 438 1.24 |
| 15 | 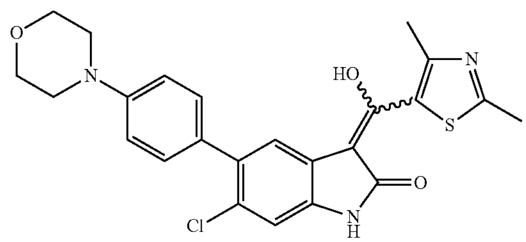 | 1 | 468 1.24 |
| 16 | 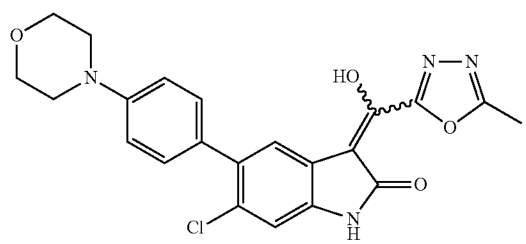 | 1 | 439 1.09 |
| 17 | 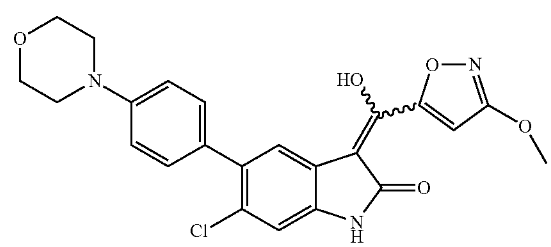 | 1 | 454 1.26 |
| 18 | 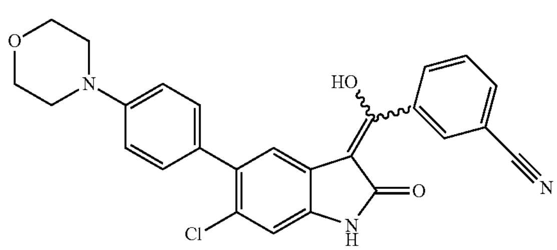 | 1 | 458 1.22 |

TABLE 1-continued

| Compound | Structure | Scheme | LC/MS data [M + H]+ T$_{R[min]}$ |
|---|---|---|---|
| 19 | 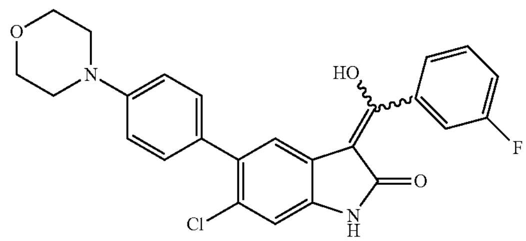 | 1 | 451 1.31 |
| 20 | 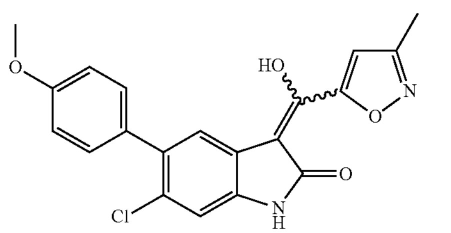 | 1 | 383 1.30 |
| 21 | 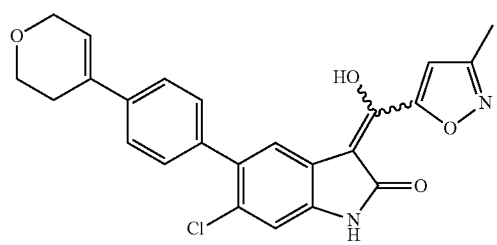 | 1 | 435 1.62 |
| 22 | 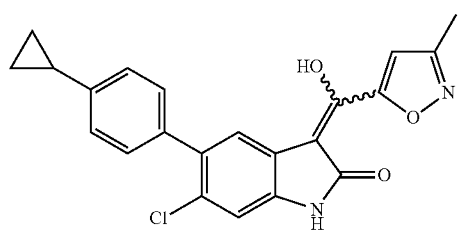 | 1 | 393 1.93 |
| 23 | 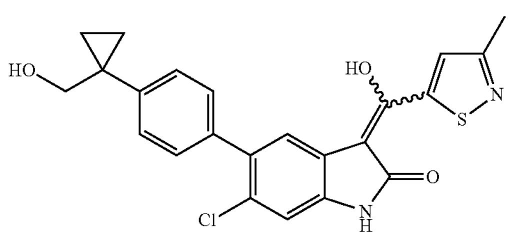 | 1 | 439 1.41 |
| 24 | 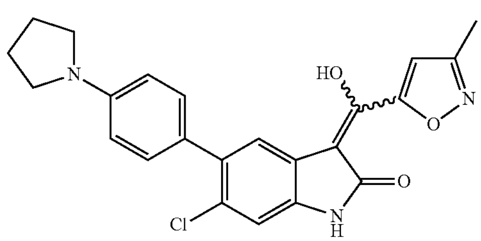 | 1 | 422 1.75 |

TABLE 1-continued

| Compound | Structure | Scheme | LC/MS data [M + H]+ T_R[min] |
|---|---|---|---|
| 25 | 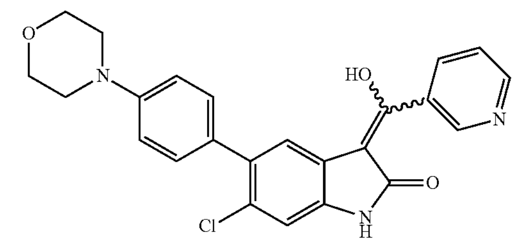 | 1 | 432 1.12 |
| 26 | 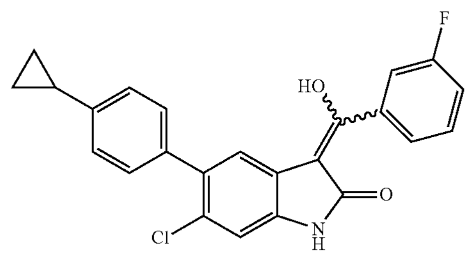 | 1 | 406 1.80 |
| 27 | 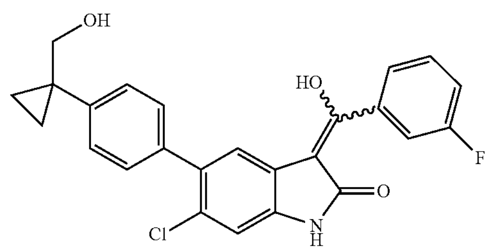 | 1 | 436 1.48 |
| 28 | 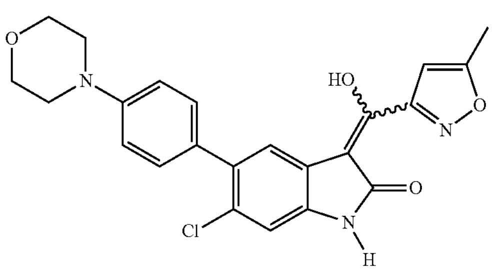 | 1 | 438 1.50 |
| 29 | 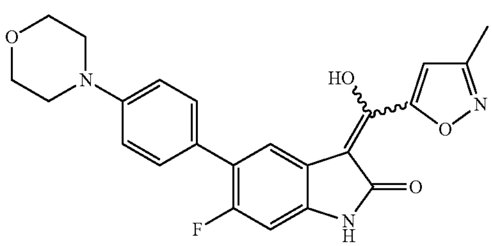 | 1 | 422 1.43 |
| 30 | 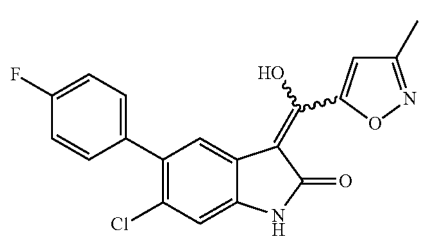 | 1 | 369 1.58 |

TABLE 1-continued

| Compound | Structure | Scheme | LC/MS data [M + H]+ T$_{R[min]}$ |
|---|---|---|---|
| 31 | 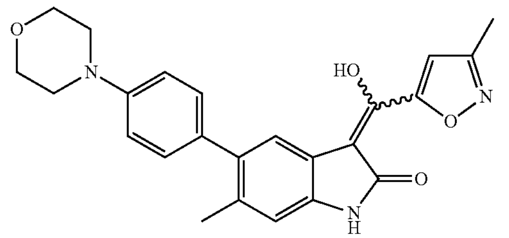 | 1 | 418 1.43 |
| 32 | 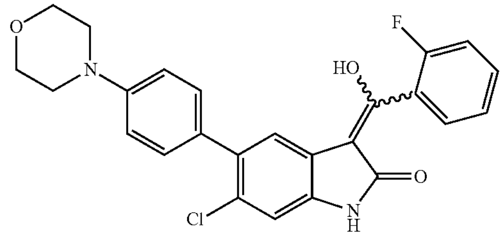 | 1 | 451 1.50 |
| 33 | 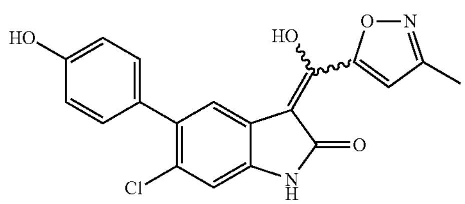 | 6 | 369 1.26 |
| 34 | 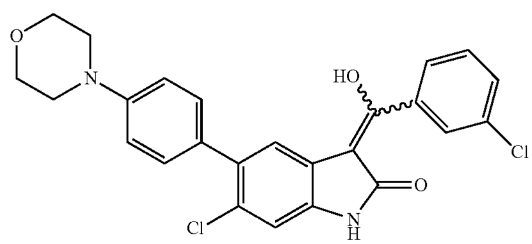 | 1 | 467 1.67 |
| 35 | 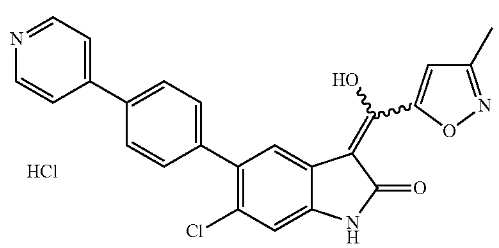 | 6 | 430 1.12 |
| 36 | 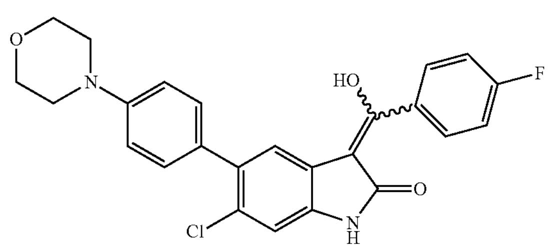 | 1 | 451 1.57 |

TABLE 1-continued

| Compound | Structure | Scheme | LC/MS data [M + H]+ T$_{R[min]}$ |
|---|---|---|---|
| 37 | 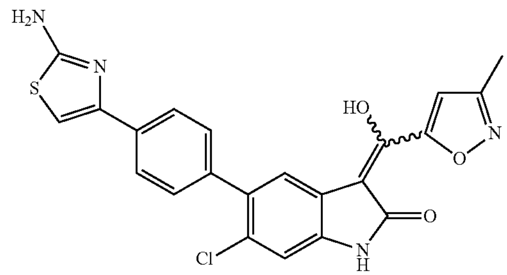 | 6 | 451 0.74 |
| 38 | 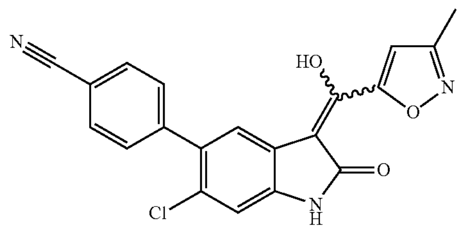 | 1 | 378 1.46 |
| 39 | 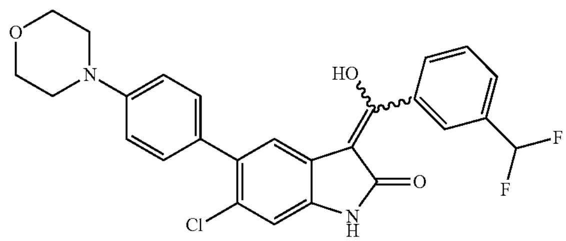 | 1 | 483 1.55 |
| 40 | 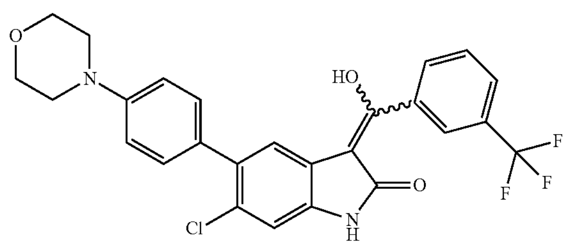 | 1 | 501 1.68 |
| 41 | 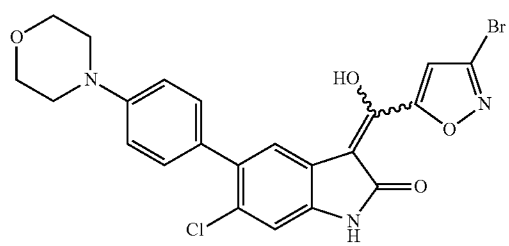 | 1 | 502 1.59 |
| 42 | 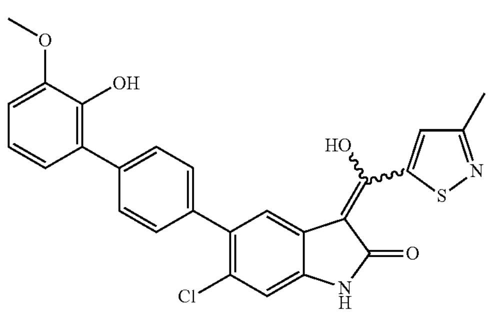 | 5 | 491 1.64 |

TABLE 1-continued

| Compound | Structure | Scheme | LC/MS data [M + H]+ T$_{R[min]}$ |
|---|---|---|---|
| 43 | 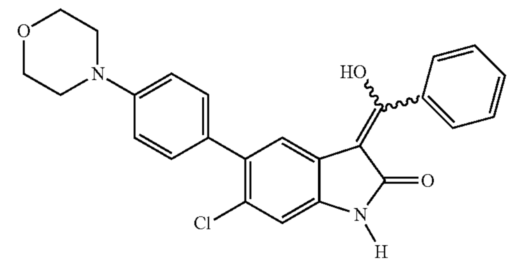 | 1 | 433 1.54 |
| 44 | 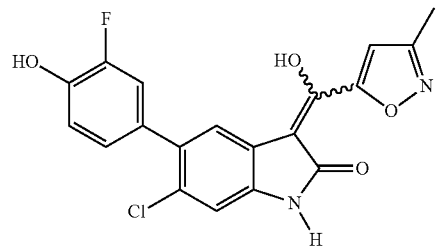 | 1 | 385 1.31 |
| 45 | 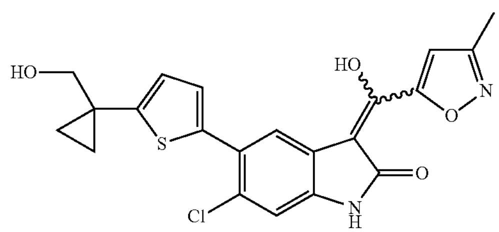 | 1 | 429 1.4 |
| 46 | 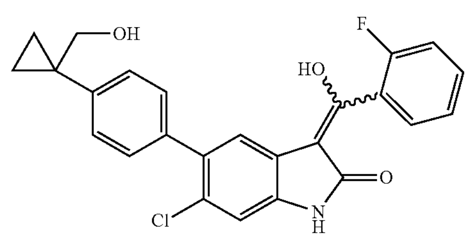 | 1 | 436 1.41 |
| 47 | 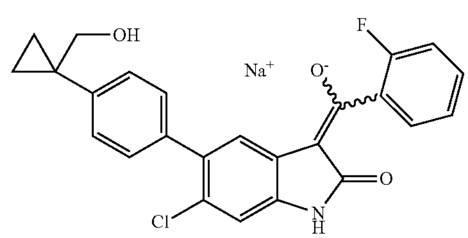 | 1 | 435 1.42 |
| 48 | 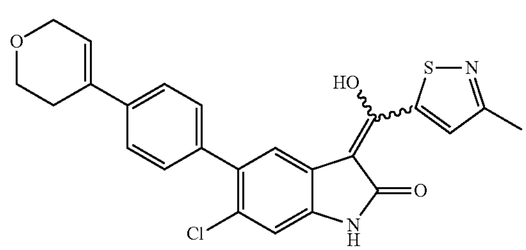 | 1 | 451 1.65 |

TABLE 1-continued

| Compound | Structure | Scheme | LC/MS data [M + H]+ T$_{R[min]}$ |
|---|---|---|---|
| 49 | 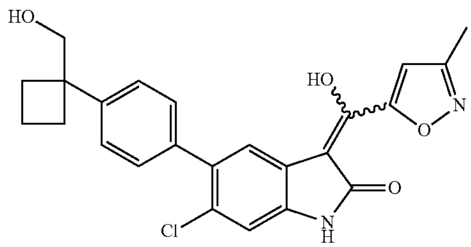 | 1 | 437 1.51 |
| 50 | 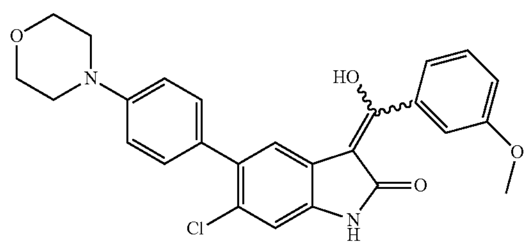 | 1 | 463 1.56 |
| 51 | 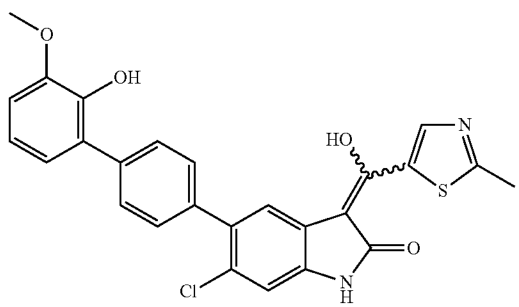 | 5 | 491 1.53 |
| 52 | 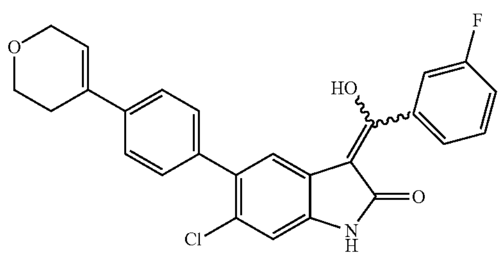 | 1 | 448 1.71 |
| 53 | 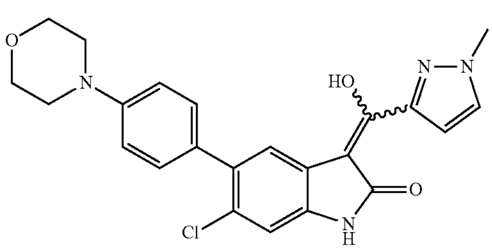 | 1 | 437 1.29 |
| 54 | 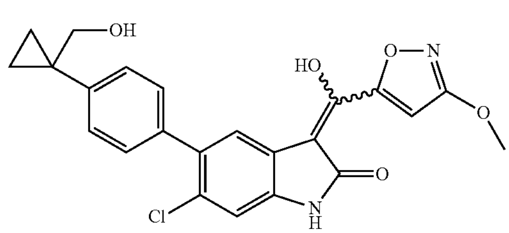 | 1 | 436 1.43 |

TABLE 1-continued

| Compound | Structure | Scheme | LC/MS data [M + H]+ T$_{R[min]}$ |
|---|---|---|---|
| 55 | 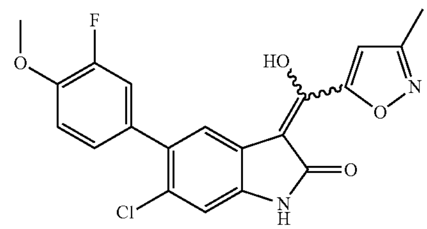 | 1 | 401 1.54 |
| 56 | 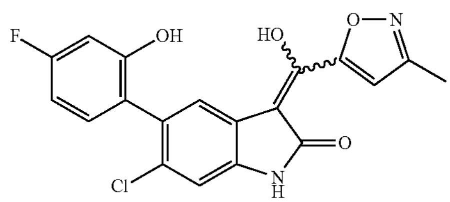 | 6 | 387 1.32 |
| 57 | 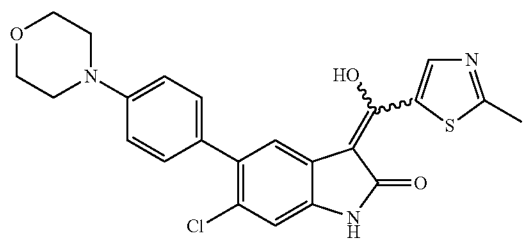 | 1 | 454 1.42 |
| 58 | 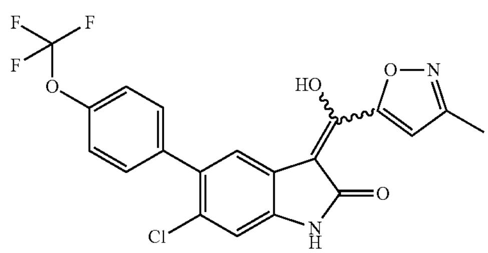 | 1 | 437 1.71 |
| 59 | 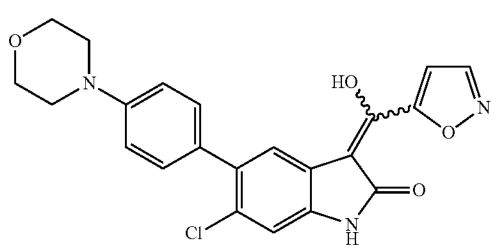 | 1 | 424 1.38 |
| 60 | 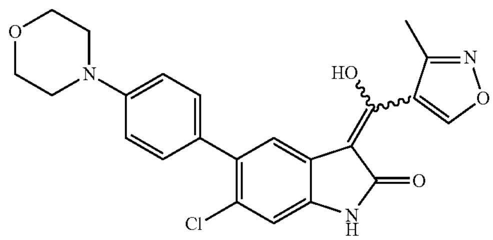 | 1 | 438 1.31 |

TABLE 1-continued

| Compound | Structure | Scheme | LC/MS data [M + H]+ T$_{R[min]}$ |
|---|---|---|---|
| 61 | 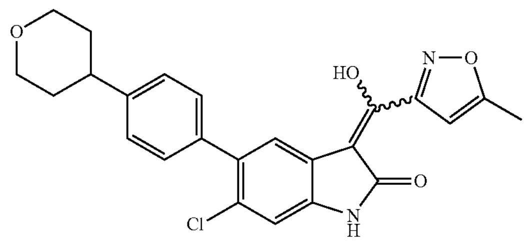 | 1 | 437 1.61 |
| 62 | 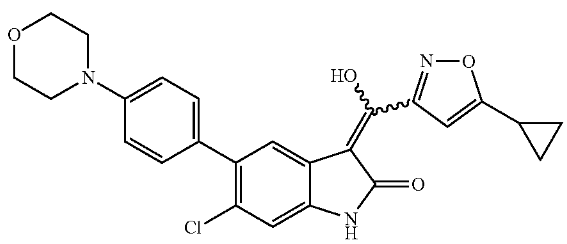 | 1 | 464 1.61 |
| 63 | 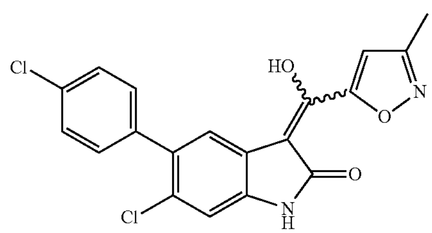 | 6 | 387 1.68 |
| 64 | 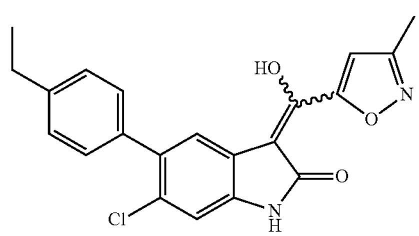 | 6 | 381 1.72 |
| 65 | 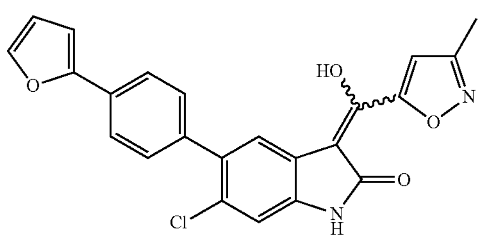 | 6 | 419 1.70 |
| 66 | 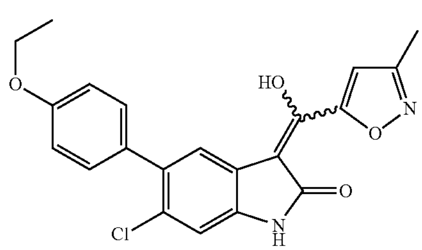 | 6 | 397 1.62 |

TABLE 1-continued

| Compound | Structure | Scheme | LC/MS data [M + H]+ T$_{R[min]}$ |
|---|---|---|---|
| 67 | 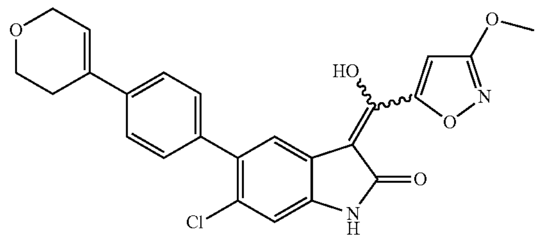 | 1 | 451 1.64 |
| 68 | 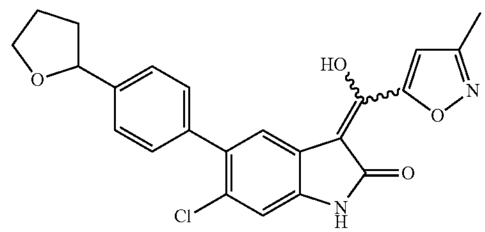 | 1 | 423 1.58 |
| 69 | 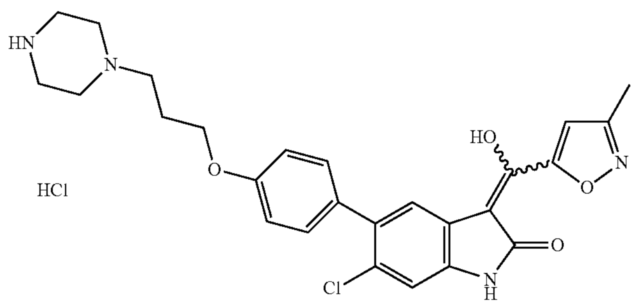 | 6 | 495 0.78 |
| 70 | 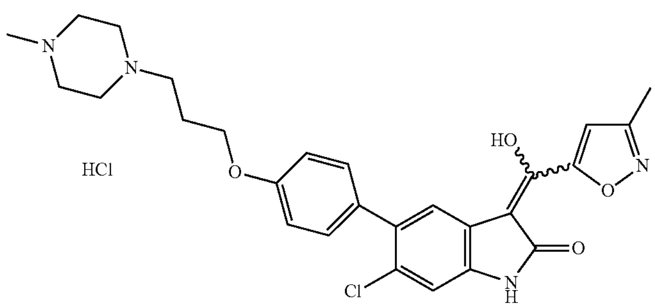 | 6 | 509 0.85 |
| 71 | 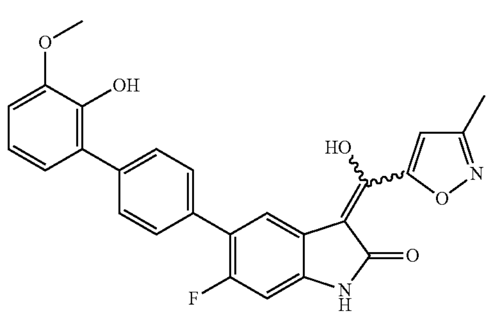 | 5 | 475 1.68 |

TABLE 1-continued
| Compound | Structure | Scheme | LC/MS data [M + H]+ T_R[min] |
|---|---|---|---|
| 72 | 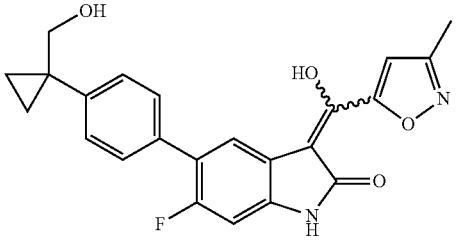 | 1 | 407 1.42 |
| 73 | 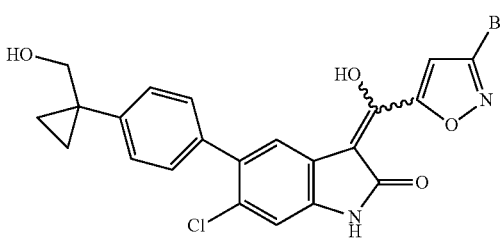 | 1 | 487 1.57 |
| 74 | 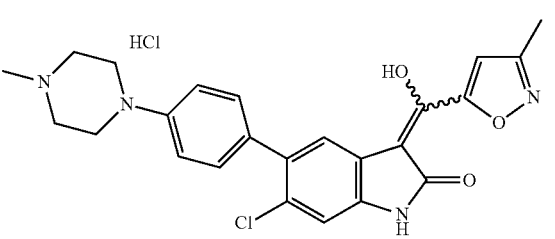 | 6 | 451 0.89 |
| 75 | 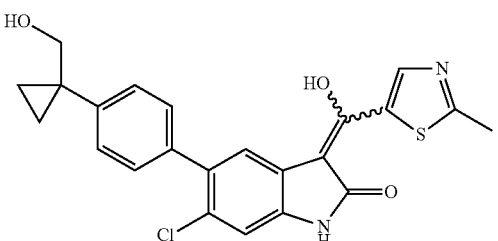 | 1 | 439 3.71 (10 min gradient) |
| 76 | 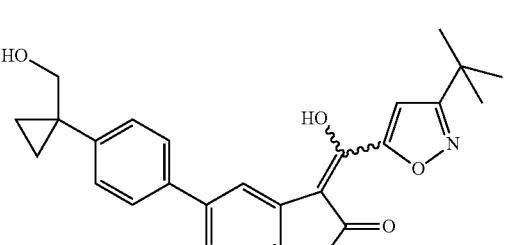 | 1 | 463 1.64 |
| 77 | 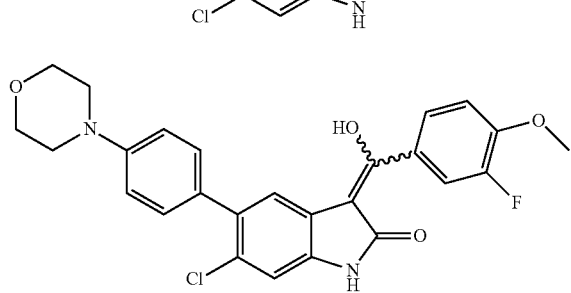 | 1 | 481 1.65 |

TABLE 1-continued
| Compound | Structure | Scheme | LC/MS data [M + H]+ T_{R[min]} |
|---|---|---|---|
| 78 | 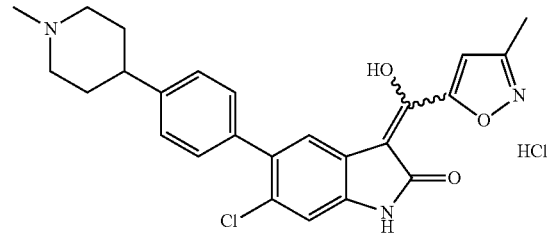 | 6 | 450 0.93 |
| 79 | 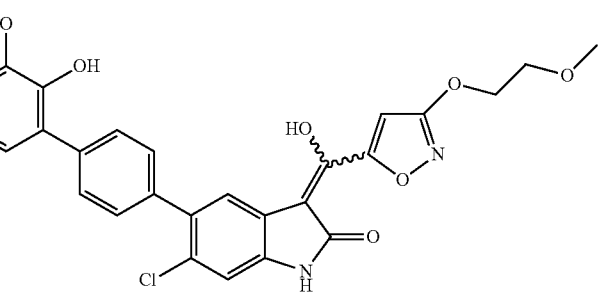 | 5 | 535 1.61 |
| 80 | 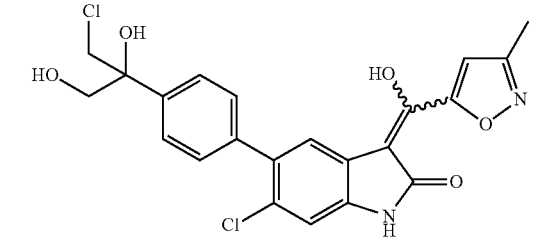 | 6 | 459 1.24 |
| 81 | 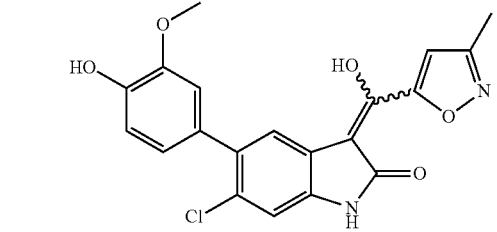 | 6 | 399 1.32 |
| 82 | 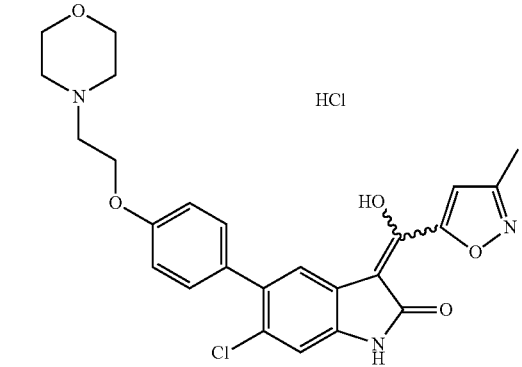 | 6 | 482 0.87 |

TABLE 1-continued

| Compound | Structure | Scheme | LC/MS data [M + H]+ T$_{R[min]}$ |
|---|---|---|---|
| 83 | 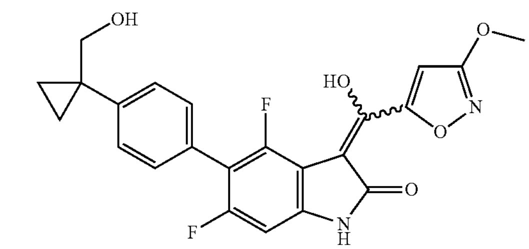 | 1 | 441 1.14 |
| 84 | 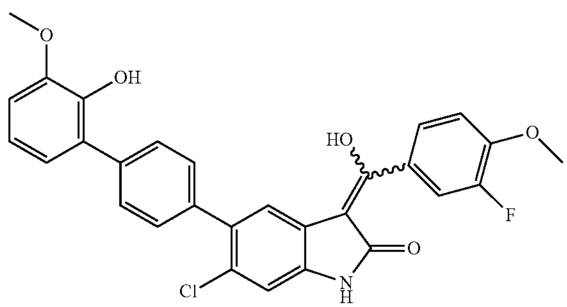 | 6 | 518 1.66 |
| 85 | 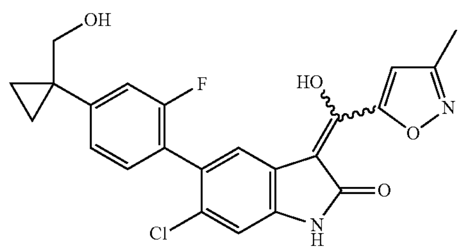 | 6 | 441 1.39 |
| 86 | 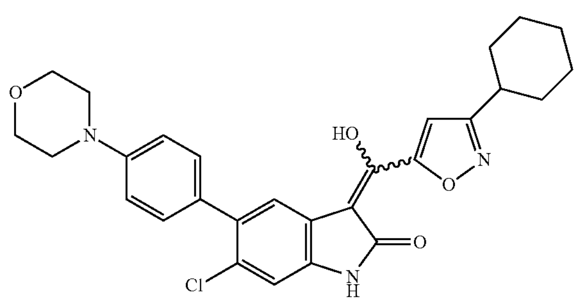 | 1 | 506 1.83 |
| 87 | 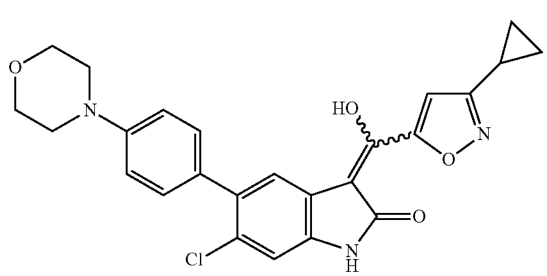 | 1 | 464 1.55 |

TABLE 1-continued
| Compound | Structure | Scheme | LC/MS data [M + H]+ T$_{R[min]}$ |
|---|---|---|---|
| 88 | 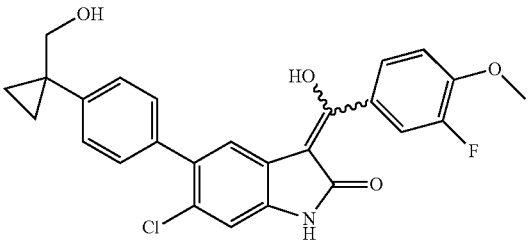 | 1 | 466 1.48 |
| 89 | 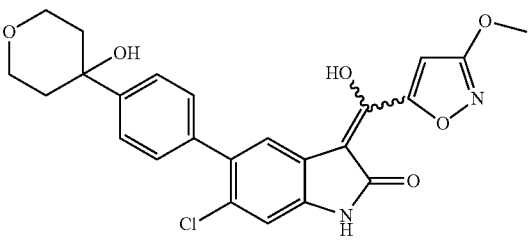 | 1 | 469 2.90 (7 min gradient) |
| 90 | 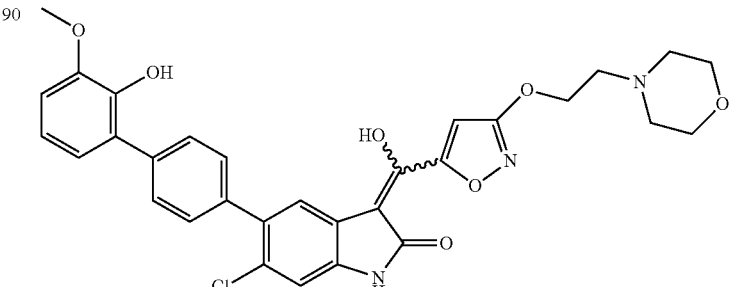 | 5 | 590 1.04 |
| 91 | 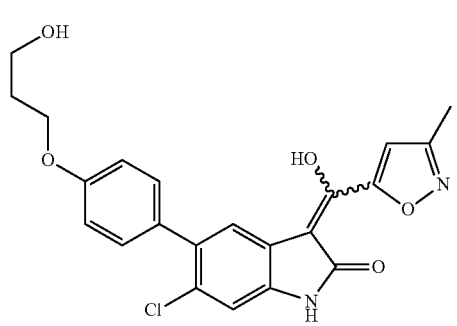 | 6 | 427 2.89 (7 min gradient) |
| 92 | 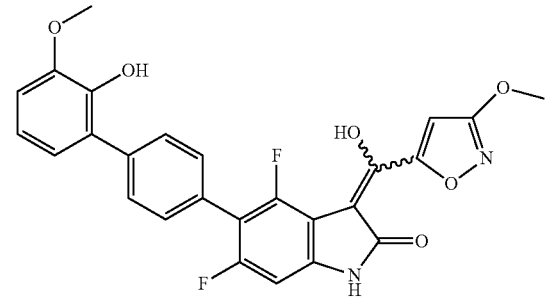 | 5 | 493 1.38 |

TABLE 1-continued

| Compound | Structure | Scheme | LC/MS data [M + H]+ T$_{R[min]}$ |
|---|---|---|---|
| 93 | (morpholine-phenyl)-Cl-oxindole-3-(hydroxy)(phenyl-N-methylpiperazine) · HCl | 1 | 529 0.96 |
| 94 | (morpholine-phenyl)-Cl-oxindole-3-(hydroxy)(phenyl-morpholine) | 1 | 518 1.4 |
| 95 | (morpholine-phenyl)-Cl-oxindole-3-(hydroxy)(fluoro-trifluoromethoxy-phenyl) | 1 | 535 1.56 |
| 96 | (hydroxymethyl-cyclopropyl-fluorophenyl)-Cl-oxindole-3-(hydroxy)(methoxy-isoxazole) | 1 | 457 1.37 |
| 97 | (morpholine-phenyl)-Cl-oxindole-3-(hydroxy)(fluoro-methoxy-chloro-phenyl) | 1 | 515 1.52 |
| 98 | (morpholine-phenyl)-Cl-oxindole-3-(hydroxy)(difluoro-methoxy-phenyl) | 1 | 499 1.62 |

TABLE 1-continued

| Compound | Structure | Scheme | LC/MS data [M + H]+ $T_{R[min]}$ |
|---|---|---|---|
| 99 | 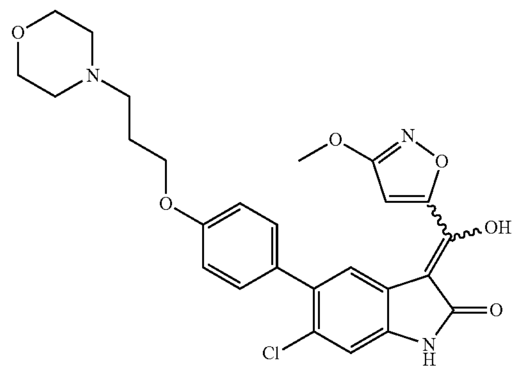 | 1 | 512<br>0.98 |
| 100 | 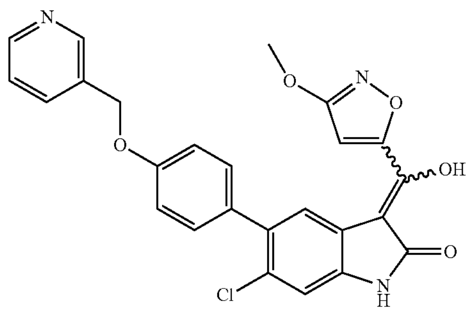 | 1 | 476<br>1.22 |
| 101 | 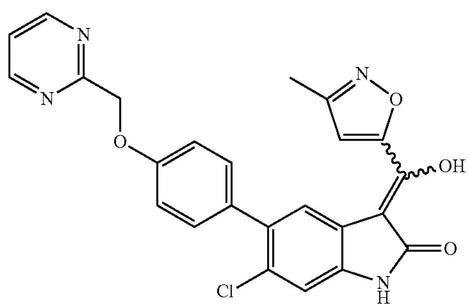 | 1 | 461<br>1.36 |
| 102 | 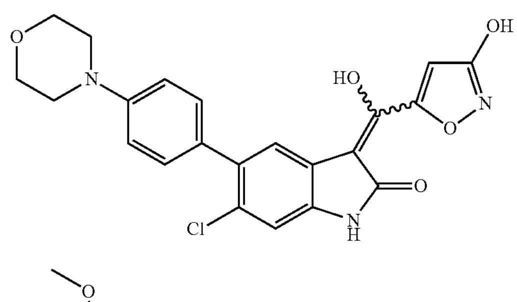 | 1 | 440<br>1.19 |
| 103 | 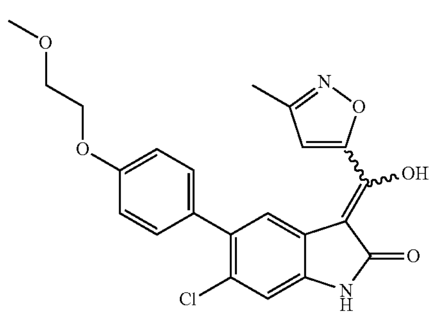 | 1 | 427<br>1.38 |

TABLE 1-continued
| Compound | Structure | Scheme | LC/MS data [M + H]+ T$_{R[min]}$ |
|---|---|---|---|
| 104 | 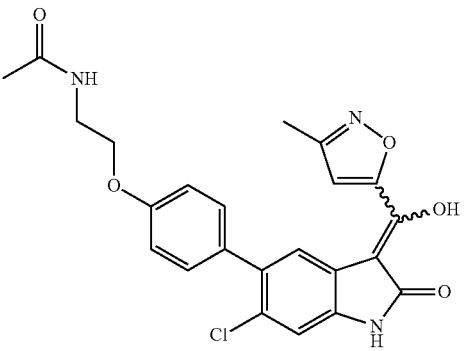 | 1 | 454 1.22 |
| 105 | 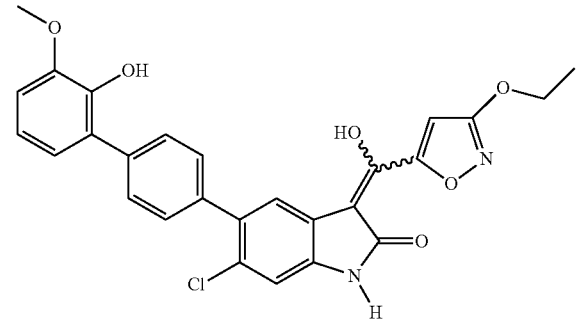 | 5 | 505 1.58 |
| 106 | 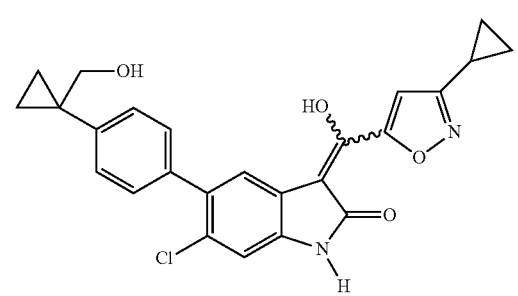 | 1 | 449 1.41 |
| 107 | 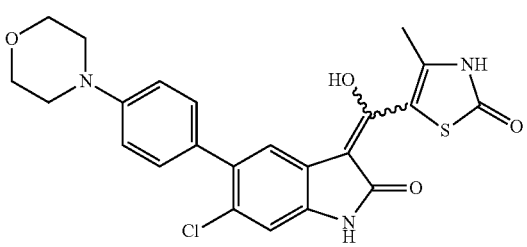 | 1 | 470 1.17 |
| 108 | 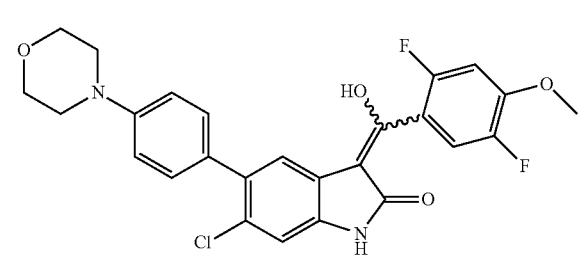 | 1 | 499 1.50 |

TABLE 1-continued

| Compound | Structure | Scheme | LC/MS data [M + H]+ T$_{R[min]}$ |
|---|---|---|---|
| 109 | 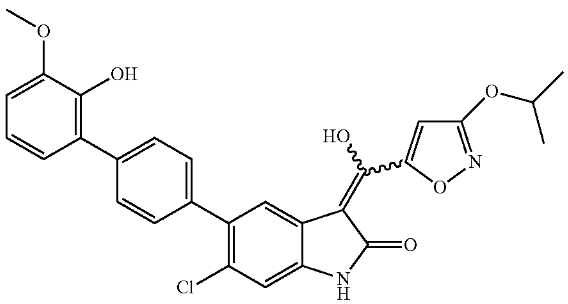 | 5 | 519 1.71 |
| 110 | 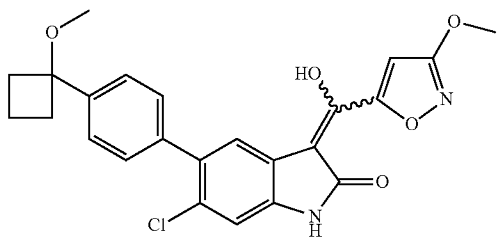 | 1 | 453 1.64 |
| 111 | 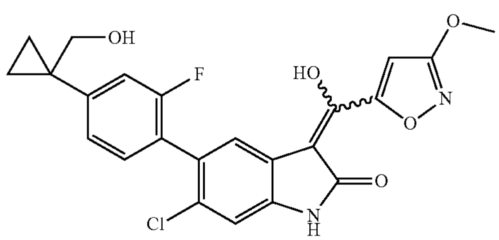 | 1 | 457 1.42 |
| 112 | 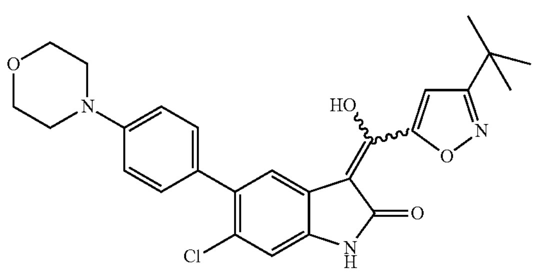 | 1 | 480 1.54 |
| 113 | 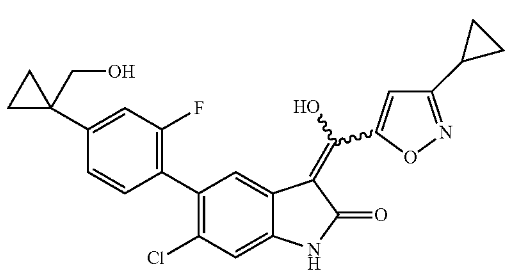 | 1 | 467 1.40 |

TABLE 1-continued

| Compound | Structure | Scheme | LC/MS data [M + H]+ T$_{R[min]}$ |
|---|---|---|---|
| 114 | 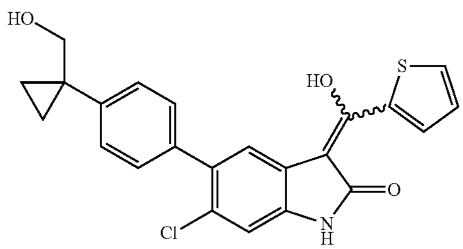 | 1 | 424 1.32 |
| 115 | 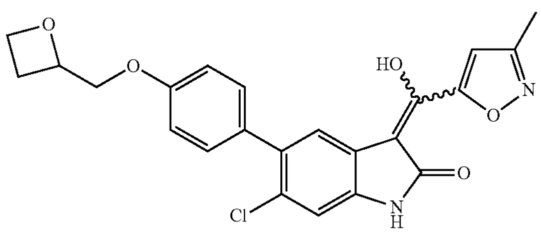 | 6 | 439 1.36 |
| 116 | 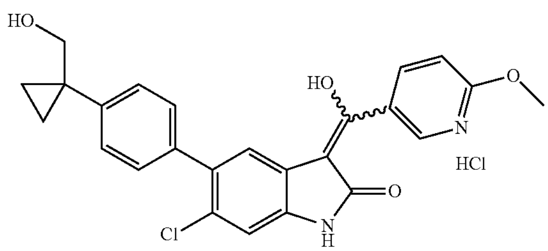 | 1 | 449 1.41 |
| 117 | 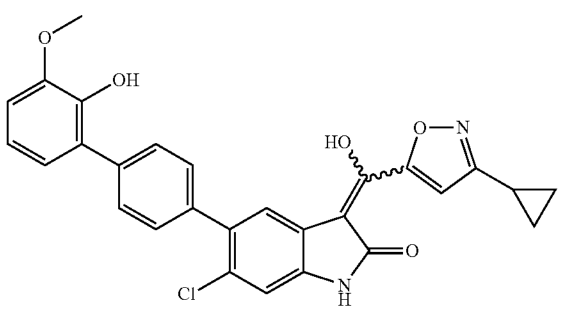 | 6 | 501 1.70 |
| 118 | 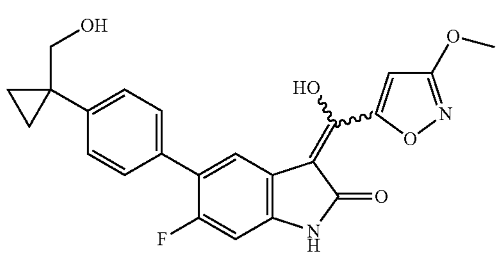 | 6 | 423 1.32 |

TABLE 1-continued
| Compound | Structure | Scheme | LC/MS data [M + H]+ T$_{R[min]}$ |
|---|---|---|---|
| 119 | 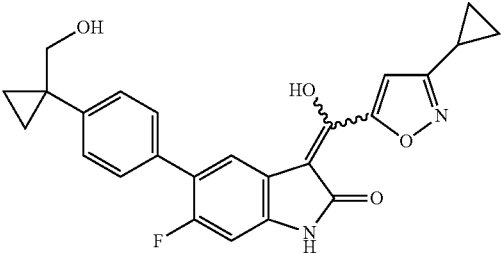 | 6 | 433 1.38 |
| 120 | 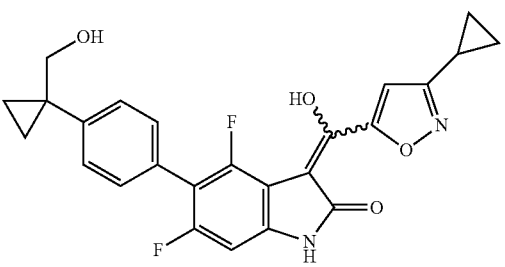 | 6 | 451 1.31 |
| 121 | 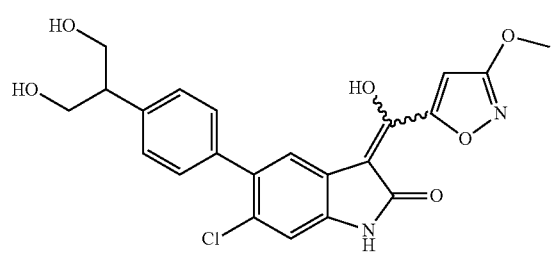 | 6 | 443 1.22 |
| 122 | 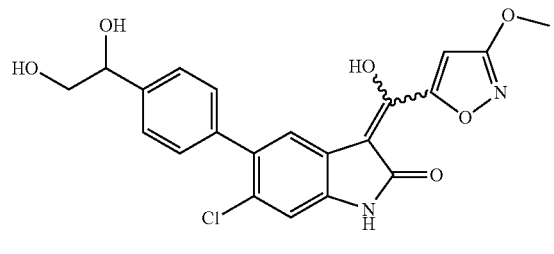 | 6 | 429 1.21 |
| 123 | 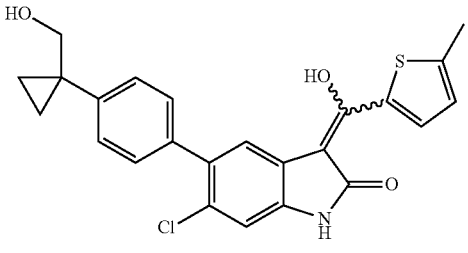 | 6 | 438 1.47 |
| 124 | 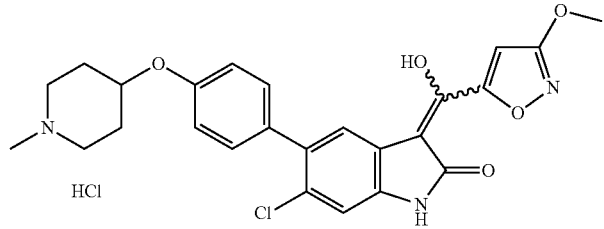 | 6 | 482 0.99 |

TABLE 1-continued

| Compound | Structure | Scheme | LC/MS data [M + H]+ T$_{R[min]}$ |
|---|---|---|---|
| 125 | 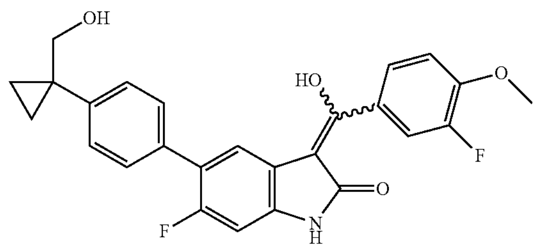 | 6 | 450 3.77 (10 min gradient) |
| 126 | 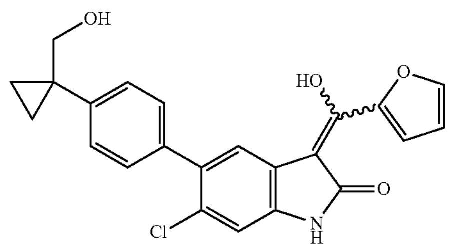 | 1 | 408 1.49 |
| 127 | 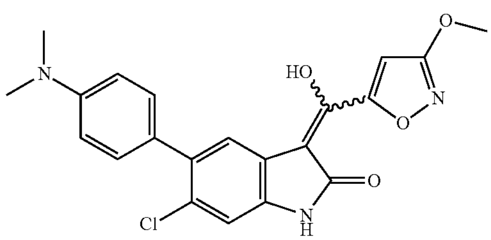 | 6 | 412 1.55 |
| 128 | 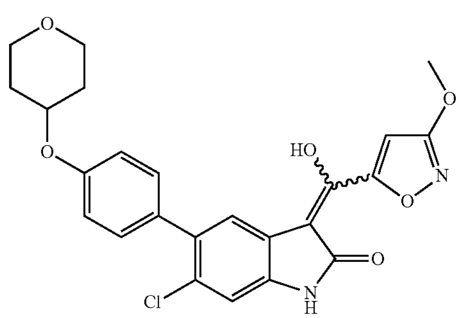 | 6 | 469 1.68 |
| 129 | 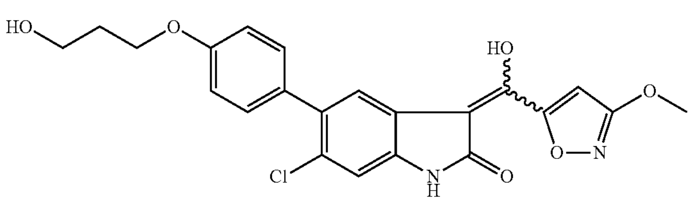 | 6 | 443 1.38 |
| 130 | 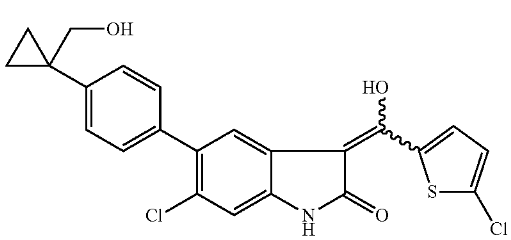 | 1 | 458 1.57 |

TABLE 1-continued
| Compound | Structure | Scheme | LC/MS data [M + H]+ T_R[min] |
|---|---|---|---|
| 131 | 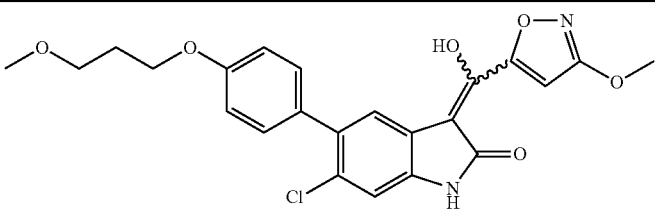 | 6 | 457 1.50 |
| 132 | 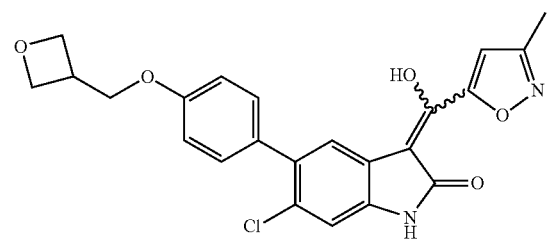 | 6 | 439 1.47 |
| 133 | 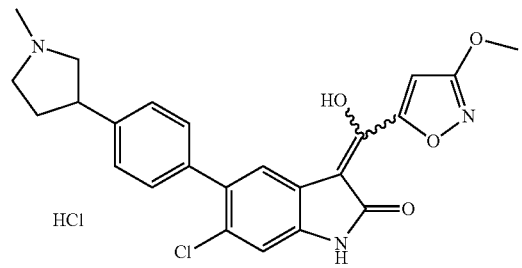 | 6 | 452 0.88 |
| 134 | 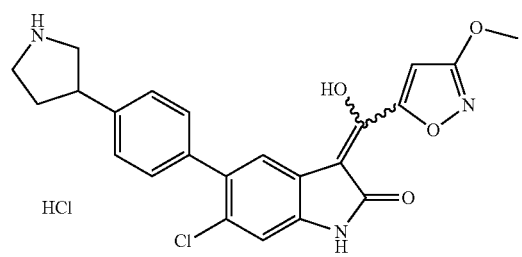 | 6 | 438 0.87 |
| 135 | 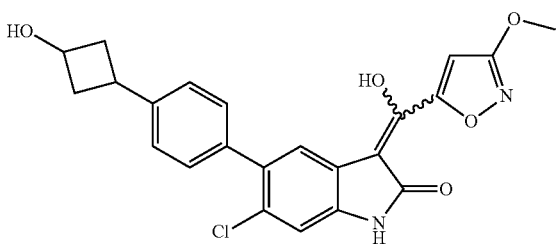 | 6 | 439 1.35 |
| 136 | 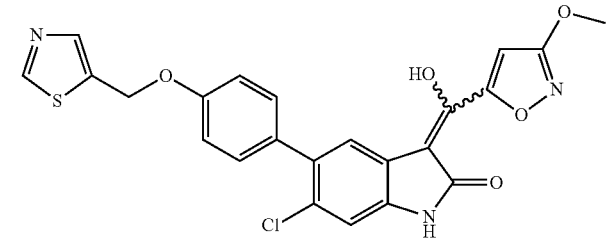 | 6 | 482 1.53 |

TABLE 1-continued

| Compound | Structure | Scheme | LC/MS data [M + H]+ T$_{R[min]}$ |
|---|---|---|---|
| 137 | 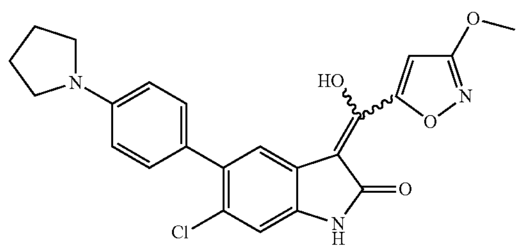 | 6 | 438 1.79 |
| 138 | 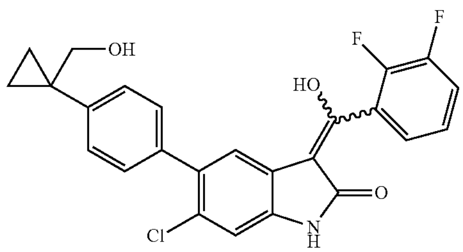 | 6 | 454 1.53 |
| 139 | 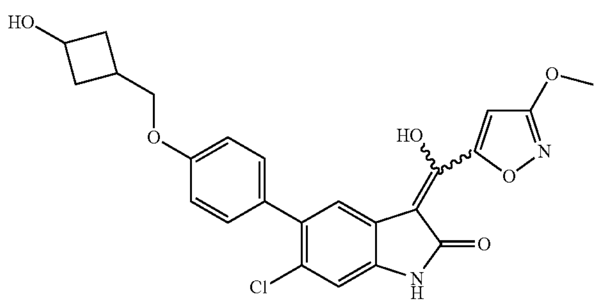 | 6 | 469 1.43 |
| 140 | 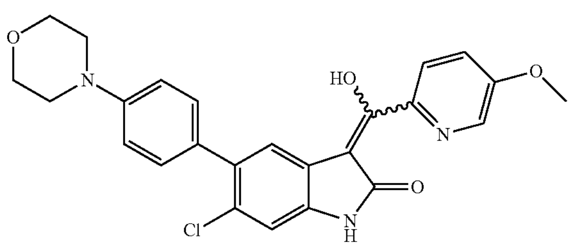 | 1 | 464 1.25 |
| 141 | 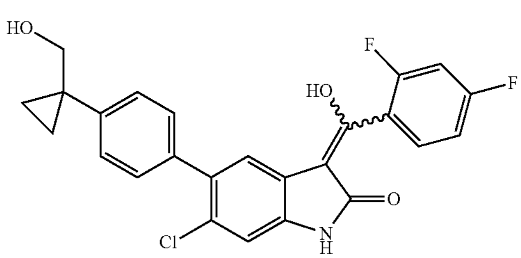 | 6 | 454 1.43 |

TABLE 1-continued
| Compound | Structure | Scheme | LC/MS data [M + H]+ T_{R[min]} |
|---|---|---|---|
| 142 | 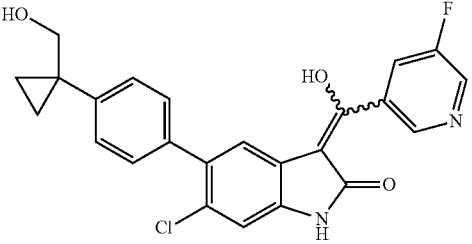 | 1 | 437 1.28 |
| 143 | 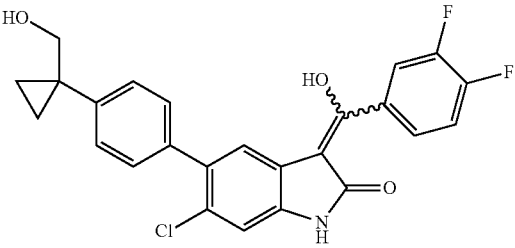 | 1 | 454 1.49 |
| 144 | 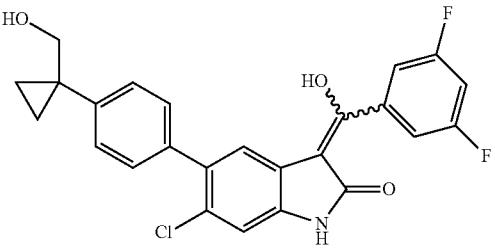 | 1 | 454 1.50 |
| 145 | 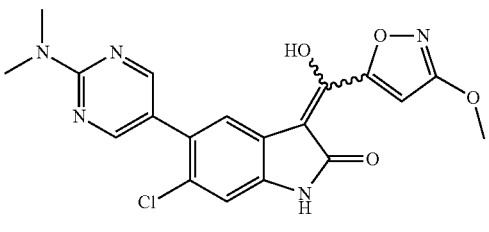 | 1 | 414 1.42 |
| 146 | 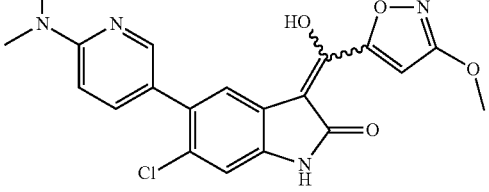 | 6 | 413 0.79 |
| 147 | 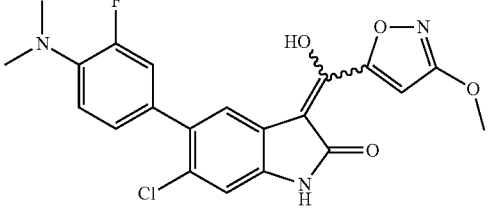 | 6 | 430 4.41 (10 min gradient) |

TABLE 1-continued

| Compound | Structure | Scheme | LC/MS data [M + H]+ T_{R[min]} |
|---|---|---|---|
| 148 | 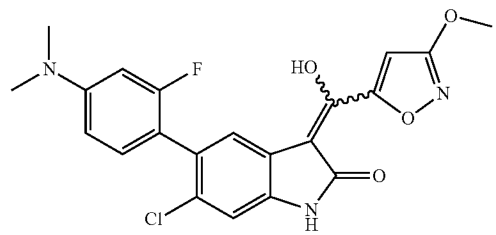 | 6 | 430<br>1.61 |
| 149 | 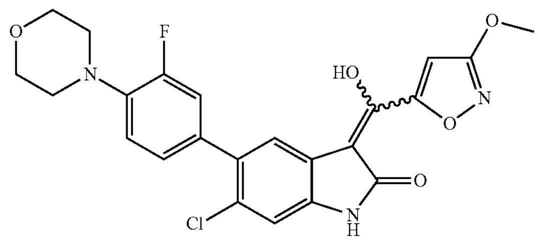 | 6 | 472<br>1.43-1.80<br>very<br>broad<br>peak |
| 150 | 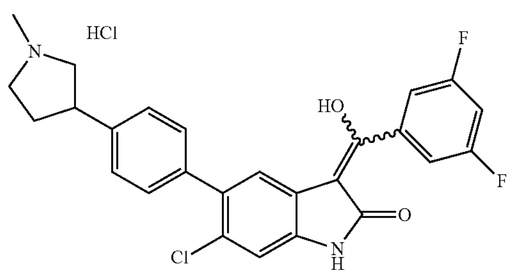 | 6 | 467<br>0.91 |
| 151 | 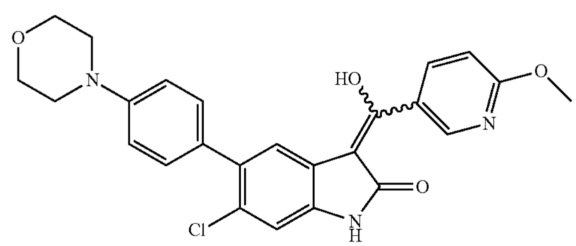 | 1 | 464<br>1.50 |
| 152 | 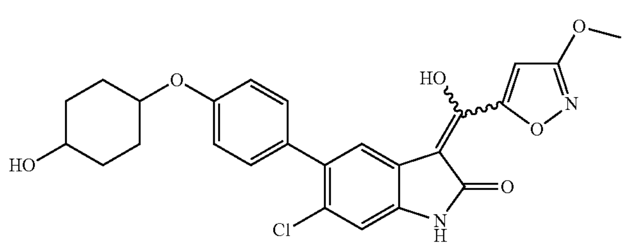 | 6 | 483<br>1.45 |
| 153 | 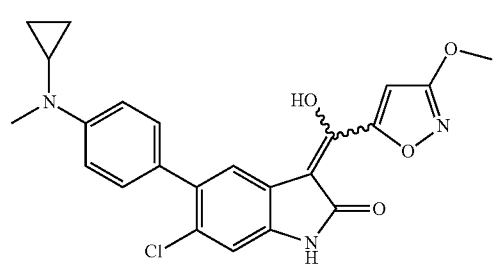 | 6 | 438<br>1.77 |

TABLE 1-continued

| Compound | Structure | Scheme | LC/MS data [M + H]+ T$_{R[min]}$ |
|---|---|---|---|
| 154 | 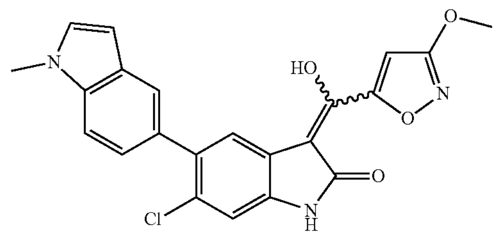 | 6 | 422 1.60 |
| 155 | 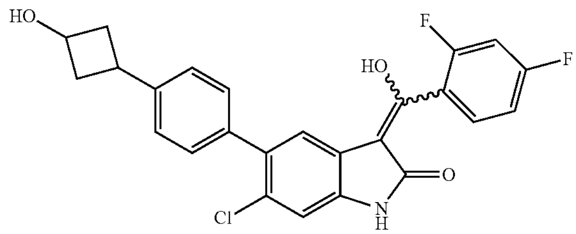 | 6 | 454 1.42 |
| 156 | 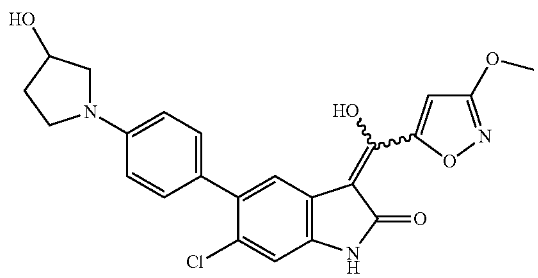 | 6 | 454 1.40 |
| 157 | 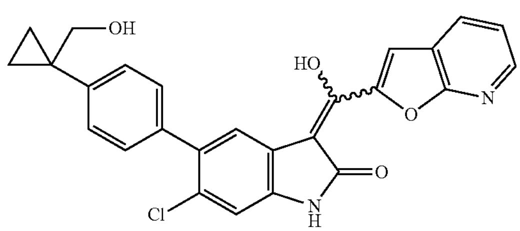 | 6 | 457 1.45 |
| 158 | 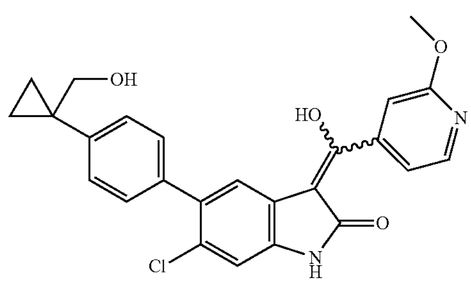 | 6 | 449 1.43 |
| 159 | 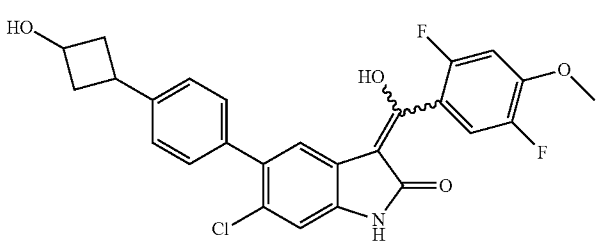 | 6 | 484 1.42 |

TABLE 1-continued
| Compound | Structure | Scheme | LC/MS data [M + H]+ T$_{R[min]}$ |
|---|---|---|---|
| 160 | 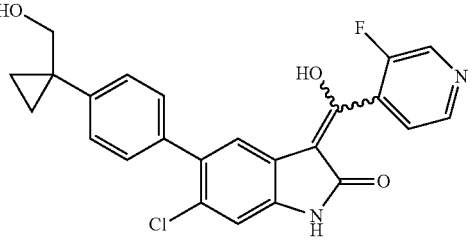 | 6 | 437 1.17 |
| 161 | 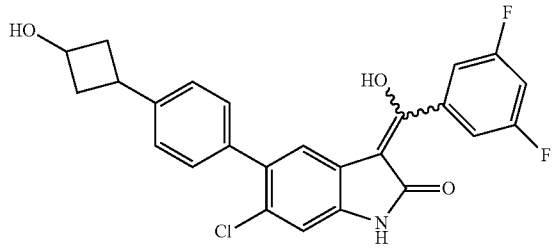 | 6 | 454 1.47 |
| 162 | 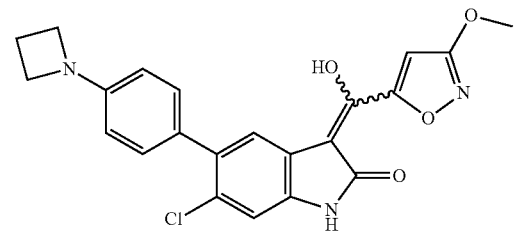 | 6 | 424 1.61 |
| 163 | 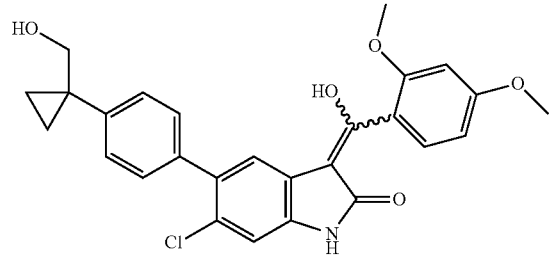 | 6 | 478 1.39 |
| 164 | 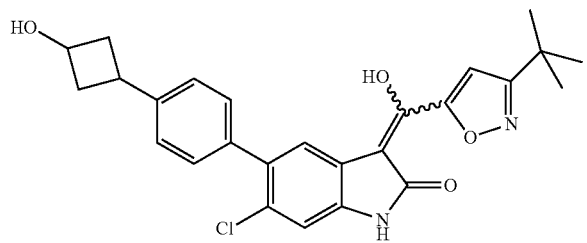 | 6 | 465 1.61 |
| 165 | 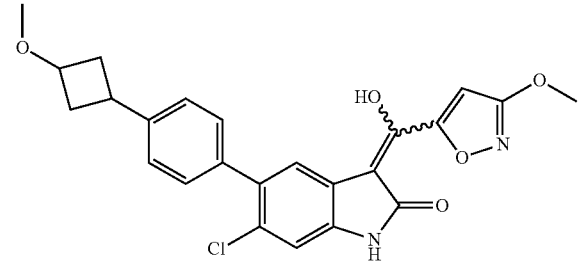 | 6 | 453 1.47 |

TABLE 1-continued

| Compound | Structure | Scheme | LC/MS data [M + H]+ T_R[min] |
|---|---|---|---|
| 166 | 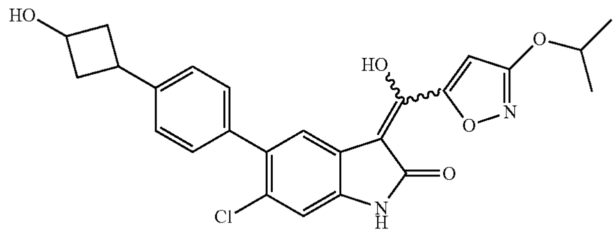 | 6 | 467 1.54 |
| 167 | 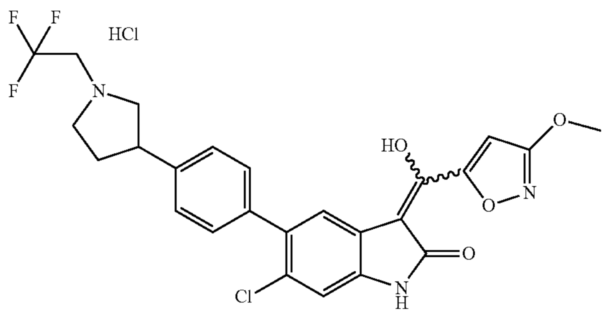 | 6 | 520 1.52 |
| 168 | 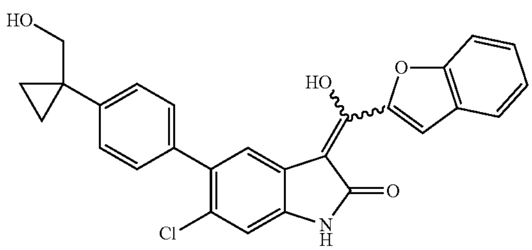 | 6 | 458 1.62 |
| 169 | 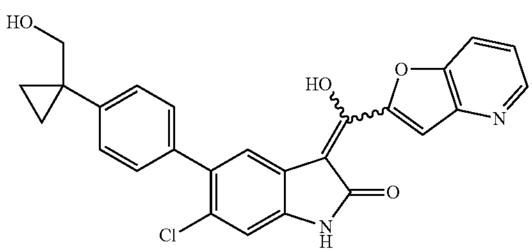 | 6 | 459 1.38 |
| 170 | 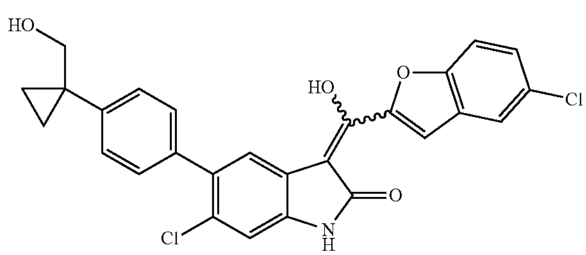 | 6 | 491 1.76 |
| 171 | 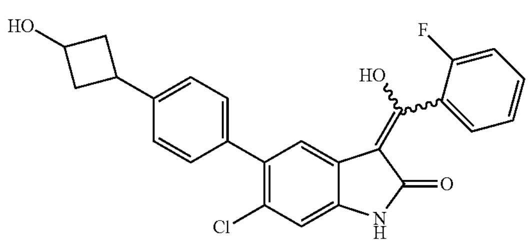 | 6 | 436 4.50 (14%)- 4.55 (96%) (10 min gradient) |

TABLE 1-continued
| Compound | Structure | Scheme | LC/MS data [M + H]+ T_{R[min]} |
|---|---|---|---|
| 173 | 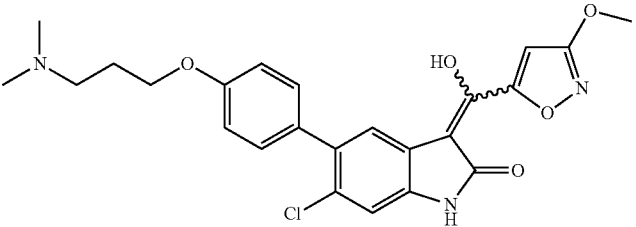 | 6 | 470-468 1.05 |
| 174 | 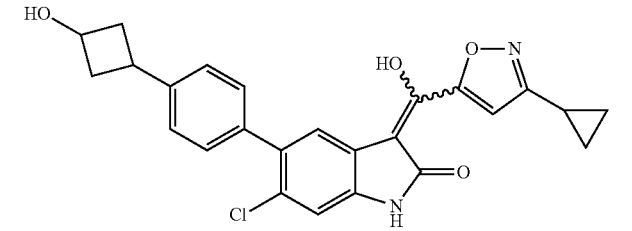 | 6 | 449 4.82 (10 min gradient) |
| 175 | 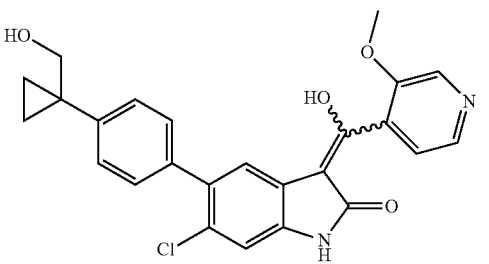 | 6 | 449 1.08 |
| 176 | 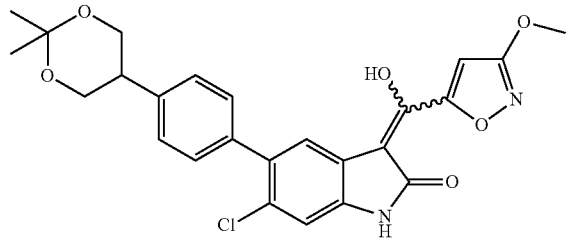 | 6 | 483 1.58 |
| 177 | 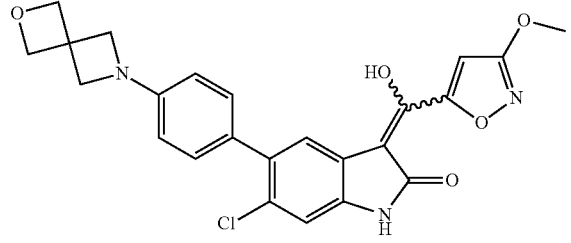 | 6 | 466 1.49 |
| 178 | 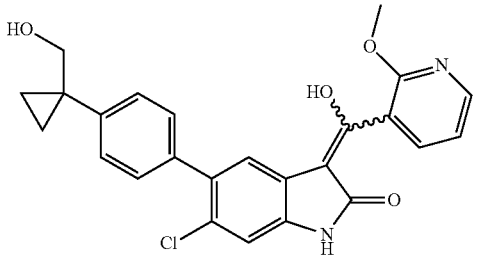 | 6 | 449 1.31 |

TABLE 1-continued

| Compound | Structure | Scheme | LC/MS data [M + H]+ $T_{R[min]}$ |
|---|---|---|---|
| 179 | 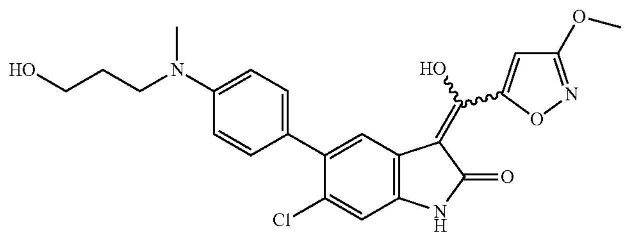 | 6 (deprot globale) | 456 1.17 |
| 180 | 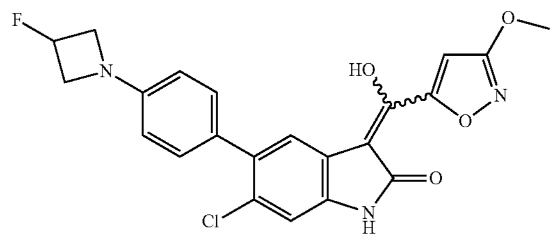 | 6 | 442 1.58 |
| 181 | 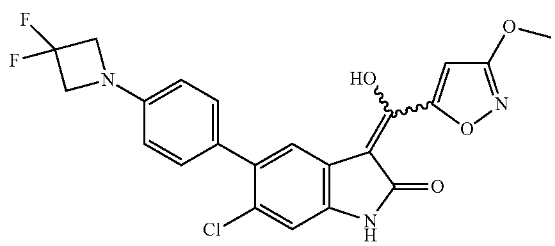 | 6 | 460 1.65 |
| 182 | 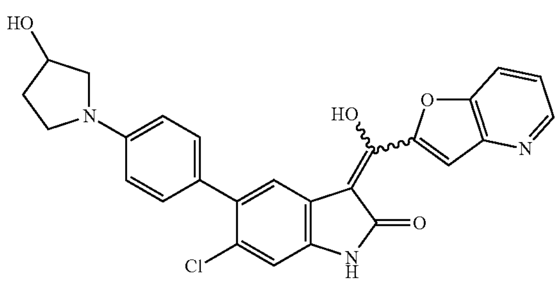 | 6 | 474 1.39 |
| 183 | 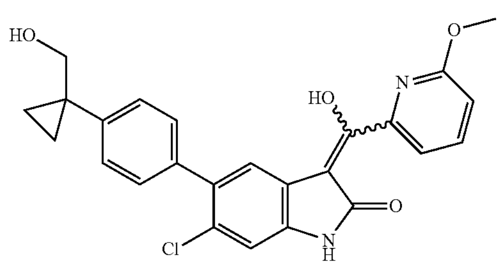 | 6 | 449 1.37 |
| 184 | 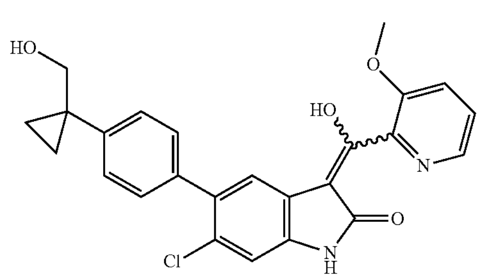 | 6 | 449 1.10 |

TABLE 1-continued

| Compound | Structure | Scheme | LC/MS data [M + H]+ T_{R[min]} |
|---|---|---|---|
| 185 | 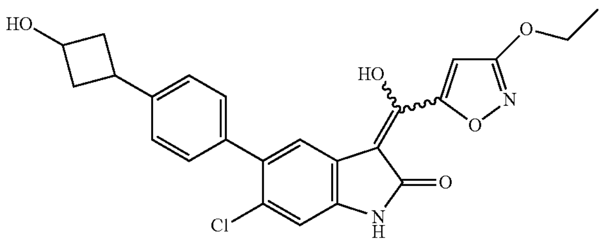 | 6 | 453 1.49 |
| 186 | 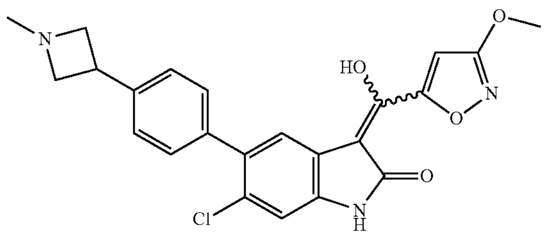 | 6 | 438 0.83 |
| 187 | 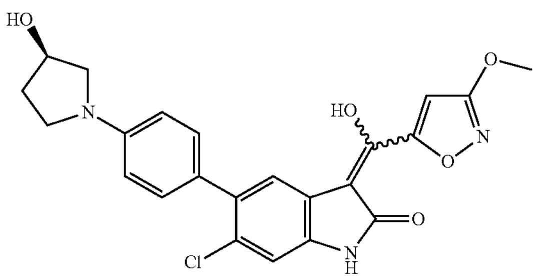 | 6 | 454 1.38 |
| 188 | 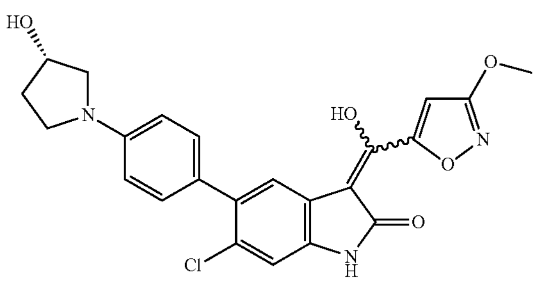 | 6 | 454 4.42 (10 min gradient) |
| 189 | 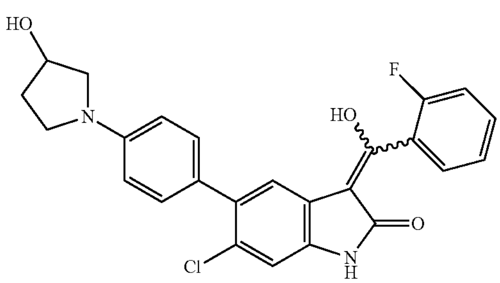 | 6 | 451 1.39 |

TABLE 1-continued

| Compound | Structure | Scheme | LC/MS data [M + H]+ T_{R[min]} |
|---|---|---|---|
| 190 | 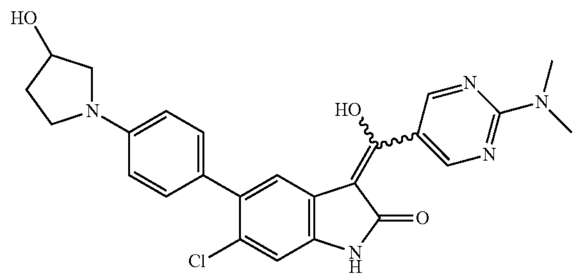 | 6 | 478 1.36 |
| 191 | 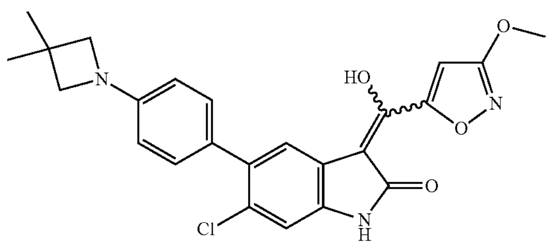 | 6 | 452 1.83 |
| 192 | 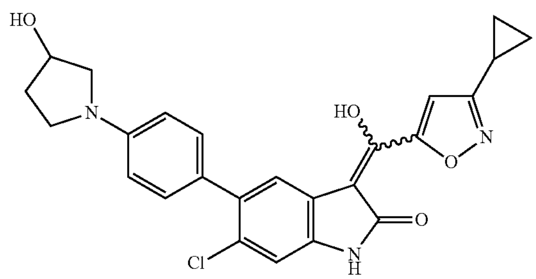 | 6 | 464 1.48 |
| 193 | 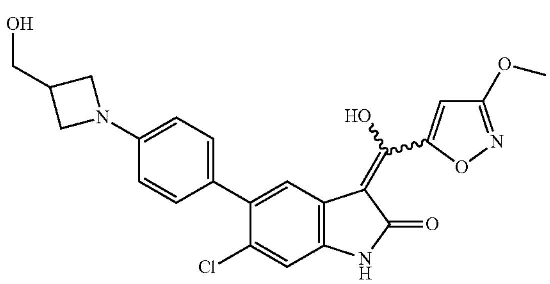 | 6 | 454 1.33 |
| 194 | 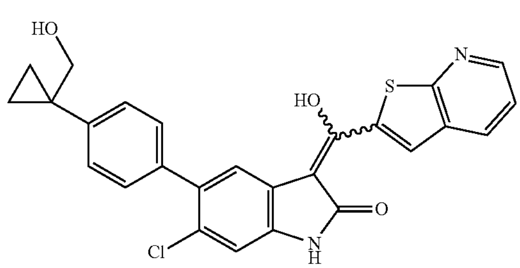 | 6 | 475 1.38 |

TABLE 1-continued

| Compound | Structure | Scheme | LC/MS data [M + H]+ T_{R[min]} |
|---|---|---|---|
| 195 | 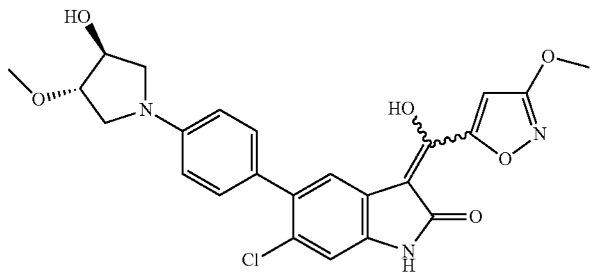 | 6 | 484 1.38 |
| 196 | 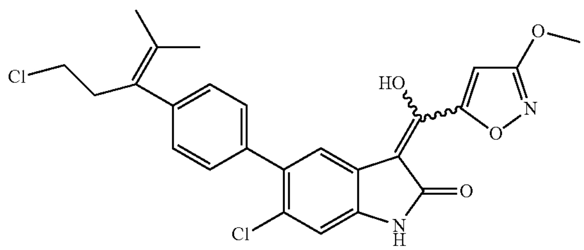 | 6 | 485 1.91 |
| 197 | 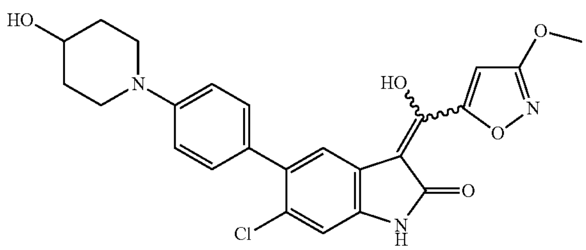 | 6 | 468 1.05 |
| 198 | 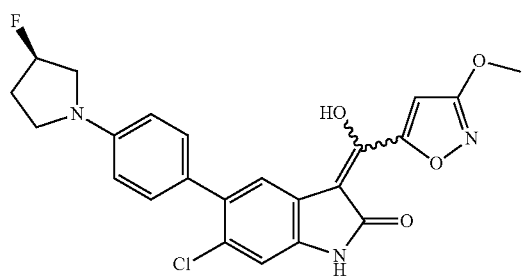 | 6 | 456 1.63 |
| 199 | 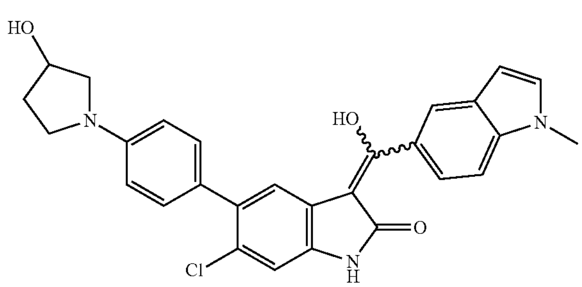 | 6 | 486 1.48 |

TABLE 1-continued

| Compound | Structure | Scheme | LC/MS data [M + H]+ T$_{R[min]}$ |
|---|---|---|---|
| 200 | 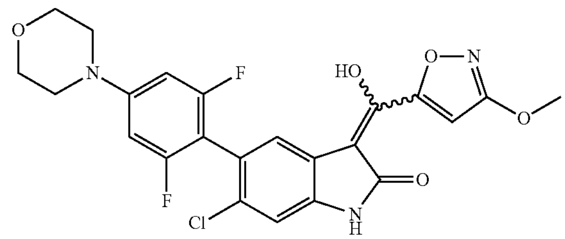 | 6 | 490 1.50 |
| 201 | 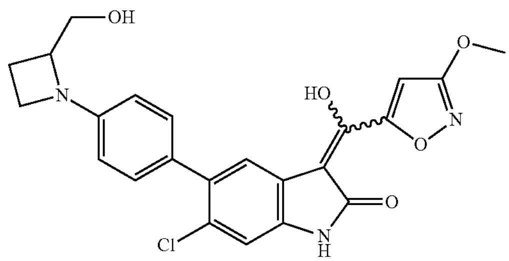 | 6 | 454 1.37 |
| 202 | 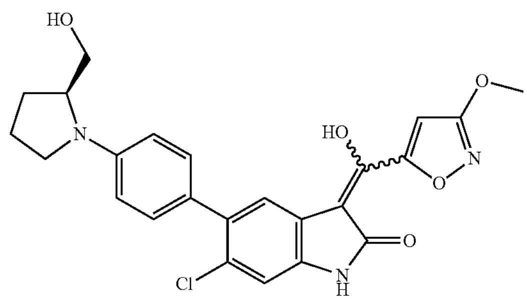 | 6 | 468 1.46 |
| 203 | 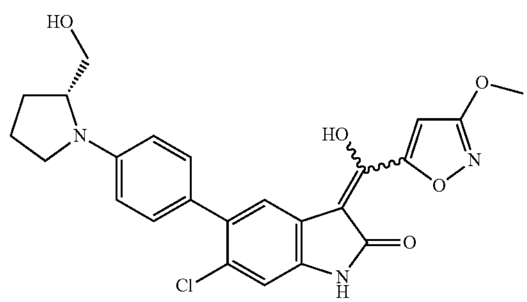 | 6 | 468 1.46 |
| 204 | 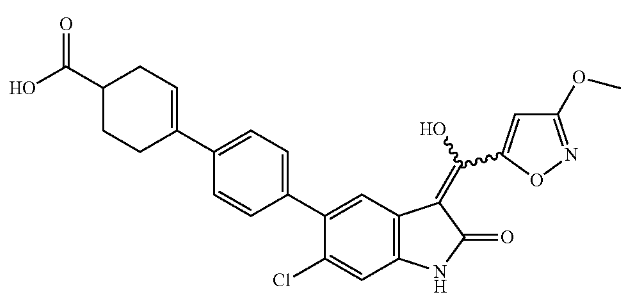 | 6 | 493 1.54 |

TABLE 1-continued

| Compound | Structure | Scheme | LC/MS data [M + H]+ T$_{R[min]}$ |
|---|---|---|---|
| 205 | 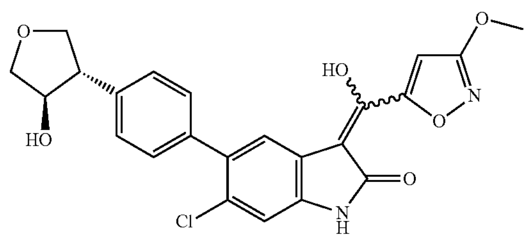 | 6 | 455 1.27 |
| 206 | 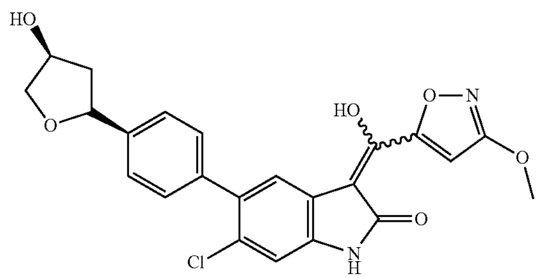 | 6 | 455 1.27 |
| 207 | 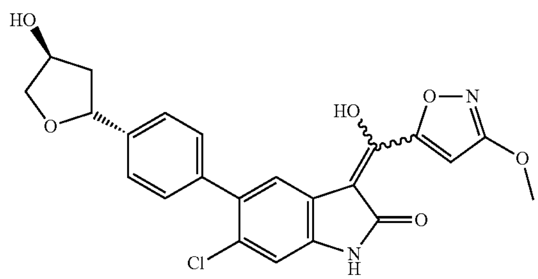 | 6 | 455 1.28 |
| 208 | 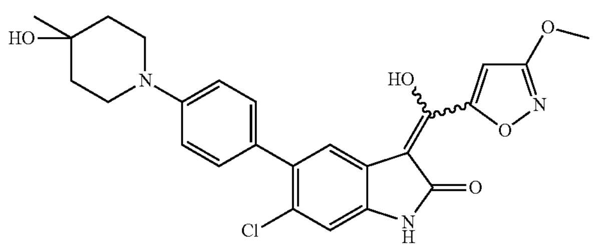 | 6 | 482 1.06 |
| 209 | 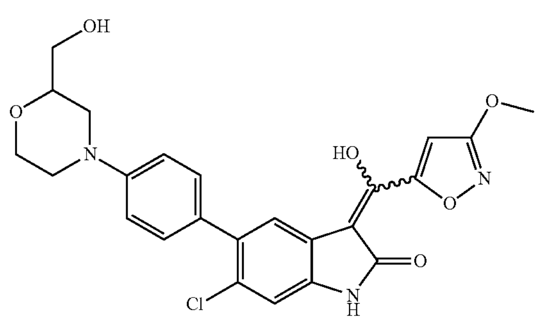 | 6 | 484 1.29 |

TABLE 1-continued

| Compound | Structure | Scheme | LC/MS data [M + H]+ T$_{R[min]}$ |
|---|---|---|---|
| 210 | (structure) | 6 | 484 1.28 |

The compounds according to the invention underwent pharmacological trials to determine their activation effect of AMP-activated protein kinase (AMPK).

AMPK in vitro Activation Assay

The recombinant human AMPK complex, containing $\alpha_2\beta_1\gamma_2$ was obtained from baculovirus expression system and generated by cotransfection in *Spodoptera frugiperda* 21 (Sf21). 13.6 of Sf21 cells were produced in serum free medium (SF900 II, Invitrogen) for 82 hours after a triple infection at a multiplicity of infection (M.O.I.) of 0.05, 0.06 and 0.045 for hsAMPK$\alpha_2$-552-His, hsAMPK$\beta_1$-2-270 and hsAMPK$\gamma$-2-569 respectively. Cells were harvested by centrifugation at 1,000×g for 10 minutes at 4° C. and stored at −80° C. The insect cell pellet from 8 liters of culture was resuspended and homogenized in 580 ml of lysis buffer (20 mM Hepes pH 7.5, 150 mM NaCl, 10 mM imidazole, 50 mM NaF, 10% Glycerol and supplemented with EDTA free proteases inhibitor cocktail Roche). The AMPK complex was partially purified using an affinity chromatography under a Ni-NTA Agarose column equilibrated in the lysis buffer and eluted with a gradient (0 to 400 mM) of Imidazol.

A homogeneous time-resolved fluorescence (HTRF) assay was used (Li et al, Anal. Biochem. (2003) 321, 151-156) to identify compounds with stimulating activity for the recombinant human AMPK. Enzyme reaction was performed into a 96-well microtiter plate. First, 20 μL of test compounds in 0.5% DMSO were dispensed followed by 10 μL of protein in 50 mM HEPES buffer at pH 7.0, 100 mM NaCl, 5 mM MgCl$_2$, 0.01% BSA, 0.8 mM DTT. After, 30 min incubation at room temperature, the reaction was initiated by the addition of 10 μL of a solution containing 200 μM of ATP as donor substrate, 2 μM or 0.08 μM of biotinylated ACC-CREBp peptide (PolyPeptide) as acceptor. Plates were then incubated 45 min at 37° C. The reaction was terminated by the addition of 40 μl detection mixture containing Eu$^{3+}$ cryptate-conjugated anti-pS$^{133}$-CREB antibody and streptavidine-XL665 (CisBio). Plates were further incubated for 2 h30 at room temperature. The fluorescence signal was measured using an Envision multireader (Perkin Elmer). The non-specific signal was obtained without substrates. Potentiation of AMPK activity was expressed as a percent over the basal signal (without compound) from which an EC$_{50}$ value was determined.

The EC$_{50}$ of a graded dose response curve represents the concentration of a compound where 50% of its maximal effect is observed.

The EC$_{50}$ values are between 1 nM and 5000 nM and in particular between 3 nM and 60 nM and even more particularly less than 5000 nM.

The table of results for AMPK in vitro activation assay is given below:

TABLE 2

| Compound | $\alpha_2\beta_1\gamma_2$ AMPK EC$_{50}$ (nM) (Emax %) |
|---|---|
| 1 | 21 +/− 26 (124 +/− 11) (n = 3) |
| 2 | 53 +/− 49 (183 +/− 51) (n = 4) |
| 3 | 190 (138) |
| 4 | 15 +/− 2 (97 +/− 31) (n = 3) |
| 5 | 4 +/− 3 (193 +/− 46) (n = 4) |
| 6 | 7 +/− 3.3 (186 +/− 32) (n = 4) |
| 7 | 1400 (57) |
| 8 | 33 +/− 19 (124 +/− 22) (n = 6) |
| 9 | 24 (120) |
|  | 23 (115) |
| 10 | 89 (127) |
| 11 | 4000 (95) |
| 12 | 1 +/− 0 (172 +/− 65) (n = 3) |
| 13 | 12 (158) |
|  | 5 (361) |
| 14 | 38 (283) |
| 15 | 27 (257) |
| 16 | 9 (268) |
| 17 | 120 (289) |
|  | 7 (337) |
| 18 | 190 (135) |
| 19 | 38 (146) |
|  | 230 (249) |
| 20 | 410 (223) |
| 21 | 5 (153) |
|  | 1 (115) |
| 22 | 250 (147) |
| 23 | 3 (158) |
| 24 | 110 (143) |
| 25 | 320 (146) |
| 26 | 440 (153) |
| 27 | 2 (129) |
| 28 | 130 (150) |
| 29 | 58 (157) |
| 30 | 240 (108) |
| 31 | 540 (147) |
| 32 | 140 (112) |

TABLE 2-continued

| Compound | α2β1γ2 AMPK EC$_{50}$ (nM) (Emax %) |
|---|---|
| 33 | 390 (120) |
| 34 | 630 (156) |
| 35 | 23 (151) |
| 36 | 380 (153) |
| 37 | 37 (192) |
| 38 | 700 (133) |
| 39 | 620 (168) |
| 40 | 720 (121) |
| 41 | 3 (115) |
| 42 | 27 (132) |
| 43 | 220 (170) |
| 44 | 470 (165) |
| 45 | 230 (155) |
| 46 | 6 (95) |
| 47 | 25 (94) |
| 48 | 95 (87) |
| 49 | 12 (69) |
|  | 120 (130) |
| 50 | 40 (66) |
|  | 40 (191) |
| 51 | 11 (129) |
| 52 | 120 (147) |
| 53 | 1710 (180) |
| 54 | 5 (187) |
| 55 | 430 (174) |
| 56 | 150 (189) |
| 57 | 3600 (139) |
| 58 | 1400 (212) |
| 59 | 29 (245) |
| 60 | 770 (298) |
| 61 | 49 (218) |
| 62 | 98 (254) |
| 63 | 4020 (134) |
| 64 | 1630 (141) |
| 65 | 120 (113) |
| 66 | 3070 (192) |
| 67 | 3 (192) |
| 68 | 150 (208) |
| 69 | 8 (134) |
| 70 | 88 (142) |
| 71 | 2 (158) |
| 72 | 2 (159) |
| 73 | 6 (148) |
| 74 | 112 (213) |
| 75 | 1 (142) |
| 76 | 2 (124) |
| 77 | 0.5 (128) |
| 78 | 7 (141) |
| 79 | 38 (133) |
| 80 | 15 (99) |
| 81 | 780 (136) |
| 82 | 280 (130) |
| 83 | 0.1 (160) |
|  | 0.1 (196) |
| 84 | 0.6 (170) |
|  | 1 (183) |
| 85 | 1 (151) |
| 86 | 61 (155) |
| 87 | 0.5 (159) |
|  | 0.6 (186) |
| 88 | 0.6 (98) |
|  | 0.4 (170) |
| 89 | 7 (203) |
| 90 | 0.1 (183) |
|  | 0.2 (88) |
| 91 | 4 (185) |
| 92 | 0.3 (172) |
| 93 | 58 (186) |
| 94 | 14 (150) |
| 95 | 396 (159) |
| 96 | 0.3 (220) |
|  | 0.2 (77) |
| 97 | 41 (185) |
| 98 | 2 (191) |
| 99 | 5 (187) |
| 100 | 36 (159) |
| 101 | 63 (159) |
| 102 | 2 (122) |
| 103 | 16 (114) |
| 104 | 15 (107) |
| 105 | 0.3 (74) |
| 106 | 0.1 (155) |
| 107 | 36 (104) |
| 108 | 6 (141) |
| 109 | 0.6 (165) |
| 110 | 6 (131) |
| 111 | 1 (175) |
| 112 | 13 (197) |
| 113 | 0.6 (126) |
| 114 | 4 (143) |
| 115 | 30 (149) |
| 116 | 0.3 (136) |
|  | 0.8 (295) |
| 117 | 0.1 (129) |
| 118 | 0.5 (133) |
| 119 | 0.6 (133) |
| 120 | 0.2 (169) |
| 121 | 4 (172) |
| 122 | 7 (172) |
| 123 | 0.4 (272) |
| 124 | 25 (231) |
| 125 | 0.2 (230) |
| 126 | 0.3 (295) |
| 127 | 0.5 (296) |
|  | 7 (293) |
| 128 | 52 (288) |
| 129 | 20 (478) |
|  | 10 (158) |
| 130 | 9 (373) |
| 131 | 33 (377) |
|  | 86 (273) |
| 132 | 49 (364) |
| 133 | 14 (397) |
| 134 | 9 (394) |
| 135 | 9 +/− 1 (319 +/− 87) (n = 4) |
| 136 | 26 (309) |
| 137 | 16 (271) |
| 138 | 47 (310) |
|  | 0.9 (269) |
| 139 | 450 (320) |
|  | 2 (218) |
| 140 | 21 (227) |
| 141 | 2 (229) |
| 142 | 6 (239) |
| 143 | 3 (230) |
| 144 | 0.9 (210) |
| 145 | 95 (257) |
| 146 | 88 (278) |
| 147 | 15 (267) |
| 148 | 1 (158) |
| 149 | 6 (170) |
| 150 | 14 (137) |
| 151 | 6 (161) |
| 152 | 9 (223) |
| 153 | 7 (234) |
| 154 | 0.7 (256) |
| 155 | 60 (131) |
| 156 | 2 (229) |
| 157 | 0.6 (141) |
| 158 | 0.5 (130) |
| 159 | 10 (180) |
| 160 | 0.1 (191) |
| 161 | 15 (155) |
| 162 | 0.7 (191) |
| 163 | 3 (196) |
| 164 | 11 (194) |
| 165 | 18 (218) |
| 166 | 13 (207) |
| 167 | 117 (156) |
| 168 | 0.3 (173) |

TABLE 2-continued

| Compound | α2β1γ2 AMPK EC$_{50}$ (nM) (Emax %) |
|---|---|
| 169 | 0.1 (172) |
| 170 | 6 (181) |
| 171 | 6 (197) |
| 173 | 1 (181) |
| 174 | 1 (185) |
| 175 | 2 (198) |

The compounds according to the invention may be used for the preparation of drugs, in particular medicaments for activating AMP-activated protein kinase (AMPK).

Thus, according to another of its aspects, a subject of the invention is drugs that comprise a compound of formula (I), or an addition salt of the compound of formula (I) with a pharmaceutically acceptable acid or base.

These drugs find their use in therapeutics, especially in the prevention or the treatment of metabolic disorders including obesity and type 2 diabetes.

These drugs also find their use in therapeutics in the treatment of kidney diseases.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the mode of administration desired, from the usual excipients which are known to those skilled in the art.

In the pharmaceutical compositions of the present invention for oral, sublingual, subcutaneous, intramuscular, intravenous, topical, local, intratracheal, intranasal, transdermal or rectal administration, the active ingredient of formula (I) above, or its salt, can be administered in unit administration form, as a mixture with conventional pharmaceutical excipients, to animals or to human beings for the treatment of the above disorders or diseases.

The appropriate unit administration forms include oral-route forms such as tablets, soft or hard gel capsules, powders, granules and oral solutions or suspensions, sublingual, buccal, intratracheal, intraocular and intranasal administration forms, inhalation forms, topical, transdermal, subcutaneous, intramuscular or intravenous administration forms, rectal administration forms and implants. For topical application, the compounds according to the invention can be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

There may be particular cases where higher or lower dosages are appropriate; such dosages do not depart from the context of the invention. According to the usual practice, the dosage appropriate for each patient is determined by the physician according to the method of administration and the weight and response of said patient.

According to another of its aspects, the present invention also relates to a method for treating the pathological conditions indicated above, which comprises the administration, to a patient, of an effective dose of a compound according to the invention, or a pharmaceutically acceptable salt thereof.

The invention claimed is:

1. A compound corresponding to formula (I):

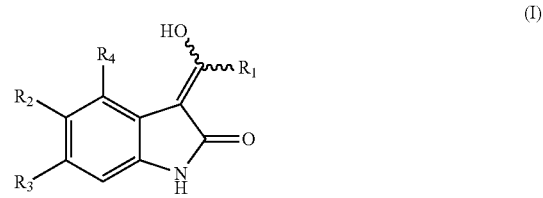

(I)

wherein
R$_1$ is selected from:
(1) an (C$_6$-C$_{10}$)aryl group, unsubstituted or substituted with one or more substituents independently selected from
(a) a halogen atom,
(b) a —OR$_a$ group, in which R$_a$ is selected from a hydrogen atom, a (C$_1$-C$_3$)alkyl group and a —CF$_3$ group,
(c) a (C$_1$-C$_3$)alkyl group, unsubstituted or substituted with one or more halogen atoms,
(d) a carboxyl group,
(e) a cyano group, and
(f) a (C$_3$-C$_6$)heterocycloalkyl group, unsubstituted or substituted with one or more (C$_1$-C$_3$)alkyl group, and
(2) a (C$_2$-C$_{10}$)heteroaryl group, unsubstituted or substituted with one or more substituents independently selected from
(a) a halogen atom,
(b) a (C$_1$-C$_4$)alkyl group,
(c) a (C$_3$-C$_6$)cycloalkyl group,
(d) a —OR$_e$ group, in which R$_e$ is a hydrogen atom or a (C$_1$-C$_4$)alkyl group, said (C$_1$-C$_4$)alkyl group being unsubstituted or substituted with one or more substituents independently selected from (C$_1$-C$_4$)alkoxy group and (C$_3$-C$_6$)heterocycloalkyl group, and
(e) a —NR$_f$R$_{f'}$ group, in which R$_f$ and R$_{f'}$, independently, identical or different, represent a (C$_1$-C$_3$) alkyl group;
R$_2$ is selected from:
(1) an (C$_6$-C$_{10}$)aryl group, unsubstituted or substituted with one or more substituents independently selected from:
(a) a halogen atom,
(b) a cyano group,
(c) a group of formula

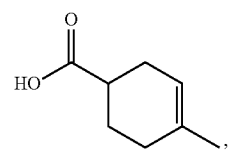

, (d) a group of formula

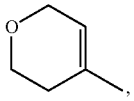

(e) a ($C_1$-$C_3$)alkyl group unsubstituted or substituted with one or more substituents independently selected from a halogen atom, a hydroxyl group and a ($C_1$-$C_4$)alkenyl group,
(f) a ($C_3$-$C_6$)cycloalkyl group, unsubstituted or substituted with a substituent selected from a hydroxy ($C_1$-$C_3$)alkyl group, a hydroxy group and an ($C_1$-$C_4$)alkoxy group,
(g) a —$OR_b$ group, in which $R_b$ is selected from
  (i) a hydrogen atom,
  (ii) a —$CF_3$ group,
  (iii) a ($C_3$-$C_6$)cycloalkyl group, unsubstituted or substituted with a hydroxyl group,
  (iv) a ($C_3$-$C_6$)heterocycloalkyl group, said ($C_3$-$C_6$) heterocycloalkyl being unsubstituted or substituted with a ($C_1$-$C_3$)alkyl group, and
  (v) an ($C_1$-$C_3$)alkyl group, said ($C_1$-$C_3$)alkyl group being unsubstituted or substituted with one or more independently selected from:
    (aa) hydroxyl group,
    (bb) ($C_1$-$C_4$)alkoxy group,
    (cc) ($C_2$-$C_{10}$)heteroaryl group,
    (dd) acetamido group,
    (ee) di($C_1$-$C_3$)alkyl-amino group,
    (ff) ($C_3$-$C_6$)cycloalkyl group, said ($C_3$-$C_6$)cycloalkyl group being unsubstituted or substituted with one or more hydroxyl group, and
    (gg) ($C_3$-$C_6$)heterocycloalkyl group, said ($C_3$-$C_6$)heterocycloalkyl group being unsubstituted or substituted with a ($C_1$-$C_3$)alkyl group;
(h) a ($C_3$-$C_6$)heterocycloalkyl group unsubstituted or substituted with one or more substituents independently selected from halogen atom, ($C_1$-$C_3$)alkyl group, hydroxyl group, hydroxy($C_1$-$C_3$)alkyl group, ($C_1$-$C_4$)alkoxy group and ($C_1$-$C_4$)fluoroalkyl group,
(i) an ($C_6$-$C_{10}$)aryl group, unsubstituted or substituted with one or more —$OR_c$ group, in which $R_c$ is a hydrogen atom or a ($C_1$-$C_3$)alkyl group,
(j) a ($C_2$-$C_{10}$)heteroaryl group, unsubstituted or substituted with one or more —$NH_2$ group, and
(k) a —$NR_dR_{d'}$ group, in which $R_d$ and $R_{d'}$, independently, identical or different, represent a hydrogen atom, a ($C_1$-$C_3$)alkyl group, a hydroxy ($C_1$-$C_4$)alkyl or a ($C_3$-$C_6$)cycloalkyl group, and
(2) a ($C_2$-$C_{10}$)heteroaryl group, unsubstituted or substituted with one or more substituents independently selected from:
  (a) a ($C_1$-$C_3$)alkyl group,
  (b) a ($C_3$-$C_6$)cycloalkyl group, unsubstituted or substituted with a hydroxy($C_1$-$C_3$)alkyl group, and
  (c) a —$NR_gR_{g'}$ group, in which $R_g$ and $R_{g'}$, independently, identical or different, represent a ($C_1$-$C_3$) alkyl group,
$R_3$ is selected from:
  a halogen atom, and
  a ($C_1$-$C_3$)alkyl group,
and
$R_4$ is selected from:
  a halogen atom, and
  a hydrogen atom,
or a pharmaceutically acceptable salt of this compound.

2. The compound of formula (I) as claimed in claim 1, wherein:
$R_1$ is selected from:
  (1) An ($C_6$-$C_{10}$)aryl group, unsubstituted or substituted with one or more substituents independently selected from
    (a) a halogen atom,
    (b) a —$OR_a$ group, in which $R_a$ is a hydrogen atom or a ($C_1$-$C_3$)alkyl group,
    (c) a ($C_1$-$C_3$)alkyl group, unsubstituted or substituted with one or more halogen atoms,
    (d) a carboxyl group, and
    (e) a cyano group, and
  (2) a ($C_2$-$C_{10}$)heteroaryl group, unsubstituted or substituted with one or more substituents independently selected from a halogen atom, a ($C_1$-$C_4$)alkyl group, a ($C_3$-$C_6$)cycloalkyl group, and a ($C_1$-$C_4$)alkoxy group,
$R_2$ is selected from:
  (1) an ($C_6$-$C_{10}$)aryl group, unsubstituted or substituted with one or more substituents independently selected from:
    (a) a halogen atom,
    (b) a cyano group,
    (c) a ($C_1$-$C_3$)alkyl group,
    (d) a ($C_3$-$C_6$)cycloalkyl group, unsubstituted or substituted with a hydroxy($C_1$-$C_3$)alkyl group,
    (e) a —$OR_b$ group, in which $R_b$ is a hydrogen atom, a —$CF_3$ group or an ($C_1$-$C_3$)alkyl group, wherein said ($C_1$-$C_3$)alkyl group is unsubstituted or substituted with one ($C_3$-$C_6$)heterocycloalkyl group, said ($C_3$-$C_6$)heterocycloalkyl group being unsubstituted or substituted with a ($C_1$-$C_3$)alkyl group;
    (f) a ($C_3$-$C_6$)heterocycloalkyl group, unsubstituted or substituted with one or more ($C_1$-$C_3$)alkyl group,
    (g) an ($C_6$-$C_{10}$)aryl group, unsubstituted or substituted with one or more —$OR_c$group, wherein $R_c$ is a hydrogen atom or a ($C_1$-$C_3$)alkyl group,
    (h) a ($C_2$-$C_{10}$)heteroaryl group, unsubstituted or substituted with one or more —$NH_2$ group, and
    (i) a —$NR_dR_{d'}$ group, in which $R_d$ and $R_{d'}$, independently, identical or different, represent a hydrogen atom, or a ($C_1$-$C_3$)alkyl group, and
  (2) a ($C_2$-$C_{10}$)heteroaryl group, unsubstituted or substituted with one or more ($C_3$-$C_6$)cycloalkyl group, wherein the ($C_3$-$C_6$)cycloalkyl group is unsubstituted or substituted with a hydroxy($C_1$-$C_3$)alkyl group,
$R_3$ is selected from:
  a halogen atom, and
  a ($C_1$-$C_3$)alkyl group,
  and
$R_4$ is a hydrogen atom,
or a pharmaceutically acceptable salt of this compound.

3. The compound of formula (I) as claimed in claim 1, wherein:
$R_1$ is selected from:
  (1) a phenyl group, unsubstituted or substituted with one or more substituents independently selected from:

(a) a fluorine atom or a chlorine atom,
(b) a —$OR_a$ group, in which $R_a$ is a methyl group, or a $CF_3$ group,
(c) a di or trifluoro-methyl group,
(d) a carboxyl group,
(e) a cyano group,
(f) a morpholine group, and (g) a methylpiperazine group; and
(2) ($C_2$-$C_{10}$)heteroaryl group selected from a pyridinyl group, a pyrazolyl group, a pyrimidinyl group, an isoxazolyl group, a thiazolyl group, an isothiazolyl group, a 1,3,4-oxadiazolyle group, a thiazol-2onyl group, a thienyl group, a furyl group, a furopyridinyl group, a benzofuran-2-yl group, a thienopyridinyl group, and an indolynonyl group, each of which is unsubstituted or substituted with one or more substituents independently selected from:
(a) a bromine atom, a chlorine atom, a fluorine atom,
(b) a methyl or tert-butyl group,
(c) a hydroxyl group,
(d) a cyclopropyl group, or a cyclohexyl group,
(e) a —$OR_e$ group, in which $R_e$ is a methyl group, an ethyl group, an isopropyl group, a methoxyethyl group, or a morpholinoethyl group, and
(f) a dimethylamino group,
$R_2$ is selected from:
(1) a phenyl or a naphthalene group, each of which is unsubstituted or substituted with one or more substituents independently selected from:
(a) a fluorine atom or a chlorine atom,
(b) a group of formula

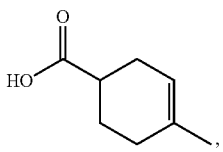
, (c) a group of formula

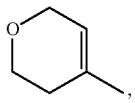
, (d) a cyano group,
(e) an ethyl group, unsubstituted or substituted with one or two hydroxyl groups,
(f) a propyl group, unsubstituted or substituted with two or more groups independently selected from a chlorine atom, a hydroxyl group and a propenyl group,
(g) a cyclopropyl or a cyclobutyl group, unsubstituted or substituted with a hydroxyl group, a hydroxymethyl group or a methoxy group,
(h) a —$OR_b$ group, in which $R_b$ is a hydrogen atom, a —$CF_3$ group or an ($C_1$-$C_3$)alkyl group, wherein the ($C_1$-$C_3$)alkyl group is unsubstituted or substituted with one piperazinyl group, said piperazinyl group being unsubstituted or substituted with a methyl group;
(i) a morpholinyl, a dihydropyranyl, a tetrahydropyranyl, a pyrrolidinyle, a tetrahydrofuranyl, a piperazinyl, a piperidinyl group, a dioxane group, or an oxaazaspiro[3.3]heptanyl, each of which is unsubstituted or substituted with one or more substituents independently selected from methyl group, hydroxyl group, methoxy group, hydroxymethyl group and fluorine atom,
(j) an azetidinyl group unsubstituted or substituted with one or two sub stituents independently selected from fluorine atom, methyl group, and hydroxymethyl group,
(k) a pyrrolidinyl group substituted with a trifluoroethyl group,
(l) a phenyl group, unsubstituted or substituted with one or more —$OR_c$ group, in which $R_c$ is selected from:
(i) a hydrogen atom,
(ii) a methyl group,
(iii) a hydroxypropyl group,
(iv) a hydroxycyclohexyl group,
(v) a methoxypropyl group,
(vi) a dimethylaminopropyl group,
(vii) a morpholinoethyl group, (viii) a morpholinopropyl group,
(ix) a hydroxypropyl group, (x) a methoxyethyl group,
(xi) a tetrahydropyranyl,
(xii) a pyridylmethyl group,
(xiii) a pyrimidinyl group,
(xiv) a methylpiperidyl group,
(xv) a thiazolylmethyl group,
(xvi) an acetamidoethyl group,
(xvii) an oxetanylmethyl group, and
(xviii) an hydroxycyclobutylmethyl group,
(m) a pyridinyl, a thiazolyl, or a furanyl group, each of which is unsubstituted or substituted with one —$NH_2$ group, and
(n) a —$NR_dR_{d'}$ group, in which $R_d$ and $R_{d'}$, independently, identical or different, represent a methyl group, a hydroxypropyl group or a cyclopropyl group,
(2) a thiophene group, unsubstituted or substituted with a cyclopropyl group, wherein the cyclopropyl group is unsubstituted or substituted with a hydroxymethyl group,
(3) a pyrimidinyl or a pyridinyl group substituted with a dimethylamino group, and
(4) an indolyl group, substituted with a methyl group,
$R_3$ is selected from:
a chlorine atom, a fluorine atom, and
a methyl group, and
$R_4$ is a fluorine or a hydrogen atom;
or a pharmaceutically acceptable salt of this compound.

4. The compound of formula (I) as claimed in claim 1, wherein:
$R_1$ is a ($C_2$-$C_{10}$)heteroaryl group, unsubstituted or substituted with one or more substituents independently selected from a halogen atom, a ($C_1$-$C_3$)alkyl group, a ($C_3$-$C_5$)cycloalkyl group, and a ($C_1$-$C_4$)alkoxy group,
or a pharmaceutically acceptable salt of this compound.

5. The compound of formula (I) as claimed in claim 1, wherein:
$R_1$ is an isoxazolyl group, unsubstituted or substituted with one substituent selected from a ($C_1$-$C_4$)alkyl group, a ($C_3$-$C_6$)cycloalkyl group and a ($C_1$-$C_3$)alkoxy group,
or a pharmaceutically acceptable salt of this compound.

6. The compound of formula (I) as claimed in claim 1, wherein:
   $R_1$ is a phenyl group, substituted with one substituent selected from a halogen atom and an a —$OR_a$ group, wherein $R_a$ is a ($C_1$-$C_3$)alkyl group, or a pharmaceutically acceptable salt of this compound.

7. The compound of formula (I) as claimed in claim 1, wherein:
   $R_2$ is:
      an ($C_6$-$C_{10}$)aryl group, unsubstituted or substituted with one or more substituents independently selected from:
      (a) a ($C_1$-$C_3$)alkyl group,
      (b) a ($C_3$-$C_6$)cycloalkyl group, unsubstituted or substituted with a hydroxy($C_1$-$C_3$)alkyl group,
      (c) a ($C_3$-$C_6$)heterocycloalkyl group, unsubstituted or substituted with one or more substituents independently selected from ($C_1$-$C_3$)alkyl group and hydroxyl group,
      (d) an ($C_6$-$C_{10}$)aryl group, unsubstituted or substituted with one or more —$OR_c$ group, wherein $R_c$ is selected from a hydrogen atom and a ($C_1$-$C_3$)alkyl group,
      (e) a ($C_2$-$C_{10}$)heteroaryl group, unsubstituted or substituted with one or more —$NH_2$ group, and
      (f) a —$NR_dR_{d'}$ group, in which $R_d$ and $R_{d'}$, independently, identical or different, represent a hydrogen atom, or a ($C_1$-$C_3$)alkyl group,
   or a pharmaceutically acceptable salt of this compound.

8. The compound of formula (I) as claimed in claim 1, wherein:
   $R_2$ is:
      a phenyl group, unsubstituted or substituted with one substituent selected from:
      (a) a halogen atom,
      (b) a ($C_3$-$C_6$)cycloalkyl group, unsubstituted or substituted with one or more hydroxy($C_3$-$C_3$)alkyl group,
      (c) a ($C_3$-$C_6$)heterocycloalkyl group, unsubstituted or substituted with one or more substituents independently selected from ($C_1$-$C_3$)alkyl group and hydroxyl group,
      (d) an phenyl group, unsubstituted or substituted with one or more —$OR_c$ group, wherein $R_c$ is selected from a hydrogen atom and a ($C_1$-$C_3$)alkyl group,
      (e) a pyridinyl group, and
      (f) a —$NR_dR_{d'}$ group, in which $R_d$ and $R_{d'}$, identical, represent a ($C_1$-$C_3$)alkyl group,
   or a pharmaceutically acceptable salt of this compound.

9. The compound of formula (I) as claimed in claim 1, wherein $R_3$ is a chlorine or a fluorine atom, or a pharmaceutically acceptable salt of this compound.

10. The compound of formula (I) as claimed in claim 1, wherein $R_4$ is a fluorine atom, or a pharmaceutically acceptable salt of this compound.

11. The compound as claimed in claim 1, selected from:
   6-Chloro-5-(4-dimethylamino-phenyl)-3-[hydroxy-1-(3-methyl-isoxazol-5-yl)-methylidene]-1,3-dihydro-indol-2-one;
   6-Chloro-3-[1hydroxy-1-(3-hydroxy-phenyl)-methylidene]-5-(4-morpholin-4-yl-phenyl)-1,3-dihydro-indol-2-one, sodium salt;
   6-Chloro-3-[1hydroxy-1-(3-hydroxy-phenyl)-methylidene]-5-(4-morpholin-4-yl-phenyl)-1,3-dihydro-indol-2-one;
   3-{[6-Chloro-5-(4-morpholin-4-yl-phenyl)-2-oxo-1,2-dihydro-indolylidene]-hydroxy-methyl}-benzoic acid;
   6-Chloro-5-(2'-hydroxy-3'-methoxy-biphenyl-4-yl)-3-[1-hydroxy-1-(3-methoxy-isoxazol-5-yl)-methylidene]-1,3-dihydro-indol-2-one;
   6-Chloro-5-[4-(1-hydroxymethyl-cyclopropyl)-phenyl]-3-[1-hydroxy-1-(3-methyl-isoxazol-5-yl)-methylidene]-1,3-dihydro-indol-2-one;
   5-Biphenyl-4-yl-6-chloro-3-[1-hydroxy-1-phenyl-methylidene]-1,3-dihydro-indol-2-one;
   3-{[6-Chloro-5-(4-dimethylamino-phenyl)-2-oxo-1,2-dihydro-indolylidene]-hydroxy-methyl}-benzoic acid;
   4-{[6-Chloro-5-(4-dimethylamino-phenyl)-2-oxo-1,2-dihydro-indolylidene]-hydroxy-methyl}-benzoic acid;
   6-Chloro-5-(4-dimethylamino-phenyl)-3-[1-hydroxy-1-(2-methyl-thiazol-5-yl)-methylidene]-1,3-dihydro-indol-2-one;
   6-Chloro-3-[1-(3-fluoro-phenyl)-1-hydroxy-methylidene]-5-naphthalen-2-yl-1,3-dihydro-indol-2-one;
   6-Chloro-5-(2'-hydroxy-3'-methoxy-biphenyl-4-yl)-3-[1-hydroxy-1-(3-methyl-isoxazol-5-yl)-methylidene]-1,3-dihydro-indol-2-one;
   6-Chloro-3-[1-hydroxy-1-(3-methyl-isothiazol-5-yl)-methylidene]-5-(4-morpholin-4-yl-phenyl)-1,3-dihydro-indol-2-one;
   6-Chloro-3-[1-hydroxy-1-(3-methyl-isoxazol-5-yl)-methylidene]-5-(4-morpholin-4-yl-phenyl)-1,3-dihydro-indol-2-one;
   6-Chloro-3-[1-(2,4-dimethyl-thiazol-5-yl)-1-hydroxy-methylidene]-5-(4-morpholin-4-yl-phenyl)-1,3-dihydro-indol-2-one;
   6-Chloro-3-[1-hydroxy-1-(5-methyl-[1,3,4]oxadiazol-2-yl)-methylidene]-5-(4-morpholin-4-yl-phenyl)-1,3-dihydro-indol-2-one;
   6-Chloro-3-[1-hydroxy-1-(3-methoxy-isoxazol-5-yl)-methylidene]-5-(4-morpholin-4-yl-phenyl)-1,3-dihydro-indol-2-one;
   3-{[6-Chloro-5-(4-morpholin-4-yl-phenyl)-2-oxo-1,2-dihydro-indolylidene]-hydroxy-methyl}-benzonitrile;
   6-Chloro-3-[1-(3-fluoro-phenyl)-1-hydroxy-methylidene]-5-(4-morpholin-4-yl-phenyl)-1,3-dihydro-indol-2-one;
   6-Chloro-3-[1-hydroxy-1-(3-methyl-isoxazol-5-yl)-methylidene]-5-(4-methoxy-phenyl)-1,3-dihydro-indol-2-one;
   6-Chloro-5-[4-(3,6-dihydro-2H-pyran-4-yl)-phenyl]-3-[1-hydroxy-1-(3-methyl-isoxazol-5-yl)-methylidene]-1,3-dihydro-indol-2-one;
   6-Chloro-5-(4-cyclopropyl-phenyl)-3-[1-hydroxy-1-(3-methyl-isoxazol-5-yl)-methylidene]-1,3-dihydro-indol-2-one;
   6-Chloro-5-[4-(1-hydroxymethyl-cyclopropyl)-phenyl]-3-[1-hydroxy-1-(3-methyl-isothiazol-5-yl)-methylidene]-1,3-dihydro-indol-2-one;
   6-Chloro-3-[1-hydroxy-1-(3-methyl-isoxazol-5-yl)-methylidene]-5-(4-pyrrolidin-1-yl-phenyl)-1,3-dihydro-indol-2-one;
   6-Chloro-3-[1-hydroxy-1-pyridin-3-yl-methylidene]-5-(4-morpholin-4-yl-phenyl)-1,3-dihydro-indol-2-one;
   6-Chloro-5-(4-cyclopropyl-phenyl)-3-[1-(3-fluoro-phenyl)-1-hydroxy-methylidene]-1,3-dihydro-indol-2-one;
   6-Chloro-3-[1-(3-fluoro-phenyl)-1-hydroxy-methylidene]-5-[4-(1-hydroxymethyl-cyclopropyl)-phenyl]-1,3-dihydro-indol-2-one;

6-Chloro-3-[1-hydroxy-1-(5-methyl-isoxazol-3-yl)-methylidene]-5-(4-morpholin-4-yl-phenyl)-1,3-dihydro-indol-2-one;
6-Fluoro-3-[1-hydroxy-1-(3-methyl-isoxazol-5-yl)-methylidene]-5-(4-morpholin-4-yl-phenyl)-1,3-dihydro-indol-2-one;
6-Chloro-5-(4-fluoro-phenyl)-3-[1-hydroxy-1-(3-methyl-isoxazol-5-yl)-methylidene]-1,3-dihydro-indol-2-one;
3-[1-Hydroxy-1-(3-methyl-isoxazol-5-yl)-methylidene]-6-methyl-5-(4-morpholin-4-yl-phenyl)-1,3-dihydro-indol-2-one;
6-Chloro-3-[1(2-fluoro-phenyl)-1-hydroxy-methylidene]-5-(4-morpholin-4-yl-phenyl)-1,3-dihydro-indol-2-one;
6-Chloro-3-[1-hydroxy-1-(3-methyl-isoxazol-5-yl)-methylidene]-5-(4-hydroxy-phenyl)-1,3-dihydro-indol-2-one;
6-Chloro-3-[1(3-chloro-phenyl)-1-hydroxy-methylidene]-5-(4-morpholin-4-yl-phenyl)-1,3-dihydro-indol-2-one;
6-Chloro-3-[1-hydroxy-1-(3-methyl-isoxazol-5-yl)-methylidene]-5-(4-pyridin-4-yl-phenyl)-1,3-dihydro-indol-2-one, hydrochloride;
6-Chloro-3-[1-(4-fluoro-phenyl)-1-hydroxy-methylidene]-5-(4-morpholin-4-yl-phenyl)-1,3-dihydro-indol-2-one;
5-[4-(2-Amino-thiazol-4-yl)-phenyl]-6-chloro-3-[1-hydroxy-1-(3-methyl-isoxazol-5-yl)-methylidene]-1,3-dihydro-indol-2-one;
4-{6-Chloro-3-[1-hydroxy-1-(3-methyl-isoxazol-5-yl)-methylidene]-2-oxo-2,3-dihydro-1H-indol-5-yl}-benzonitrile;
6-Chloro-3-[1-(3-difluoromethyl-phenyl)-1-hydroxy-methylidene]-5-(4-morpholin-4-yl-phenyl)-1,3-dihydro-indol-2-one;
6-Chloro-3-[1-hydroxy-1-(3-trifluoromethyl-phenyl)-methylidene]-5-(4-morpholin-4-yl-phenyl)-1,3-dihydro-indol-2-one;
3-[1-(3-Bromo-isoxazol-5-yl)-1-hydroxy-methylidene]-6-chloro-5-(4-morpholin-4-yl-phenyl)-1,3-dihydro-indol-2-one;
6-Chloro-5-(2'-hydroxy-3'-methoxy-biphenyl-4-yl)-3-[1-hydroxy-1-(3-methyl-isothiazol-5-yl)-methylidene]-1,3-dihydro-indol-2-one;
6-Chloro-3-[1-hydroxy-1-phenyl-methylidene]-5-(4-morpholin-4-yl-phenyl)-1,3-dihydro-indol-2-one;
6-Chloro-5-(3-fluoro-4-hydroxy-phenyl)-3-[1-hydroxy-1-(3-methyl-isoxazol-5-yl)-methylidene]-1,3-dihydro-indol-2-one;
6-Chloro-5-[5-(1-hydroxymethyl-cyclopropyl)-thiophen-2-yl]-3-[1-hydroxy-1-(3-methyl-isoxazol-5-yl)-methylidene]-1,3-dihydro-indol-2-one;
6-Chloro-3-[1-(2-fluoro-phenyl)-1-hydroxy-methylidene]-5-[4-(1-hydroxymethyl-cyclopropyl)-phenyl]-1,3-dihydro-indol-2-one;
6-Chloro-3-[1-(2-fluoro-phenyl)-1-hydroxy-methylidene]-5-[4-(1-hydroxymethyl-cyclopropyl)-phenyl]-1,3-dihydro-indol-2-one, sodium salt;
6-Chloro-5-[4-(3,6-dihydro-2H-pyran-4-yl)-phenyl]-3-[1-hydroxy-1-(3-methyl-isothiazol-5-yl)-methylidene]-1,3-dihydro-indol-2-one;
6-Chloro-5-[4-(1-hydroxymethyl-cyclobutyl)-phenyl]-3-[1-hydroxy-1-(3-methyl-isoxazol-5-yl)-methylidene]-1,3-dihydro-indol-2-one;
6-Chloro-3-[1-hydroxy-1-(3-methoxy-phenyl)-methylidene]-5-(4-morpholin-4-yl-phenyl)-1,3-dihydro-indol-2-one;
6-Chloro-5-(2'-hydroxy-3'-methoxy-biphenyl-4-yl)-3-[1-hydroxy-1-(2-methyl-thiazol-5-yl)-methylidene]-1,3-dihydro-indol-2-one;
6-Chloro-5-[4-(3,6-dihydro-2H-pyran-4-yl)-phenyl]-3-[1-(3-fluoro-phenyl)-1-hydroxy-methylidene]-1,3-dihydro-indol-2-one;
6-Chloro-3-[1-hydroxy-1-(1-methyl-1H-pyrazol-3-yl)-methylidene]-5-(4-morpholin-4-yl-phenyl)-1,3-dihydro-indol-2-one;
6-Chloro-3-[1-hydroxy-1-(3-methoxy-isoxazol-5-yl)-methylidene]-5-[4-(1-hydroxymethyl-cyclopropyl)-phenyl]-1,3-dihydro-indol-2-one;
6-Chloro-5-(3-fluoro-4-methoxy-phenyl)-3-[1-hydroxy-1-(3-methyl-isoxazol-5-yl)-methylidene]-1,3-dihydro-indol-2-one;
6-Chloro-5-(4-fluoro-2-hydroxy-phenyl)-3-[1-hydroxy-1-(3-methyl-isoxazol-5-yl)-methylidene]-1,3-dihydro-indol-2-one;
6-Chloro-3-[1-hydroxy-1-(2-methyl-thiazol-4-yl)-methylidene]-5-(4-morpholin-4-yl-phenyl)-1,3-dihydro-indol-2-one;
6-Chloro-3-[1-hydroxy-1-(3-methyl-isoxazol-5-yl)-methylidene]-5-(4-trifluoromethoxy-phenyl)-1,3-dihydro-indol-2-one;
6-Chloro-3-[1-hydroxy-1-isoxazol-5-yl-methylidene]-5-(4-morpholin-4-yl-phenyl)-1,3-dihydro-indol-2-one;
6-Chloro-3-[1-hydroxy-1-(3-methyl-isoxazol-4-yl)-methylidene]-5-(4-morpholin-4-yl-phenyl)-1,3-dihydro-indol-2-one;
6-Chloro-3-[1-hydroxy-1-(3-methyl-isoxazol-5-yl)-methylidene]-5-[4(tetrahydro-pyran-4-yl)-phenyl]-1,3-dihydro-indol-2-one;
6-Chloro-3-[1-(5-cyclopropyl-isoxazol-3-yl)-1-hydroxy-methylidene]-5-(4-morpholin-4-yl-phenyl)-1,3-dihydro-indol-2-one;
6-Chloro-5-(4-chloro-phenyl)-3-[1-hydroxy-1-(3-methyl-isoxazol-5-yl)-methylidene]-1,3-dihydro-indol-2-one;
6-Chloro-5-(4-ethyl-phenyl)-3-[1-hydroxy-1-(3-methyl-isoxazol-5-yl)-methylidene]-1,3-dihydro-indol-2-one;
6-Chloro-5-(4-furan-2-yl-phenyl)-3-[1-hydroxy-1-(3-methyl-isoxazol-5-yl)-methylidene]-1,3-dihydro-indol-2-one;
6-Chloro-5-(4-ethoxy-phenyl)-3-[1-hydroxy-1-(3-methyl-isoxazol-5-yl)-methylidene]-1,3-dihydro-indol-2-one;
6-Chloro-5-[4-(3,6-dihydro-2H-pyran-4-yl)-phenyl]-3-[1-hydroxy-1-(3-methoxy-isoxazol-5-yl)-methylidene]-1,3-dihydro-indol-2-one;
6-Chloro-3-[1-hydroxy-1-(3-methyl-isoxazol-5-yl)-methylidene]-5-[4-(tetrahydro-furan-2-yl)-phenyl]-1,3-dihydro-indol-2-one;
6-Chloro-3-[1-hydroxy-1-(3-methyl-isoxazol-5-yl)-methylidene]-5-[4-(3-piperazin-1-yl-propoxy)-phenyl]-1,3-dihydro-indol-2-one, hydrochloride;
6-Chloro-3-[1-hydroxy-1-(3-methyl-isoxazol-5-yl)-methylidene]-5-{4-[3-(4-methyl-piperazin-1-yl)-propoxy]-phenyl}-1,3-dihydro-indol-2-one, hydrochloride;
6-Fluoro-5-(2'-hydroxy-3'-methoxy-biphenyl-4-yl)-3-[1-hydroxy-1-(3-methoxy-isoxazol-5-yl)-methylidene]-1,3-dihydro-indol-2-one;
6-Fluoro-5-[4-(1-hydroxymethyl-cyclopropyl)-phenyl]-3-[1-hydroxy-1-(3-methyl-isoxazol-5-yl)-methylidene]-1,3-dihydro-indol-2-one;
3-[1-(3-Bromo-isoxazol-5-yl)-1-hydroxy-methylidene]-6-chloro-5-[4-(1-hydroxymethyl-cyclopropyl)-phenyl]-1,3-dihydro-indol-2-one;

6-Chloro-3-[1-hydroxy-1-(3-methyl-isoxazol-5-yl)-methylidene]-5-[4-(4-methyl-piperazin-1-yl)-phenyl]-1,3-dihydro-indol-2-one, hydrochloride;

6-Chloro-5-[4-(1-hydroxymethyl-cyclopropyl)-phenyl]-3-[1-hydroxy-1-(2-methyl-thiazol-5-yl)-methylidene]-1,3-dihydro-indol-2-one;

3-[1-(3-tert-Butyl-isoxazol-5-yl)-1-hydroxy-methylidene]-6-chloro-5-[4-(1-hydroxymethyl-cyclopropyl)-phenyl]-1,3-dihydro-indol-2-one;

6-Chloro-3-[1-(3-fluoro-4-methoxy-phenyl)-1-hydroxymethylidene]-5-(4-morpholin-4-yl-phenyl)-1,3-dihydro-indol-2-one;

6-Chloro-3-[1-hydroxy-1-(3-methyl-isoxazol-5-yl)-methylidene]-5-[4-(1-methyl-piperidin-4-yl)-phenyl]-1,3-dihydro-indol-2-one, hydrochloride;

6-chloro-3-[hydroxy-[3-(2-methoxyethoxy)isoxazol-5-yl]methylene]-5-[4-(2-hydroxy-3-methoxy-phenyl)phenyl]indolin-2-one;

6-chloro-5-[4-[1-(chloromethyl)-1,2-dihydroxy-ethyl]phenyl]-3-[hydroxy-(3-methylisoxazol-5-yl)methylene]indolin-2-one;

6-chloro-5-(4-hydroxy-3-methoxy-phenyl)-3-[hydroxy-(3-methylisoxazol-5-yl)methylene]indolin-2-one;

6-chloro-3-[hydroxy-(3-methylisoxazol-5-yl)methylene]-5-[4-(2-morpholinoethoxy)phenyl]indolin-2-one hydrochloride;

4,6-difluoro-3-[hydroxy-(3-methoxyisoxazol-5-yl)methylene]-5-[4-[1-(hydroxymethyl)cyclopropyl]phenyl]indolin-2-one;

6-chloro-3-[(3-fluoro-4-methoxy-phenyl)-hydroxy-methylene]-5-[4-(2-hydroxy-3-methoxy-phenyl)phenyl]indolin-2-one;

6-chloro-5-[2-fluoro-4-[1-(hydroxymethyl)cyclopropyl]phenyl]-3-[hydroxy-(3-methylisoxazol-5-yl)methylene]indolin-2-one;

6-chloro-3-[(3-cyclohexylisoxazol-5-yl)-hydroxy-methylene]-5-(4-morpholinophenyl)indolin-2-one;

6-chloro-3-[(3-cyclopropylisoxazol-5-yl)-hydroxy-methylene]-5-(4-morpholinophenyl)indolin-2-one;

6-chloro-3-[(3-fluoro-4-methoxy-phenyl)-hydroxy-methylene]-5-[4-[1-(hydroxymethyl)cyclopropyl]phenyl]indolin-2-one;

6-chloro-3-[hydroxy-(3-methoxyisoxazol-5-yl)methylene]-5-[4-(4-hydroxytetrahydropyran-4-yl)phenyl]indolin-2-one;

6-chloro-5-[4-(2-hydroxy-3-methoxy-phenyl)phenyl]-3-[hydroxy-[3-(2-morpholinoethoxy)isoxazol-5-yl]methylene]indolin-2-one;

6-chloro-3-[hydroxy-(3-methylisoxazol-5-yl)methylene]-5-[4-(3-hydroxypropoxy)phenyl]indolin-2-one;

4,6-difluoro-3-[hydroxy-(3-methoxyisoxazol-5-yl)methylene]-5-[4-(2-hydroxy-3-methoxy-phenyl)phenyl]indolin-2-one;

6-chloro-3-[hydroxy-[3-(4-methylpiperazin-1-yl)phenyl]methylene]-5-(4-morpholinophenyl)indolin-2-one hydrochloride;

6-chloro-3-[hydroxy-(3-morpholinophenyl)methylene]-5-(4-morpholinophenyl)indolin-2-one;

6-chloro-3-[3-fluoro-4-(trifluoromethoxy)phenyl]-hydroxy-methylene]-5-(4-morpholinophenyl)indolin-2-one;

6-chloro-5-[3-fluoro-4-[1-(hydroxymethyl)cyclopropyl]phenyl]-3-[hydroxy-(3-methoxyisoxazol-5-yl)methylene]indolin-2-one;

6-chloro-3-[(3-chloro-5-fluoro-4-methoxy-phenyl)-hydroxy-methylene]-5-(4-morpholinophenyl)indolin-2-one;

6-chloro-3-[(2,3-difluoro-4-methoxy-phenyl)-hydroxymethylene]-5-(4-morpholinophenyl)indolin-2-one;

6-chloro-3-[hydroxy-(3-methoxyisoxazol-5-yl)methylene]-5-[4-(3-morpholinopropoxy)phenyl]indolin-2-one;

6-chloro-3-[hydroxy-(3-methoxyisoxazol-5-yl)methylene]-5-[4-(3-pyridylmethoxy)phenyl]indolin-2-one;

6-chloro-3-[hydroxy-(3-methylisoxazol-5-yl)methylene]-5-[4-(pyrimidin-2-ylmethoxy)phenyl]indolin-2-one;

6-chloro-3-[hydroxy-(3-hydroxyisoxazol-5-yl)methylene]-5-(4-morphohnophenyl)indolin-2-one;

6-chloro-3-[hydroxy-(3-methylisoxazol-5-yl)methylene]-5-[4-(2-methoxyethoxy)phenyl]indolin-2-one;

N-[2-[4-[6-chloro-3-[hydroxy-(3-methylisoxazol-5-yl)methylene]-2-oxo-indolin-5-yl]phenoxy]ethyl]acetamide;

6-chloro-3-[(3-ethoxyisoxazol-5-yl)-hydroxy-methylene]-5-[4-(2-hydroxy-3-methoxy-phenyl)phenyl]indolin-2-one;

6-chloro-3-[(3-cyclopropylisoxazol-5-yl)-hydroxy-methylene]-5-[4-[1-(hydroxymethyl)cyclopropyl]phenyl]indolin-2-one;

5-[-[6-chloro-5-(4-morphohnophenyl)-2-oxo-indolin-3-ylidene]-hydroxy-methyl]-4-methyl-3H-thiazol-2-one;

6-chloro-3-[(2,5-difluoro-4-methoxy-phenyl)-hydroxymethylene]-5-(4-morphohnophenyl)indolin-2-one;

6-chloro-3-[hydroxy-(3-isopropoxyisoxazol-5-yl)methylene]-5-[4-(2-hydroxy-3-methoxy-phenyl)phenyl]indolin-2-one;

6-chloro-3-[hydroxy-(3-methoxyisoxazol-5-yl)methylene]-5-[4-(1-methoxycyclobutyl)phenyl]indolin-2-one;

6-chloro-5-[2-fluoro-4-[1-(hydroxymethyl)cyclopropyl]phenyl]-3-[hydroxy-(3-methoxyisoxazol-5-yl)methylene]indolin-2-one;

3-[(3-tert-butylisoxazol-5-yl)-hydroxy-methylene]6-chloro-5-(4-morphohnophenyl)indolin-2-one;

6-chloro-3-[(3-cyclopropylisoxazol-5-yl)-hydroxy-methylene]-5-[2-fluoro-4-[1-(hydroxymethyl)cyclopropyl]phenyl]indolin-2-one;

6-chloro-5-[4-[1-(hydroxymethyl)cyclopropyl]phenyl]-3-[hydroxy(2-thienyl)methylene]indolin-2-one;

6-chloro-3-[hydroxy-(3-methylisoxazol-5-yl)methylene]-5-[4-(oxetan-2-ylmethoxy)phenyl]indolin-2-one;

6-chloro-3-[hydroxy-(6-methoxy-3-pyridyl)methylene]-5-[4-[1-(hydroxymethyl)cyclopropyl]phenyl]indolin-2-one hydrochloride;

6-chloro-3-[(3-cyclopropylisoxazol-5-yl)-hydroxy-methylene]-5-[4-(2-hydroxy-3-methoxy-phenyl)phenyl]indolin-2-one;

6-fluoro-3-[hydroxy-(3-methoxyisoxazol-5-yl)methylene]-5-[4-[1-(hydroxymethyl)cyclopropyl]phenyl]indolin-2-one;

3-[(3-cyclopropylisoxazol-5-yl)-hydroxy-methylene]6-fluoro-5-[4-[1-(hydroxymethyl)cyclopropyl]phenyl]indolin-2-one;

3-[(3-cyclopropylisoxazol-5-yl)-hydroxy-methylene]-4,6-difluoro-5-[4-[1-(hydroxymethyl)cyclopropyl]phenyl]indolin-2-one;

6-chloro-5-[4-[2-hydroxy-1-(hydroxymethyl)ethyl]phenyl]-3-[hydroxy-(3-methoxyisoxazol-5-yl)methylene]indolin-2-one;

6-chloro-5-[4-(1,2-dihydroxyethyl)phenyl]-3-[hydroxy-(3-methoxyisoxazol-5-yl)methylene]indolin-2-one;

6-chloro-5-[4-[1-(hydroxymethyl)cyclopropyl]phenyl]-3-[hydroxy-(5-methyl-2-thienyl)methylene]indolin-2-one;

6-chloro-3-[hydroxy-(3-methoxyisoxazol-5-yl)methylene]-5-[4-[(1-methyl-4-piperidyl)oxy]phenyl]indolin-2-one hydrochloride;
6-fluoro-3-[(3-fluoro-4-methoxy-phenyl)-hydroxy-methylene]-5-[4-[1-(hydroxymethyl)cyclopropyl]phenyl]indolin-2-one;
6-chloro-3-[2-furyl(hydroxy)methylene]-5-[4-[1-(hydroxymethyl)cyclopropyl]phenyl]indolin-2-one;
6-chloro-5-(4-dimethylaminophenyl)-3-[hydroxy-(3-methoxyisoxazol-5-yl)methylene]indolin-2-one;
6-chloro-3-[hydroxy-(3-methoxyisoxazol-5-yl)methylene]-5-(4-tetrahydropyran-4-yloxyphenyl)indolin-2-one;
6-chloro-3-[hydroxy-(3-methoxyisoxazol-5-yl)methylene]-5-[4-(3-hydroxypropoxy)phenyl]indolin-2-one;
6-chloro-3-[(5-chloro-2-thienyl)-hydroxy-methylene]-5-[4-[1-(hydroxymethyl)cyclopropyl]phenyl]indolin-2-one;
6-chloro-3-[hydroxy-(3-methoxyisoxazol-5-yl)methylene]-5-[4-(3-methoxypropoxy)phenyl]indolin-2-one;
6-chloro-3-[hydroxy-(3-methylisoxazol-5-yl)methylene]-5-[4-(oxetan-3-ylmethoxy)phenyl]indolin-2-one;
6-chloro-3-[hydroxy-(3-methoxyisoxazol-5-yl)methylene]-5-[4-(1-methylpyrrolidin-3-yl)phenyl]indolin-2-one hydrochloride;
6-chloro-3-[hydroxy-(3-methoxyisoxazol-5-yl)methylene]-5-(4-pyrrolidin-3-ylphenyl)indolin-2-one hydrochloride;
6-chloro-5-[4-(3-hydroxycyclobutyl)phenyl]-3-[hydroxy-(3-methoxyisoxazol-5-yl)methylene]indolin-2-one;
6-chloro-3-[hydroxy-(3-methoxyisoxazol-5-yl)methylene]-5-[4-(thiazol-5-ylmethoxy)phenyl]indolin-2-one;
6-chloro-3-[hydroxy-(3-methoxyisoxazol-5-yl)methylene]-5-(4-pyrrolidin-1-ylphenyl)indolin-2-one;
6-chloro-3-[(2,3-difluorophenyl)-hydroxy-methylene]-5-[4-[1-(hydroxymethyl)cyclopropyl]phenyl]indolin-2-one;
6-chloro-5-[4-[(3-hydroxycyclobutyl)methoxy]phenyl]-3-[hydroxy-(3-methoxyisoxazol-5-yl)methylene]indolin-2-one;
6-chloro-3-[hydroxy-(5-methoxy-2-pyridyl)methylene]-5-(4-morpholinophenyl)indolin-2-one;
6-chloro-3-[(2,4-difluorophenyl)-hydroxy-methylene]-5-[4-[1-(hydroxymethyl)cyclopropyl]phenyl]indolin-2-one;
6-chloro-3-[(5-fluoro-3-pyridyl)-hydroxy-methylene]-5-[4-[1-(hydroxymethyl)cyclopropyl]phenyl]indolin-2-one;
6-chloro-3-[(3,4-difluorophenyl)-hydroxy-methylene]-5-[4-[1-(hydroxymethyl)cyclopropyl]phenyl]indolin-2-one;
6-chloro-3-[(3,5-difluorophenyl)-hydroxy-methylene]-5-[4-[1-(hydroxymethyl)cyclopropyl]phenyl]indolin-2-one;
6-chloro-5-[2-(dimethylamino)pyrimidin-5-yl]-3-[hydroxy-(3-methoxyisoxazol-5-yl)methylene]indolin-2-one;
6-chloro-5-[6-(dimethylamino)-3-pyridyl]-3-[hydroxy-(3-methoxyisoxazol-5-yl)methylene]indolin-2-one;
6-chloro-5-[4-(dimethylamino)-3-fluoro-phenyl]-3-[hydroxy-(3-methoxyisoxazol-5-yl)methylene]indolin-2-one;
6-chloro-5-[4-(dimethylamino)-2-fluoro-phenyl]-3-[hydroxy-(3-methoxyisoxazol-5-yl )methylene]indolin-2-one;
6-chloro-5-(3-fluoro-4-morpholino-phenyl)-3-[hydroxy-(3-methoxyisoxazol-5-yl)methylene]indolin-2-one;
6-chloro-3-[(3,5-difluorophenyl)-hydroxy-methylene]-5-[4-(1-methylpyrrolidin-3-yl)phenyl]indolin-2-one hydrochloride;
6-chloro-3-[hydroxy-(6-methoxy-3-pyridyl)methylene]-5-(4-morpholinophenyl)indolin-2-one;
6-chloro-5-[4-(4-hydroxycyclohexoxy)phenyl]-3-[hydroxy-(3-methoxyisoxazol-5-yl)methylene]indolin-2-one;
6-chloro-5-[4-[cyclopropyl(methyl)amino]phenyl]-3-[hydroxy-(3-methoxyisoxazol-5-yl)methylene]indolin-2-one;
6-chloro-3-[hydroxy-(3-methoxyisoxazol-5-yl)methylene]-5-(1-methylindol-5-yl)indolin-2-one;
6-chloro-3-[(2,4-difluorophenyl)-hydroxy-methylene]-5-[4-(3-hydroxycyclobutyl)phenyl]indolin-2-one;
6-chloro-3-[hydroxy-(3-methoxyisoxazol-5-yl)methylene]-5-[4-(3-hydroxypyrrolidin-1-yl)phenyl]indolin-2-one;
6-chloro-3-[furo[2,3-b]pyridin-2-yl(hydroxy)methylene]-5-[4-[1-(hydroxymethyl)cyclopropyl]phenyl]indolin-2-one;
6-chloro-3-[hydroxy-(2-methoxy-4-pyridyl)methylene]-5-[4-[1-(hydroxymethyl)cyclopropyl]phenyl]indolin-2-one;
6-chloro-3-[(2,5-difluoro-4-methoxy-phenyl)-hydroxy-methylene]-5-[4-(3-hydroxycyclobutyl)phenyl]indolin-2-one;
6-chloro-3-[(3-fluoro-4-pyridyl)-hydroxy-methylene]-5-[4-[1-(hydroxymethyl)cyclopropyl]phenyl]indolin-2-one;
6-chloro-3-[(3,5-difluorophenyl)-hydroxy-methylene]-5-[4-(3-hydroxycyclobutyl)phenyl]indolin-2-one;
5-[4-(azetidin-1-yl)phenyl]6-chloro-3-[hydroxy-(3-methoxyisoxazol-5-yl)methylene]indolin-2-one;
6-chloro-3-[(2,4-dimethoxyphenyl)-hydroxy-methylene]-5-[4-[1-(hydroxymethyl)cyclopropyl]phenyl]indolin-2-one;
3-[(3-tert-butylisoxazol-5-yl)-hydroxy-methylene]6-chloro-5-[4-(3-hydroxycyclobutyl)phenyl]indolin-2-one;
6-chloro-3-[hydroxy-(3-methoxyisoxazol-5-yl)methylene]-5-[4-(3-methoxycyclobutyl)phenyl]indolin-2-one;
6-chloro-5-[4-(3-hydroxycyclobutyl)phenyl]-3-[hydroxy-(3-isopropoxyisoxazol-5-yl)methylene]indolin-2-one;
6-chloro-3-[hydroxy-(3-methoxyisoxazol-5-yl)methylene]-5-[4-[1-(2,2,2-trifluoroethyl)pyrrolidin-3-yl]phenyl]indolin-2-one hydrochloride;
3-[benzofuran-2-yl(hydroxy)methylene]6-chloro-5-[4-[1-(hydroxymethyl)cyclopropyl]phenyl]indolin-2-one;
6-chloro-3-[furo[3,2-b]pyridin-2-yl(hydroxy)methylene]-5-[4-[1-(hydroxymethyl)cyclopropyl]phenyl]indolin-2-one;
6-chloro-3-[(5-chlorobenzofuran-2-yl)-hydroxy-methylene]-5-[4-[1-(hydroxymethyl)cyclopropyl]phenyl]indolin-2-one;
6-chloro-3-[(2-fluorophenyl)-hydroxy-methylene]-5-[4-(3-hydroxycyclobutyl)phenyl]indolin-2-one;
6-chloro-5-[4-[3-(dimethylamino)propoxy]phenyl]-3-[hydroxy-(3-methoxyisoxazol-5-yl)methylene]indolin-2-one;
6-chloro-3-[(3-cyclopropylisoxazol-5-yl)-hydroxy-methylene]-5-[4-(3-hydroxycyclobutyl)phenyl]indolin-2-one;
6-chloro-3-[hydroxy-(3-methoxy-4-pyridyl)methylene]-5-[4-[1-(hydroxymethyl)cyclopropyl]phenyl]indolin-2-one;

6-chloro-5-[4-(2,2-dimethyl-1,3-dioxan-5-yl)phenyl]-3-[hydroxy-(3-methoxyisoxazol-5-yl)methylene]indolin-2-one;

6-chloro-3-[hydroxy-(3-methoxyisoxazol-5-yl)methylene]-5-[4-(6-oxa-2-azaspiro[3.3]heptan-2-yl)phenyl]indolin-2-one;

6-chloro-3-[hydroxy-(2-methoxy-3-pyridyl)methylene]-5-[4-[1-(hydroxymethyl)cyclopropyl]phenyl]indolin-2-one;

6-chloro-3-[hydroxy-(3-methoxyisoxazol-5-yl)methylene]-5-[4-[3-hydroxypropyl(methyl)amino]phenyl]indolin-2-one;

6-chloro-5-[4-(3-fluoroazetidin-1-yl)phenyl]-3-[hydroxy-(3-methoxyisoxazol-5-yl)methylene]indolin-2-one;

6-chloro-5-[4-(3,3-difluoroazetidin-1-yl)phenyl]-3-[hydroxy-(3-methoxyisoxazol-5-yl)methylene]indolin-2-one;

6-chloro-3-[furo[3,2-b]pyridin-2-yl(hydroxy)methylene]-5-[4-(3-hydroxypyrrolidin-1-yl)phenyl]indolin-2-one;

6-chloro-3-[hydroxy-(6-methoxy-2-pyridyl)methylene]-5-[4-[1-(hydroxymethyl)cyclopropyl]phenyl]indolin-2-one;

6-chloro-3-[hydroxy-(3-methoxy-2-pyridyl)methylene]-5-[4-[1-(hydroxymethyl)cyclopropyl]phenyl]indolin-2-one;

6-chloro-3-[(3-ethoxyisoxazol-5-yl)-hydroxy-methylene]-5-[4-(3-hydroxycyclobutyl)phenyl]indolin-2-one;

6-chloro-3-[hydroxy-(3-methoxyisoxazol-5-yl)methylene]-5-[4-(1-methylazetidin-3-yl)phenyl]indolin-2-one;

6-chloro-3-[hydroxy-(3-methoxyisoxazol-5-yl)methylene]-5-[4-[(3R)-3-hydroxypyrrolidin-1-yl]phenyl]indolin-2-one;

6-chloro-3-[hydroxy-(3-methoxyisoxazol-5-yl)methylene]-5-[4-[(3S)-3-hydroxypyrrolidin-1-yl]phenyl]indolin-2-one;

6-chloro-3-[(2-fluorophenyl)-hydroxy-methylene]-5-[4-(3-hydroxypyrrolidin-1-yl)phenyl]indolin-2-one;

6-chloro-3-[2-(dimethylamino)pyrimidin-5-yl]-hydroxy-methylene]-5-[4-(3-hydroxypyrrolidin-1-yl)phenyl]indolin-2-one;

6-chloro-5-[4-(3,3-dimethylazetidin-1-yl)phenyl]-3-[hydroxy-(3-methoxyisoxazol-5-yl)methylene]indolin-2-one;

6-chloro-3-[(3-cyclopropylisoxazol-5-yl)-hydroxy-methylene]-5-[4-(3-hydroxypyrrolidin-1-yl)phenyl]indolin-2-one;

6-chloro-3-[hydroxy-(3-methoxyisoxazol-5-yl)methylene]-5-[4-[3-(hydroxymethyl)azetidin-1-yl]phenyl]indolin-2-one;

6-chloro-5-[4-[1-(hydroxymethyl)cyclopropyl]phenyl]-3-[hydroxy (thieno[2,3-b]pyridin-2-yl)methylene]indolin-2-one hydrochloride;

6-chloro-3-[hydroxy-(3-methoxyisoxazol-5-yl)methylene]-5-[4-[(3S,4S)-3-hydroxy-4-methoxy-pyrrolidin-1-yl]phenyl]indolin-2-one;

6-chloro-5-[4-[1-(2-chloroethyl)-2-methyl-prop-1-enyl]phenyl]-3-[hydroxy-(3-methoxyisoxazol-5-yl)methylene]indolin-2-one;

6-chloro-3-[hydroxy-(3-methoxyisoxazol-5-yl)methylene]-5-[4-(4-hydroxy-1-piperidyl)phenyl]indolin-2-one;

6-chloro-5-[4-[(3R)-3-fluoropyrrolidin-1-yl]phenyl]-3-[hydroxy-(3-methoxyisoxazol-5-yl)methylene]indolin-2-one;

chloro-3-[hydroxy-(1-methylindol-5-yl)methylene]-5-[4-(3-hydroxypyrrolidin-1-yl)phenyl]indolin-2-one;

6-chloro-5-(2,6-difluoro-4-morpholino-phenyl)-3-[hydroxy-(3-methoxyisoxazol-5-yl)methylene]indolin-2-one;

6-chloro-3-[hydroxy-(3-methoxyisoxazol-5-yl)methylene]-5-[4-[2-(hydroxymethyl)azetidin-1-yl]phenyl]indolin-2-one;

6-chloro-3-[hydroxy-(3-methoxyisoxazol-5-yl)methylene]-5-[4-[(2S)-2-(hydroxymethyl)pyrrolidin-1-yl]phenyl]indolin-2-one;

6-chloro-3-[hydroxy-(3-methoxyisoxazol-5-yl)methylene]-5-[4-[(2R)-2-(hydroxymethyl)pyrrolidin-1-yl]phenyl]indolin-2-one;

4-[4-[6-chloro-3-[hydroxy-(3-methoxyisoxazol-5-yl)methylene]-2-oxo-indolin-5-yl]phenyl]cyclohex-3-ene-1-carboxylic acid;

trans-6-chloro-3-[hydroxy-(3-methoxyisoxazol-5-yl)methylene]-5-[4-[(3S,4R)-4-hydroxytetrahydrofuran-3-yl]phenyl]indolin-2-one;

cis-6-chloro-3-[hydroxy-(3-methoxyisoxazol-5-yl)methylene]-5-[4-[(2S,4S)-4-hydroxytetrahydrofuran-2-yl]phenyl]indolin-2-one;

trans-6-chloro-3-[hydroxy-(3-methoxyisoxazol-5-yl)methylene]-5-[4-[(2R,4S)-4-hydroxytetrahydrofuran-2-yl]phenyl]indolin-2-one;

6-chloro-3-[hydroxy-(3-methoxyisoxazol-5-yl)methylene]-5-[4-(4-hydroxy-4-methyl-1-piperidyl)phenyl]indolin-2-one;

6-chloro-3-[hydroxy-(3-methoxyisoxazol-5-yl)methylene]-5-[4-[2-(hydroxymethyl)morpholin-4-yl]phenyl]indolin-2-one; and 6-chloro-3-[hydroxy-(3-methoxyisoxazol-5-yl)methylene]-5-[4-[3-(hydroxymethyl)morpholin-4-yl]phenyl]indolin-2-one, in the form of the base, an enantiomer, a diastereoisomer, or an addition salt with an acid or with or a pharmaceutically acceptable salt of this compound.

12. A pharmaceutical composition comprising a compound as claimed in claim 1, or a pharmaceutically acceptable salt of this compound, and also at least one pharmaceutically acceptable excipient.

* * * * *